(12) United States Patent
Schinazi et al.

(10) Patent No.: US 7,211,570 B2
(45) Date of Patent: May 1, 2007

(54) TREATMENT OF EBV AND KHSV INFECTION

(75) Inventors: Raymond F. Schinazi, Decatur, GA (US); Junxing Shi, Duluth, GA (US); Joyce D. Fingeroth, Sudbury, MA (US); Erik Gustafson, Norwood, MA (US)

(73) Assignees: Pharmasset, Inc., Princeton, NJ (US); Emory University, Atlanta, GA (US); Beth Israel Deaconess Medical Center, Boston, MA (US)

( * ) Notice: Subject to any disclaimer, the term of this patent is extended or adjusted under 35 U.S.C. 154(b) by 813 days.

(21) Appl. No.: 10/326,444

(22) Filed: Dec. 19, 2002

(65) Prior Publication Data

US 2003/0176392 A1 Sep. 18, 2003

Related U.S. Application Data

(60) Provisional application No. 60/345,130, filed on Dec. 20, 2001.

(51) Int. Cl.
- A61K 31/70 (2006.01)
- A01N 43/06 (2006.01)
- A01N 43/26 (2006.01)
- A01N 47/10 (2006.01)
- A01N 43/54 (2006.01)

(52) U.S. Cl. ............... 514/49; 514/444; 514/463; 514/476; 514/256

(58) Field of Classification Search ........... 514/274, 514/15, 256
See application file for complete search history.

(56) References Cited

U.S. PATENT DOCUMENTS

| | | | |
|---|---|---|---|
| 4,247,544 A | 1/1981 | Bergstrom et al. | |
| 4,382,925 A | 5/1983 | de Clercq et al. | |
| 4,424,211 A | 1/1984 | Jones et al. | |
| 4,542,210 A | 9/1985 | Sakata et al. | |
| 4,681,933 A | 7/1987 | Chu et al. | |
| 4,841,039 A | 6/1989 | Chu et al. | |
| 4,957,924 A | 9/1990 | Beauchamp | |
| 5,079,235 A * | 1/1992 | Purifoy et al. | ............ 514/49 |
| 5,356,882 A | 10/1994 | Walker et al. | |
| 5,565,438 A | 10/1996 | Chu et al. | |
| 5,567,688 A | 10/1996 | Chu et al. | |
| 5,587,362 A | 12/1996 | Chu et al. | |

(Continued)

FOREIGN PATENT DOCUMENTS

WO     WO 95/07287     3/1995

(Continued)

OTHER PUBLICATIONS

Lin J-C, et. al. Antiviral Research, 17, 1992, 43-52.*

(Continued)

*Primary Examiner*—Shaojia Anna Jiang
*Assistant Examiner*—Roy P. Issac
(74) *Attorney, Agent, or Firm*—Merchant & Gould

(57) ABSTRACT

A method and composition for the treatment, prevention and/or prophylaxis of a host, and in particular, a human, infected with Epstein-Barr virus (EBV), is provided that includes administering an effective amount of a 5-substituted uracil nucleoside or its pharmaceutically acceptable salt or prodrug, optionally in a pharmaceutically acceptable diluent or excipient.

10 Claims, 18 Drawing Sheets

U.S. PATENT DOCUMENTS

| | | | |
|---|---|---|---|
| 5,792,773 | A | 8/1998 | Chu et al. |
| 6,022,876 | A | 2/2000 | Chu et al. |
| 6,177,436 | B1 | 1/2001 | Spector et al. |
| 6,274,589 | B1 | 8/2001 | Chu et al. |
| 2002/0025296 | A1* | 2/2002 | Knaus et al. ............... 424/1.17 |

FOREIGN PATENT DOCUMENTS

| | | |
|---|---|---|
| WO | WO 96/13512 | 5/1996 |
| WO | WO 96/40164 | 12/1996 |
| WO | WO 00/09531 | 2/2000 |

OTHER PUBLICATIONS

Merck Manual of Diagnostics, 16th Edition, 1992, 2281-2285.*
Straus et. al. Epstein-Barr Virus Infections: Biology, Pathogenesis, and Management; Annals of Internal Medicine, 1993, 118, 45-58.*
Kumar et. al. Synthesis of 5-[1-hydroxy (or methoxy)-2,2-dihaloethyl]-2'-deoxyuridines with antiviral and cytotoxic activity, Antiviral Research (1994), 24(4), 315-25.*
Anisimová, E., et al., (1984) "Effects of n-butyrate and phorbol ester (TPA) on induction of EBV antigens and cell differentiation" Arch. Virol., 81, 223-237.
Ansari, A, et al., (1999) "The U69 gene of human herpesvirus 6 encodes a protein kinase which can confer ganciclovir sensitivty to baculoviruses" J. Virol., 73(4), 3284-3291.
Balzarini, J., et al., (1989) "Synthesis and antiviral activity of the enantiomeric forms of carba-5-iodo-2'-deoxyuridine and carba-(E)-5-(2-bromovinyl)-2'-deoxyuridine", J. Med. Chem., 32, 1861-1865.
Barba, D., et al. (1994) "Development of anti-tumor immunity following thymidine kinase-mediated killing of experimental brain tumors", Proc. Natl. Acad. Sci. USA, 91, 4348-52.
Basnak, I., et al., (1998) Nucleosides and Nucleotides, 17, 29-38.
Beauchamp L.M., et al., (1988) "Effect of acyclic pyrimidines related to 0-[(1,3-dihycroxy-2-propoxy)methyl]guanine on herpesviruses", J. Med. Chem., 31, 144-149.
Belen'kii, M.S., et al., (1994) "Multiple drug effect analysis with confidence interval", Antiviral Res., 25, 1-11.
Brand, K., et al., "Liver-associated toxicity of the HSV-tk/GCV approach and adenoviral vectors", Cancer Gene Therap, 4, 9-16; 1997.
Cannon, J.S., et al., (1999) "Human herpesvirus 8-encoded thymidine kinase and phosphotransferase homologues confer sensitivity to ganciclovir" J. Virol., 73(6), 4786-4793.
Caruso, M., et al., (1993) "Regression of established macroscopic liver metastases after in-situ transduction of a suicide gene" Proc. Natl. Acad. Sci. USA, 90, 7024-7028.
Chen, S.-H., et al., (1994) "Gene therapy for brain tumors: regression of experimental gliomas by adenovirus-mediated gene transfer in vivo" Proc Natl Acad Sci USA, 91, 3054-3057.
Cheng, Y.-C., et al., (1983) "Unique spectrum of activity of 9-[(1,3-dihydroxy-2-propoxy)methyl]-guanine against herpesviruses in vitro and its mode of action against herpes simplex virus type 1", Proc. Natl., Acad. Sci. USA, 80, 2767-2770.
Choi, Y., et al., (2000) "Structure-activity relationships of (E)-5-(2-bromovinyl)uracil and related pyrimidine nucleosides as antiviral agents for herpes virus", J. Med. Chem., 43, 2538-2546.
Chou, T.-C., et al., (1984), "Quantitative analysis of dose-effect relationships: the combined effects of multiple drugs or enzyme inhibitors", Adv. Enzyme Regul., 22, 27-55.
Culver K.W., et al. (1992) "In vivo gene transfer with retroviral vector-producer cells for treatment of experimental brain tumors", Science, 256, 1550-1552.
Daniel, P., et al., (1989) "Pharmacokinetic study of butyric acid administered in vivo as sodium and arginine butyrate salts", Clin. Chim. Acta, 181, 255-263.
Datta et al., (1980) "Acyclovir inhibition of Epstein-Barr virus replication", Proc. Natl., Acad. Sci. USA, 77, 5163-5166.
Datta et al., (1981) "Mechanism of inhibition of Epstein-Barr virus replication by phosphonoformic acid", Virol., 114, 52-59.

Dyson, M.R., et al., (1991) "The synthesis and antiviral activity of some 4'-thio-2'-deoxy nucleoside analogues", J. Med. Chem., 34, 2782-2786.
Emery, V.C., et al., (2000) "Prediction of cytomegalovirus load and resistance patterns after antiviral chemotherapy", Proc. Natl. Acad. Sci., 97(14), 8039-44.
Gustafson, E.A., et al., (1998) "The Epstein-Barr virus thymidine kinase does not phosphorylate ganciclovir or acyclovir and demonstrates a narrow specificity compared to herpes simplex virus type 1 thymidine kinase", Antimicrob. Agents Chemother., 42(11), 2923-31.
Gustafson, E.A., et al., (2000) "Human herpesvirus 8 open reading frame 21 is a thymidine and thymidylate kinase of narrow substrate specificity that efficiently phosphorylates zidovudine but not ganciclovir" J. Virol., 74, 684-692.
Hamel, W., et al., (1996) "Herpes simplex virus thymidine kinase/ganciclovir-mediated apoptotic death of bystander cells.", Cancer Res., 56, 2697-2702.
Herdewijn, P., et al. (1985) "Synthesis and antiviral activity of the carbocyclic analogues (E)-5-(2-halovinyl)-2'-deoxyuridines and (E)-5-(2-halovinyl)-2'-deoxycytidines", J. Med. Chem. 28, 550-555.
Hoffer, M., (1960) "α-Thymidin", Chem. Ber., 93, 2777-2781.
Holy, A. (1972) "Nucleic acid components and their analogues. CLIII. Preparation of 2'-deoxy-L-ribonucleosides of the pyrimidine series", Coll. Czech. Chem. Commun., 37, 4072-4086.
Imamura, K., et al. (1997) "Synthesis and in vitro evaluation of 5-closo- and 5-nido-orthocarbonyluridines as boron carriers", Bull. Chem. Soc. Jpn., 70, 3103-3110.
Jones, A.S., et al. (1979) "The synthesis of the potent anti-herpes virus agent, E-5-(2-bromovinyl)-2'-deoxyuridine and related compounds", Tetrahedron Lett., 45, 4415-4418.
Kam, b.L. et al. (1981) "Carbocyclic sugar amines: synthesis and stereochemistry of racemic α- and β-carbocyclic ribofuranosylamine, carbocyclic lyxofuranosylamine, and related compounds", J. Org. Chem., 46, 3268-3272.
Kim, J.H., et al. (1995) "Selective enhancement of radiation response of herpes simplex virus thymidine kinase transduced 9L gliosarcoma cells in vitro and in vivo by antiviral agents." Int. J. Radiat. Oncol. Biol. Phys., 33, 861-868.
Lin, J.-C., et al., (1987) "Novel acyclic adenosine analogs inhibit Epstein-Barr virus replication", Antimicrob. Agents & Chemotherapy, 31(9), 1431-1433.
Lin, J.-C., et al,. (1988) "Anti-Human Immunodeficiency Virus agent 3'-azido-3'-deoxythymidine inhibits replaction of Epstein-Barr virus", Antimicrob. Agents & Chemotherapy, 32(2), 265-267.
Lin, J.-C., et al. (1988) "Comparison of two bromovinyl nucleoside analogs, 1-β-D-arabinofuranosyl-E-5-(2-bromovinyl)uracil and E-5-(2-bromovinyl)-2'-deoxyuridine, with acyclovir in inhibition of Epstein-Barr virus replication", Antimicrob. Agents Chemo., 32(7), 1068-1072.
Lin, J.-C., et al., (1984) "Prolonged inhibitory effect of 9-(1,3-dihydroxy-2-propoxymethyl)guanine against replication of Epstein-Barr virus", J. Virol., 50(1), 50-55.
Lin, J.C. (1999) "Antiviral therapy for Epstein-Barr virus: the challenge ahead", Recent Res. Develop. Antimicrob. Agents and Chemother, 3, 191-223.
Lin, J.-S., et al., (1999) "Structure-activity relationships of L-dioxolane uracil nucleosides as anti-Epstein Barr virus agents", J. Med. Chem., 42(12), 2212-2217.
Lin, T.-S., et al. (1995) "Synthesis of several pyrimidine L-nucleoside analogues as potential antiviral agents", Tetrahedron, 51(4), 1055-1068.
Ma, T., et al. (1996) "Structure-activity relationships of 1-(2-deoxy-2-fluoro-β-L-arabino-furanoxyl)pyrimidine nucleosides as anti-hepatitis B virus agents", J. Med. Chem. 39, 2835-2843.
Martin, J.C., et al. (1983) "9-[(1,3-Dihydroxy-2-propoxy)methyl]quanine: a new potent and selective antiherpes agent", J. Med. Chem. 26, 759-761.
McGee D.P.C., et al., (1985) "Synthesis and antiherpes simplex virus activity of 9-[(1,3-dihydroxy-2-propylthio)methyl]guanine", J. Med. Chem. 28, 1242-1245.

Moolten, F.L. (1986) "Tumor chemosensitivity conferred by inserted herpes thymidine kinase genes: paradigm for a prospective cancer control strategy.", *Cancer Res.*, 49, 5276-5281.

Moore, S.M., et al., (2001) "Induction of Epstein-Barr virus kinases to sensitize tumor cells to nucleoside analogues" *Antimicrob Agents Chemother*, 45(7), 2082-91.

Ogilvie, K.K., et al., (1984) "Uracil analogues of the acyclonucleoside 9-[(2-hydroxy-1-(hydroymethyl)ethoxy)-methyl]guanine (BIOLF-62)", *Can. J. Chem.* 62, 16-21.

Ooka, T., et al., (1980) "Effects of arabinofuranosylthymine on Epstein-Barr virus replication", *Virol.*, 104, 219-223.

Pagano, J.S. (1995) "Epstein-Barr virus: therapy of active and latent infection", *Antiviral Chemotherapy*, (eds. Jeffries & De Clercq), John Wiley & Sons, Chichester, 155-195.

Perrine S.P., et al., (1993) "A short-term trial of butyrate to stimulate fetal globin-gene expression in beta-globin disorders", *N. Engl. J. Med.*, 328, 81-86.

Prendiville, J., et al., (1993) "A phase I study of intravenous bryostatin 1 in patients with advanced cancer", *Br. J. Cancer*, 68, 418-424.

Qian, C., et al., "Gene transfer and therapy with adenoviral vector in rats with diethylnitrosamine-induced hepatocellular carcinoma", *Hum. Gene Ther.* 1997; 8, 349-358.

Rahim S.G., et al., (1996) "Synthesis and anti-Herpes virus activity of 2'-deoxy-4'-thiopyrimidine nucleosides", *J. Med. Chem.* 39, 789-795.

Robins, M.J., et al., (1983), "Nucleic acid compounds. 39. Efficient conversion of 5-iodo to 5-alkynyl and derived 5-substituted uracil bases and nucleosides", *J. Org. Chem.* 48, 1854-1862.

Rubsam, L.Z., et al., (1998) "Superior cytotoxicity with ganciclovir compared with acyclovir and 1-β-D-arabinofuranosylthymine in herpes simplex virus-thymidine kinase-expressing cells: a novel paradigm for cell killing", *Cancer Res.* 58(17), 3873-82.

Schinazi, R.F., et al., (1990) "Activities of 3'-azido-3'-deoxythymidine nucleotide dimmers in primary lymphocytes infected with Human Immunodeficiency Virus type 1", *Antimicrob. Agents & Chemother.* 34(6), 1061-1067.

Schinzai, R.F., et al., (1992) "Selective inhibition of human immunodeficiency viruses by racemates and enantiomers of *cis*-5-fluoro-1-[2-(hydroxymethyl)-1,3-oxathiolan-5-yl]cytosine", *Antimicrob. Agents &Chemother.* 36(11), 2423-2431.

Secrist, J.A. III, et al. (1991) "Synthesis amd biological activity of 2'-deoxy-4'-thio pyrimidine nucleosides", *J. Med. Chem.* 34, 2361-2366.

Secrist, J.A. III, et al., (1998) "Synthesis and biological activity of certain 4'-thio-D-arabinofuranosylpurine nucleosides", *J. Med. Chem. 41*, 3865-3871.

Shealy, Y.F., et al. (1976) "Synthesis of the carbocyclic analogs of uracil nucleosides", *J. Heterocycl. Chem.* 13, 1015-1020.

Stinchcobe, T., et al., (1985) "EBV induces a unique pyrimidine 2'-deoxynucleoside kinase activity in superinfected and virus producer B cell lines", *Biochemistry*, 24, 2021-2033.

Tong, X.W., et al., "Adenovirus-mediated thymidine kinase gene transduction in human epithelial ovarian cancer cell lines followed by exposure to ganciclovir", *Anticancer Res.* 1996 16, 1611-1617.

Tsai, C.-H., et al, (1994) "Effect of anti-HIV 1'-β-fluoro-2',3'-dideoxynucleoside analogs on the cellular content of mitochondrial DNA and on lactate production", *Biochem. Pharmacol.* 48(7), 1477-81.

Tung, P.P., et al., (1994) "Substrate specificity of Epstein-Barr virus thymidine kinase" *Antimicrob. Agents Chemother.* 38, 2175-79.

Vile, R.G., et al., (1994) "Systemic gene therapy of murine melanoma using tissue specific expression of the HSVtk gene involves an immune component.", *Cancer Res.* 54, 6228-6234.

Watanabe, K.A., et al., (1984) "Nucelosides. 129. Synthesis of antiviral nucleosides: 5'alkenyl-1-(2-deoxy-2-fluoro-β-D-arabinofuranosyl)uracils", *J. Med. Chem.* 27, 91-94.

Yamamoto, S., et al., (1997) "Herpes simplex virus thymidine kinase/ganciclovir-mediated killing of tumor cells induces tumor-specific cytotoxic T-cells in mice" *Cancer Gene Ther.* 4, 91-96.

Yao, G.-Q., et al., (1993) "Potent inhibition of Epstein-Barr virus by phosphorothioate oligodeoxynucleotides without sequence specification", *Antimicrob. Agents & Chemo. 37*, 1420-1425.

Yao, G.-Q., et al., (1966) "Inhibition of Epstein-Barr virus replication by a novel L-nucleoside, 2'-fluoro-5-methyl-β-L-arabinofuranosyluracil", *Biochem. Pahrm.*, 51, 941-947.

Yee, D., et al., (1996) "Adenovirus-mediated gene transfer of herpes simplex virus thymidine kinase in an ascites model of human breast cancer", *Hum. Gene Ther.* 7, 1251-1257.

* cited by examiner

FIGURE 1. SYNTHESIS OF 5-*E*-(2-CHLOROVINYL)URACIL NUCLEOSIDES
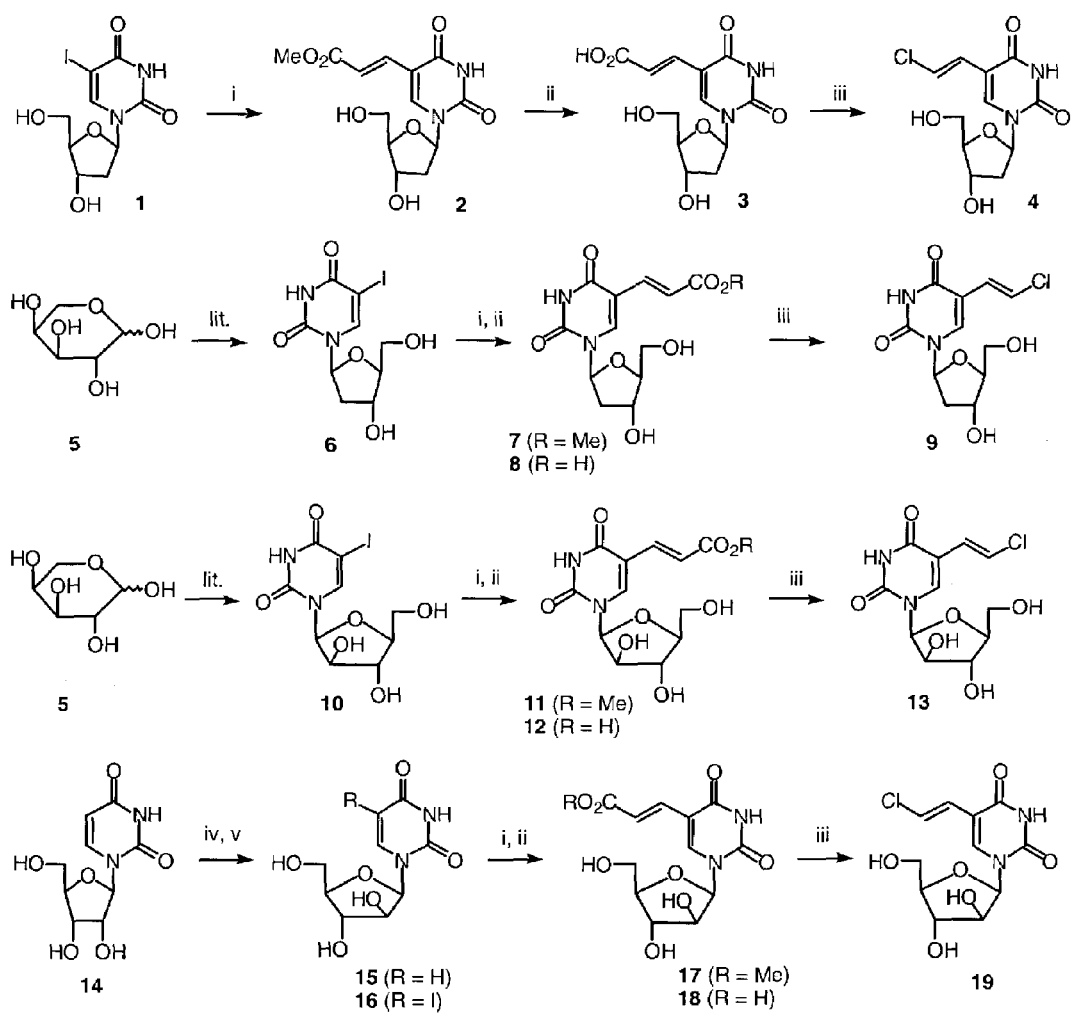
Keys: i. Pd(OAc)$_2$, Ph$_3$P, 1,4-dioxane, methyl acrylate; ii. a) NaOH; b) HCl; iii. KOAc, NCS, H$_2$O; iv. a) Ph$_2$CO$_3$, NaHCO$_3$, HMPT; b) H$_2$O, Et$_3$N; v. I$_2$, 1 N HNO$_3$, CHCl$_3$.

FIGURE 2. SYNTHESIS OF 5-VINYLURACIL NUCLEOSIDES
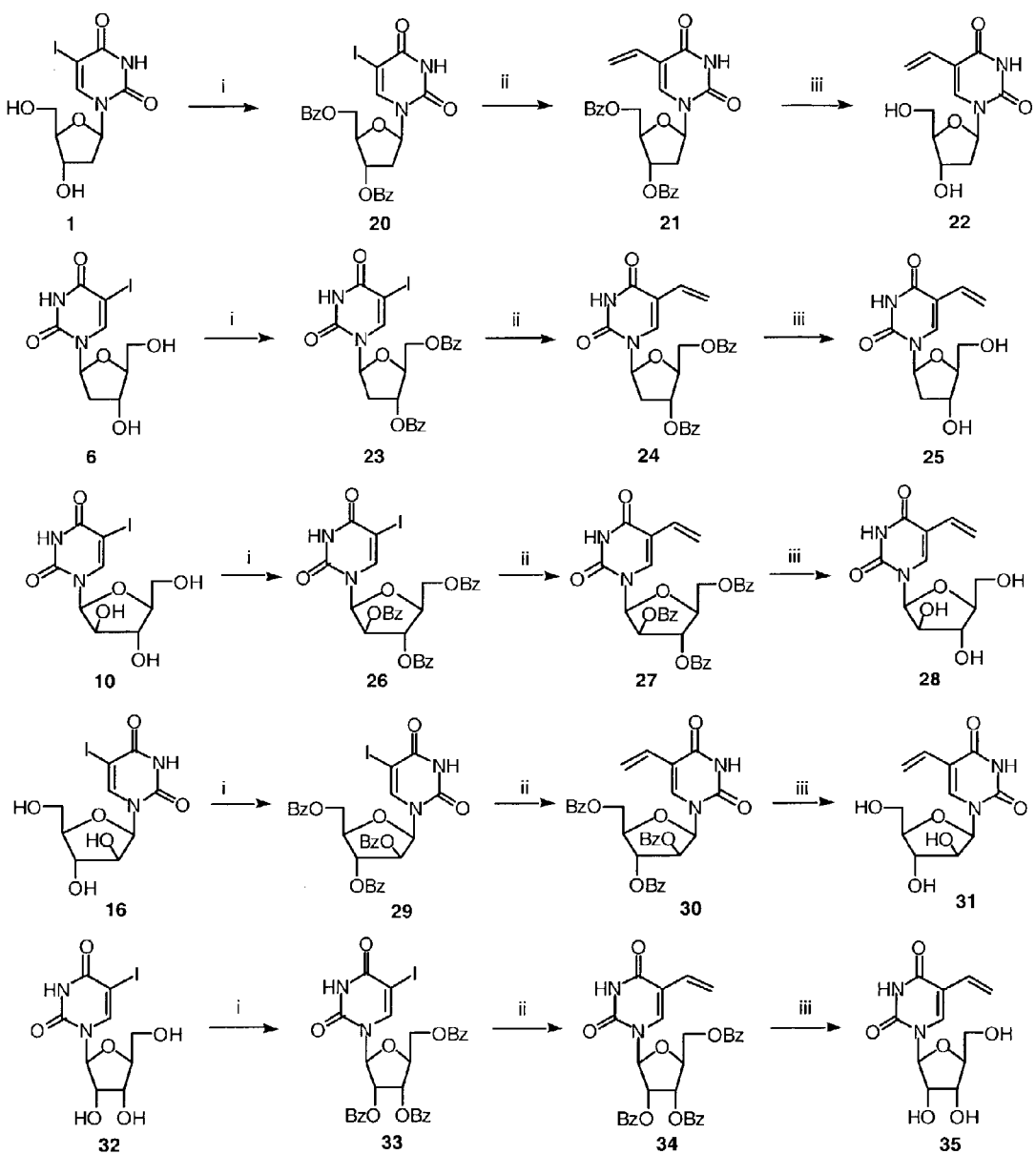
Keys: i. BzCl, pyr.; ii. Pd$_2$dba$_3$, NMP, Bu$_3$SnCH=CH$_2$, tri(2-furyl)phosphine; iii. NH$_3$, MeOH.

FIGURE 3. SYNTHESIS OF 5-ETHYNYLURACIL NUCLEOSIDES
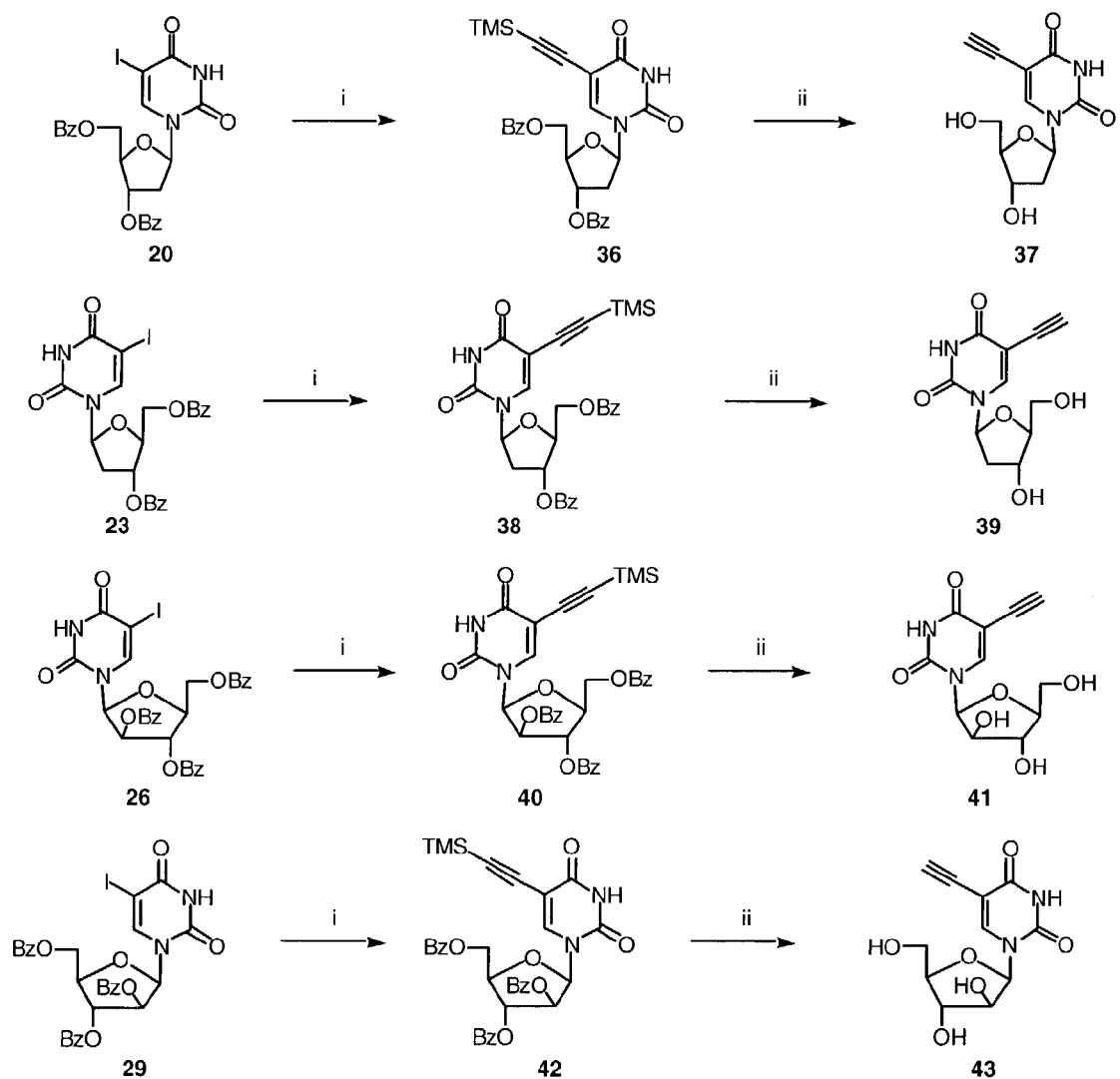
keys: i. (trimethylsilyl)acetylene, PdCl$_2$, Ph$_3$P, CuI, Et$_3$N, THF; ii. a) TBAF, THF; b) NH$_3$, MeOH.

FIGURE 4. SYNTHESIS OF ACYCLIC 5-SUBSTITUTED URACIL NUCLEOSIDES
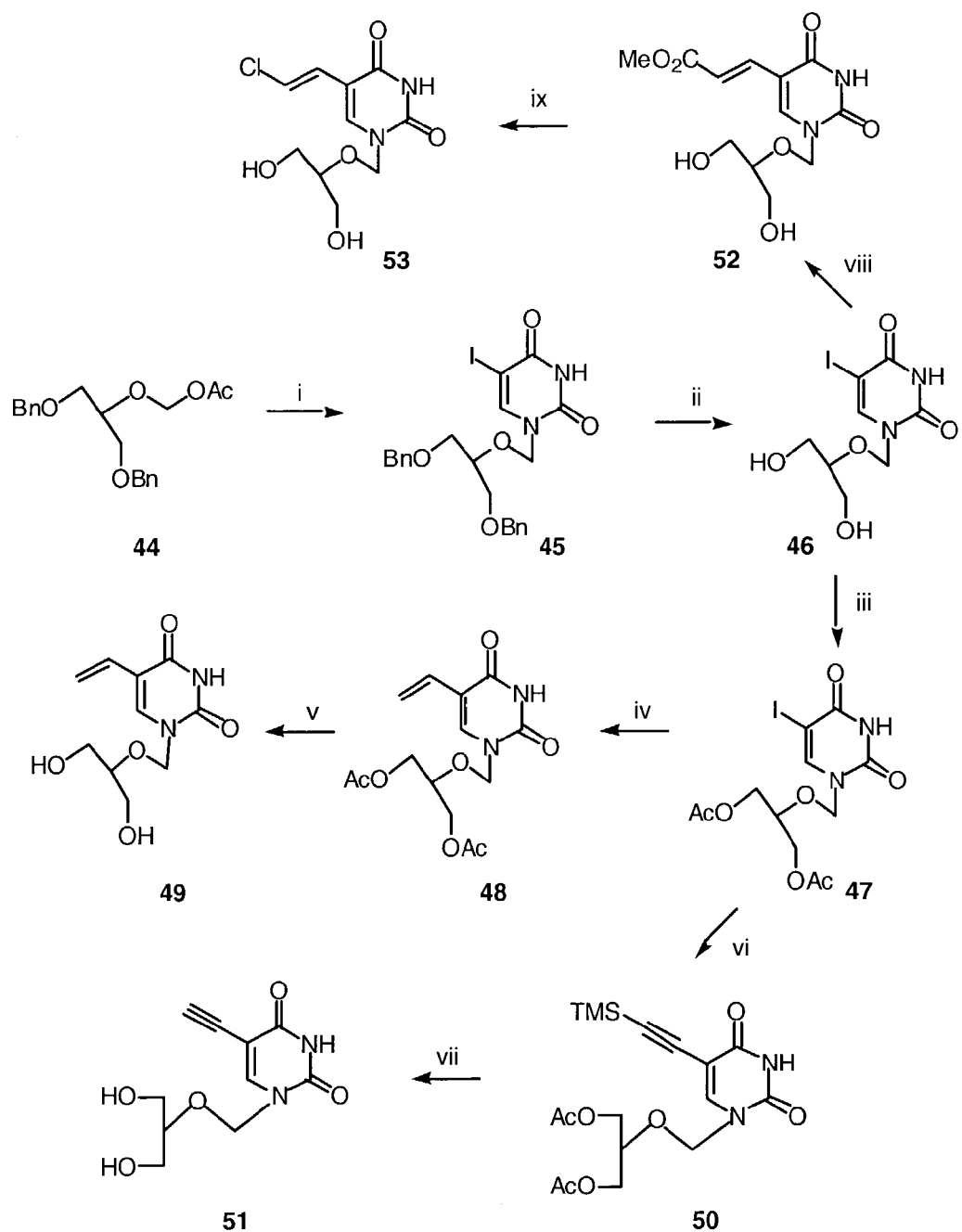
keys: i. 5-IUra, BSA, $CH_2Cl_2$, $SnCl_4$; ii. $BCl_3$, $CH_2Cl_2$; iii. $Ac_2O$, $Et_3N$, DMAP, $CH_2Cl_2$; iv. $Pd_2dba_3$, NMP, $Bu_3SnCH=CH_2$, tri(2-furyl)phosphine; v. $NH_3$, MeOH; vi. (trimethylsilyl)acetylene, $PdCl_2$, $Ph_3P$, CuI, $Et_3N$, THF; vii. a) TBAF, THF; b) $NH_3$, MeOH; viii. $Pd(OAc)_2$, $Ph_3P$, 1,4-dioxane, methyl acrylate; ix. a) NaOH; b) HCl; c) KOAc, NCS, $H_2O$.

FIGURE 5. SYNTHESIS OF 5-SUBSTITUTED URACIL 4'-THIONUCLEOSIDES
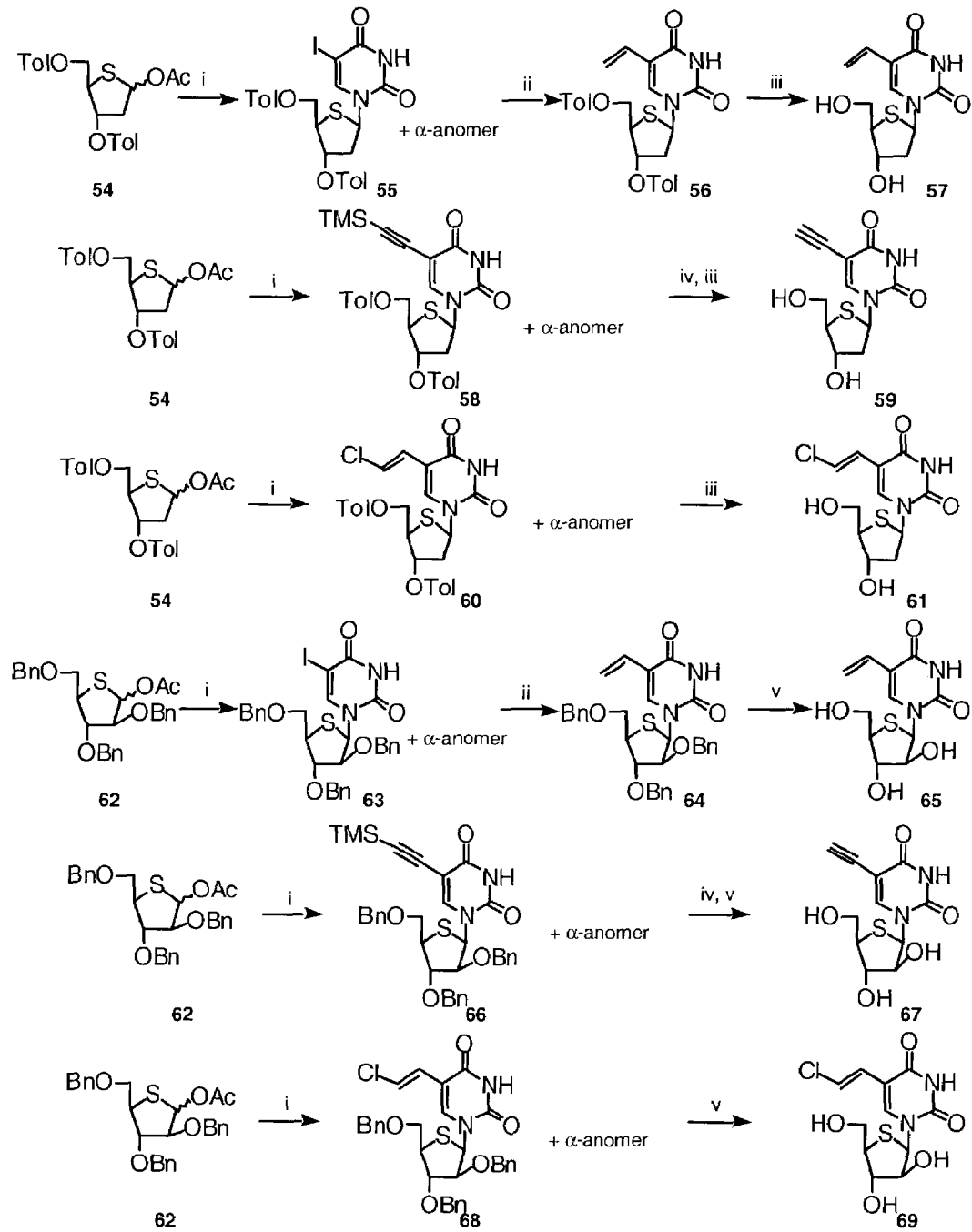
Keys: i. HMDS, pyrimidines, (NH4)$_2$SO$_4$, MeCN, TMSOTf; ii. Pd$_2$dba$_3$, NMP, Bu$_3$SnCH=CH$_2$, tri(2-furyl)phosphine; iii. NaOMe, MeOH; iv. THF, TBAF; v. BBr$_3$, CH$_2$Cl$_2$.

FIGURE 6. SYNTHESIS OF 5-SUBSTITUTED URACIL CARBOCYCLIC NUCLEOSIDES
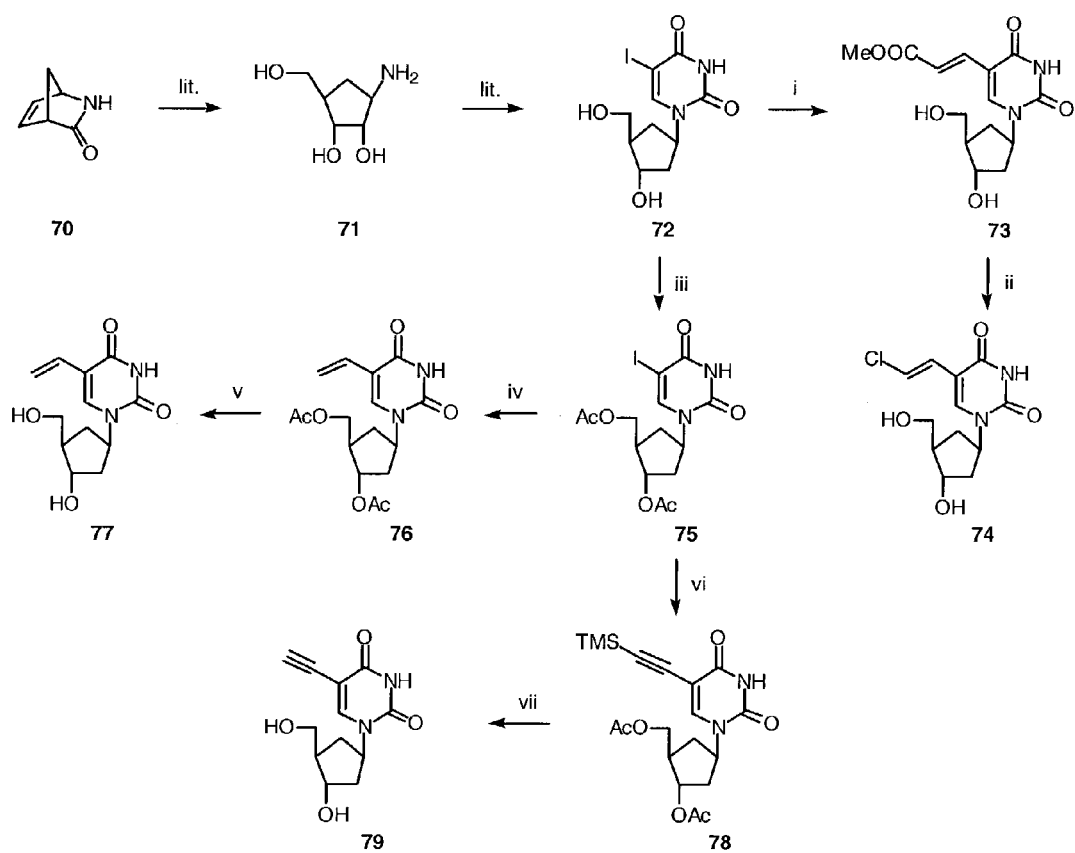
Keys: i. Pd(OAc)$_2$, PH$_3$P, 1,4-dioxane, methyl acrylate; ii. a) NaOH; b) HCl; c) KOAc, NCS, H$_2$O; iii. Ac$_2$O, Et$_3$N, DMAP, CH$_2$Cl$_2$; iv. Pd$_2$dba$_3$, NMP, Bu$_3$SnCH=CH$_2$, tri(2-furyl)phosphine; v. NH$_3$, MeOH; vi. (trimethylsilyl)acetylene, PdCl$_2$, Ph$_3$P, CuI, Et$_3$N, THF; vii. a) TBAF, THF; b) NH$_3$, MeOH.

FIGURE 7. SYNTHESIS OF 5-THIENYL-SUBSTITUTED 2'-DEOXYURIDINE ANALOGUES
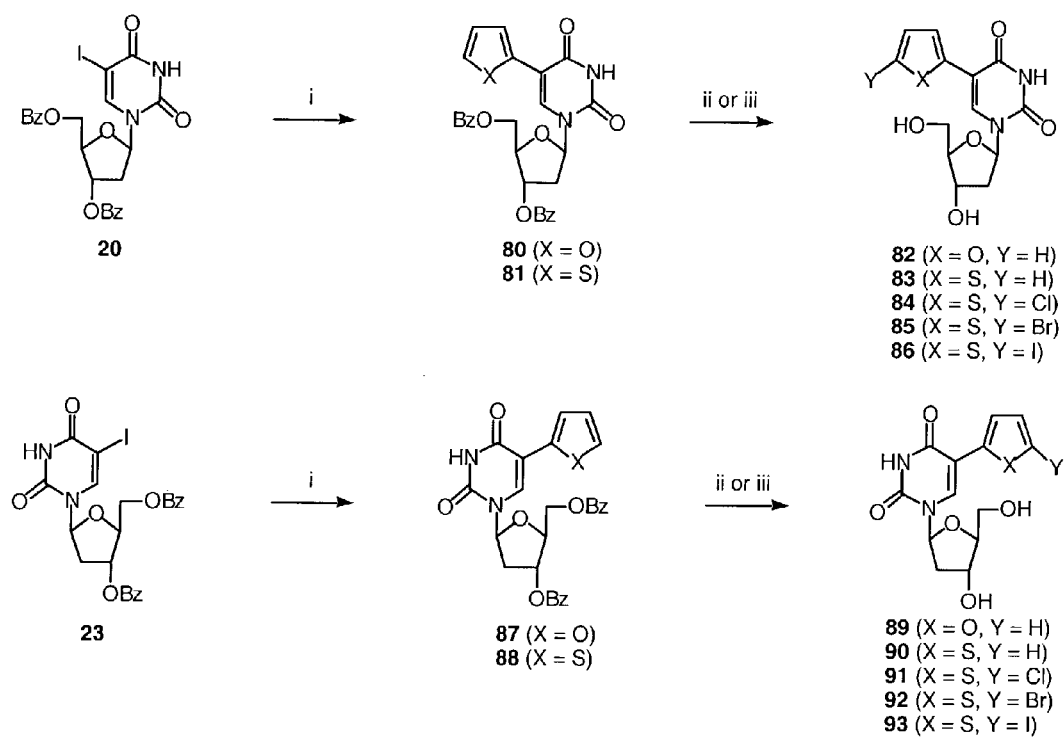
Keys: (i) Pd$_2$dba$_3$, NMP, tri(2-furyl)phosphine, 2-(tributylstannyl)furan or 2-(tributylstannyl)thiophene; (ii) a) NCS/pyr. or Br$_2$-CCl$_4$/CHCl$_3$ or I$_2$/CAN/MeCN; b) NH$_3$-MeOH; (iii) NH$_3$-MeOH.

FIGURE 8. SYNTHESIS OF 5-SUBSTITUTED DIOXOLANE NUCLEOSIDES
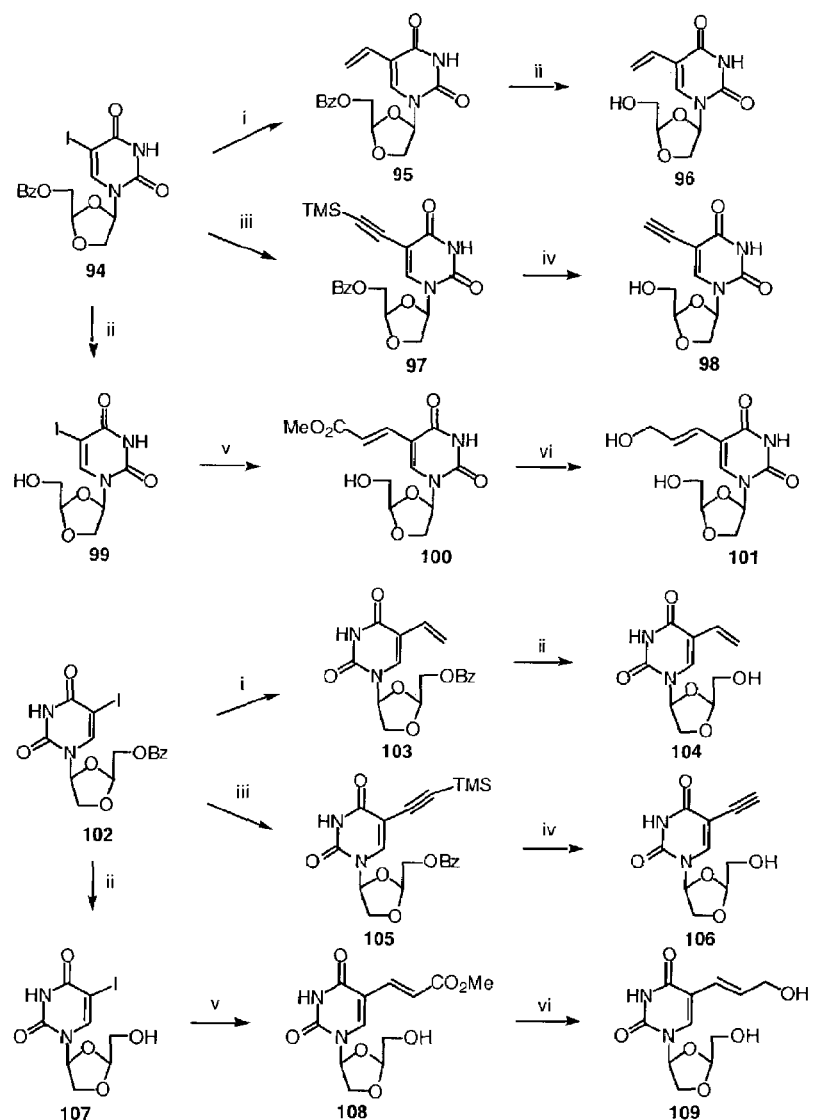
Keys: (i) Pd$_2$dBa$_3$, NMP, Bu$_3$SnCH=CH$_2$, tri(2-furyl)phosphine; (ii) NH$_3$-MeOH; (iii) trimethylsilyl acetylene, PdCl$_2$, Ph$_3$P, CuI, THF; (iv) a) TBAF, THF; b) NH$_3$-MeOH; (v) Pd(OAc)$_2$, Ph$_3$P, 1,4-dioxane, methyl acrylate; (vi) DIBALH, toluene, -78 °C.

FIGURE 9. SYNTHESIS OF 5-HETEROARYL DIOXOLANE NUCLEOSIDES
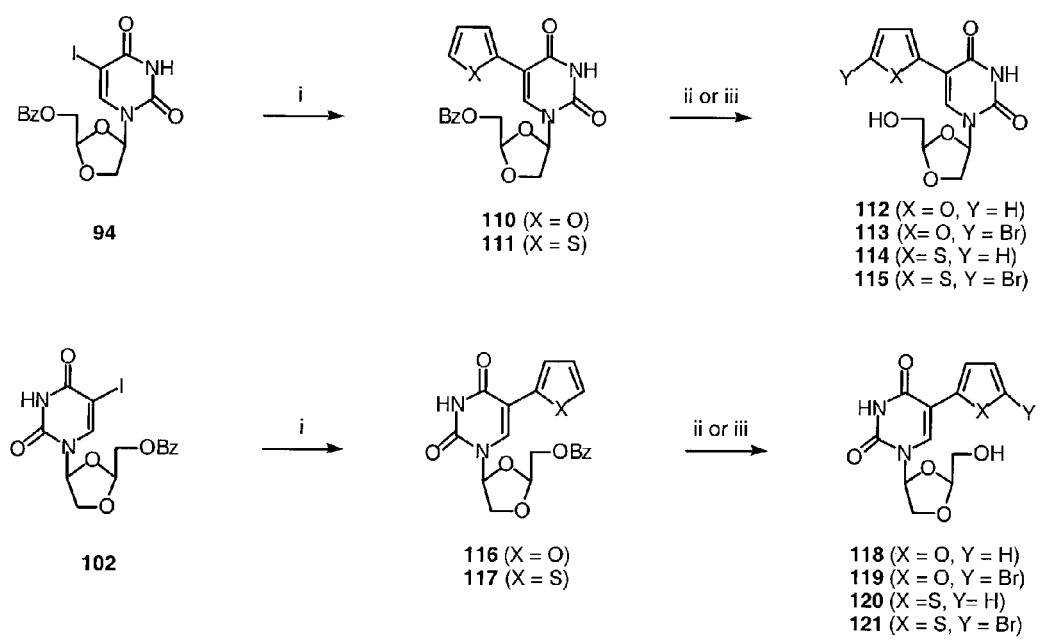
Keys: (i) $Pd_2dba_3$, NMP, tri(2-furyl)phosphine, 2-(tributylstannyl)furan or 2-(tributylstannyl)thiophene; (ii) a) NCS/pyr. or $Br_2$-$CCl_4$/$CHCl_3$ or $I_2$/CAN/MeCN; b) $NH_3$-MeOH; (iii) $NH_3$-MeOH.

FIGURE 10. SYNTHESIS OF 5-SUBSTITUTED DEOXYNUCLEOSIDES
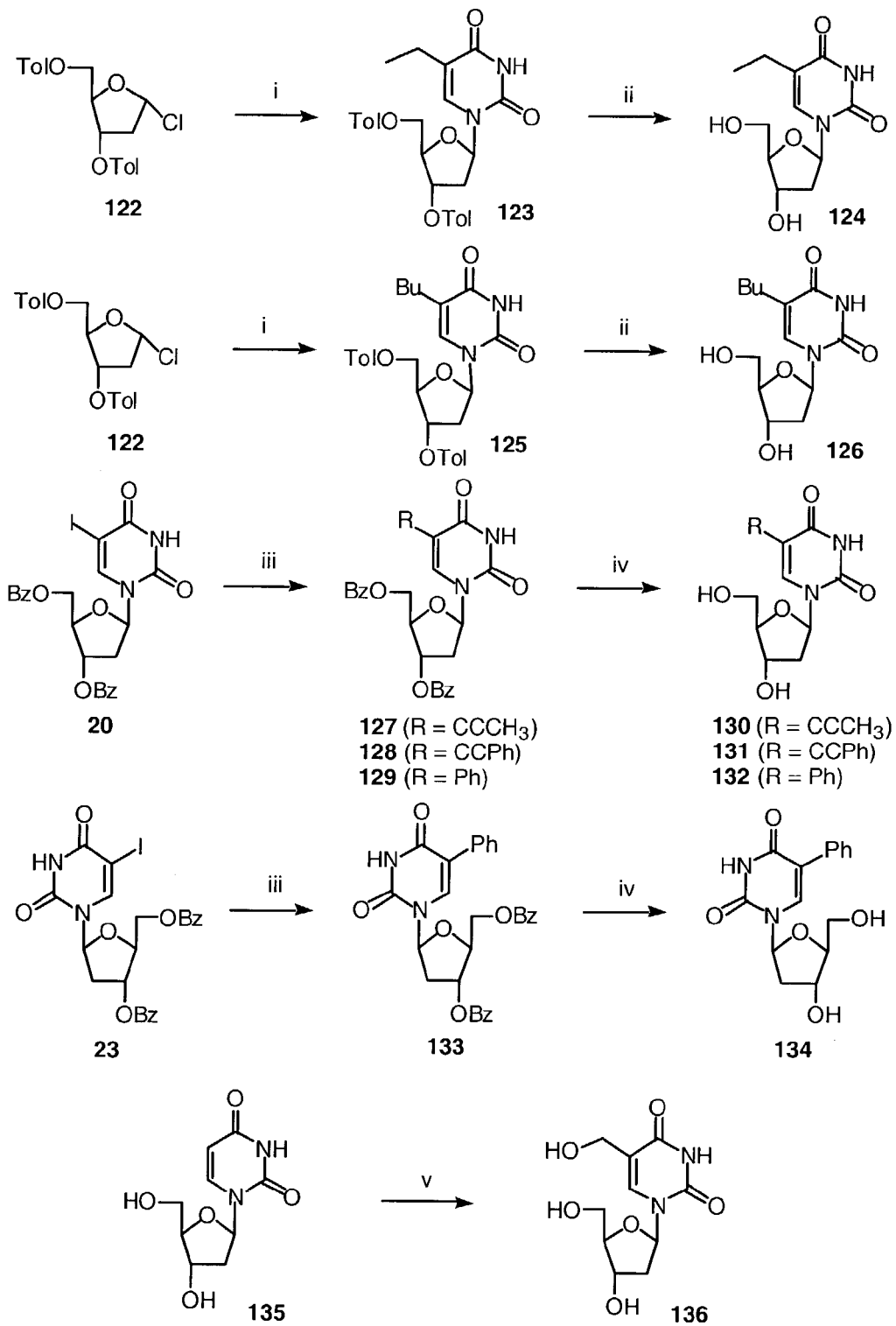
Keys: i. CHCl₃, persilylated 5-ethyluracil or 5-butyluracil; ii. NaOMe, MeOH; iii. Pd₂dba₃, NMP, tri(2-furyl)phosphine, tributyl(1-propynyl)tin or tributyl(phenylethynyl)tin or tributyl(phenyl)tin ; iv. NH₃, MeOH; v. (HCHO)ₙ, KOH, H₂O.

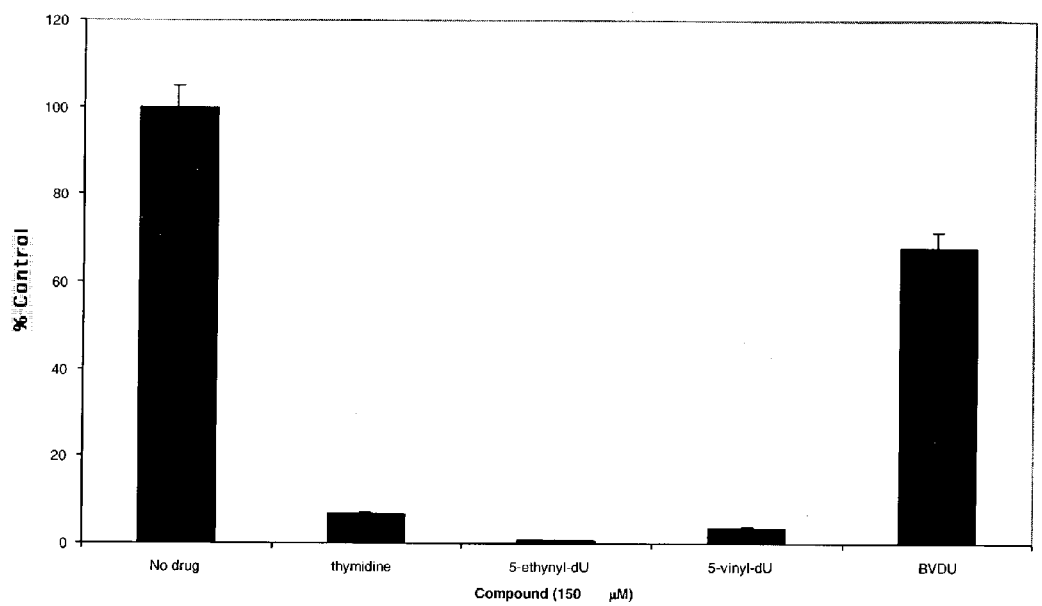
FIGURE 11. COMPETITION ASSAY: MEASUREMENT OF THE RELATIVE ABILITY OF NUCLEOSIDE ANALOGUES TO PREVENT PHOSPHORYLATION OF RADIO-LABELED THYMIDINE BY PURIFIED GST-EBV-TK FUSION PROTEIN FIGURE 12. COMPETITION ASSAY: MEASUREMENT OF THE RELATIVE ABILITY OF NUCLEOSIDE ANALOGUES TO PREVENT PHOSPHORYLATION OF RADIO-LABELED THYMIDINE IN LYSATES FROM CELLS EXPRESSING EBV-TK OR CELLS EXPRESSING ENDOGENOUS hTK-1
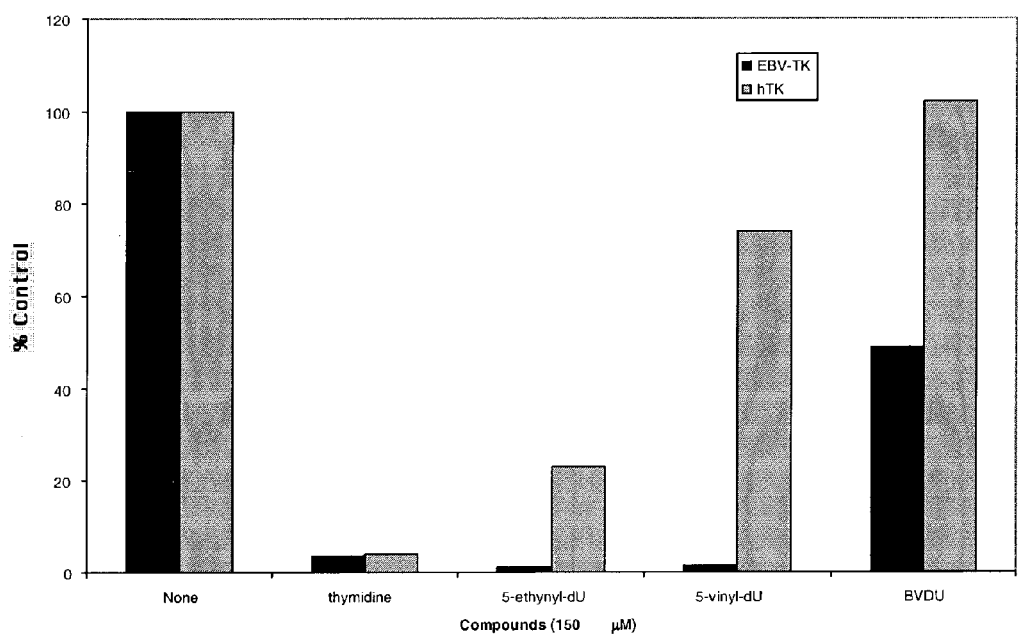

FIGURE 13. COLONY FORMATION ASSAY: EFFECT OF INCREASED CONCENTRATIONS OF 5-VINYL-dU ON COLONY FORMATION IN CELLS EXPRESSING
EBV-TK OR ENDOGENOUS hTK-1
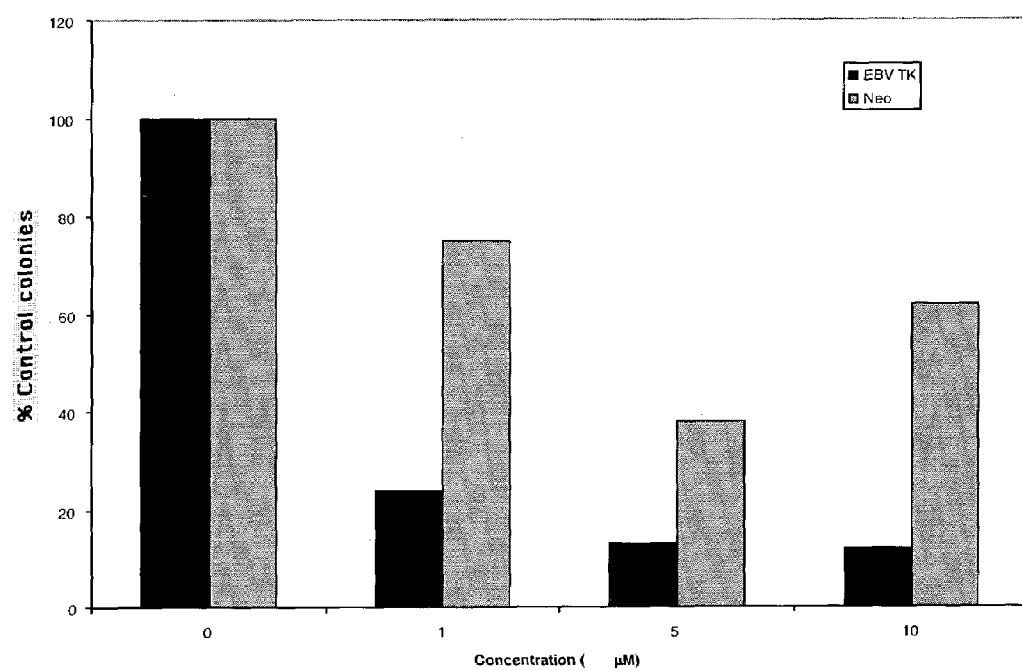

FIGURE 14. CYTOTOXICITY OF NUCLEOSIDES ON 143B CELLS AT 20 μM CONCENTRATION

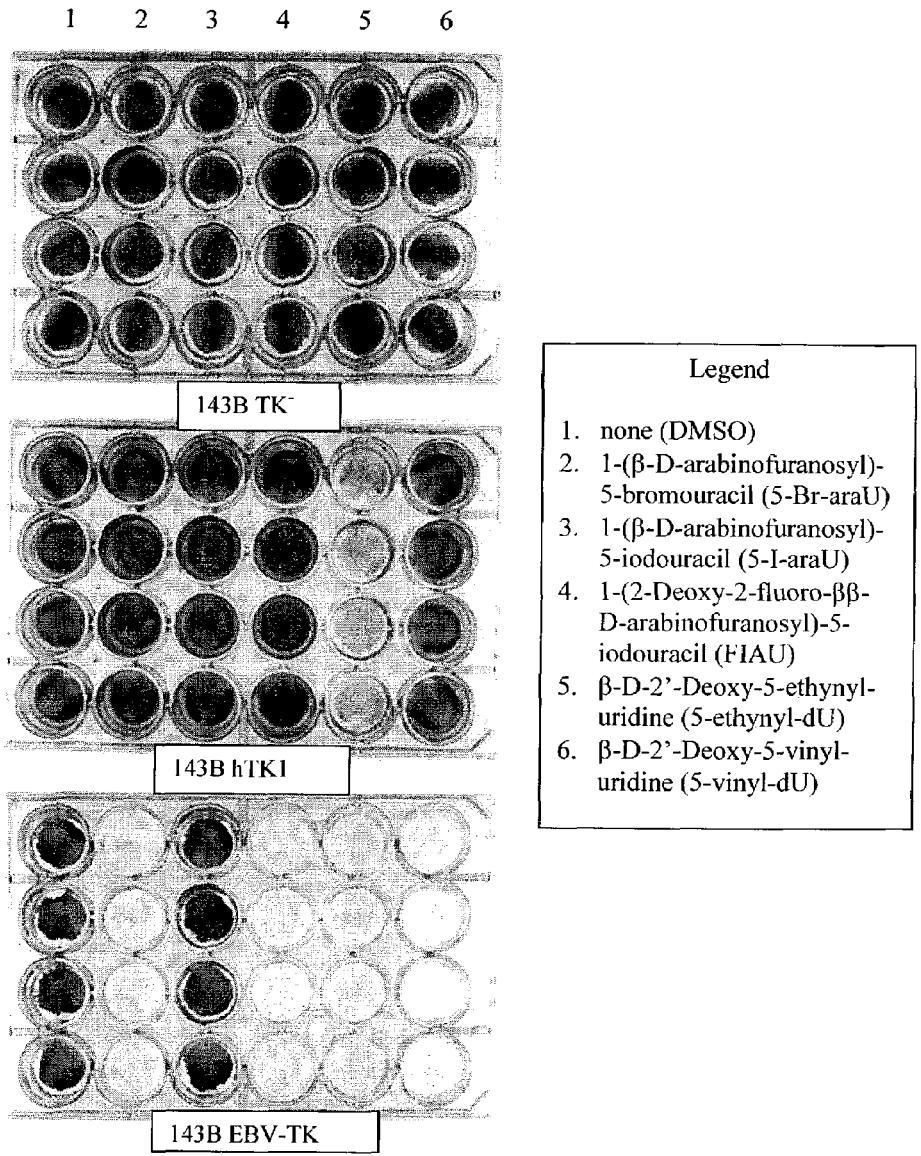

Legend 1. none (DMSO)
2. 1-(β-D-arabinofuranosyl)-5-bromouracil (5-Br-araU)
3. 1-(β-D-arabinofuranosyl)-5-iodouracil (5-I-araU)
4. 1-(2-Deoxy-2-fluoro-ββ-D-arabinofuranosyl)-5-iodouracil (FIAU)
5. β-D-2'-Deoxy-5-ethynyl-uridine (5-ethynyl-dU)
6. β-D-2'-Deoxy-5-vinyl-uridine (5-vinyl-dU)

Cells were split into 24-well plates at $10^5$ cells per well and cultured in media containing 20 μM of the indicated drug for 5 days. Cells were then fixed and stained with crystal violet as described in methods.

FIGURE 15. CYTOTOXICITY OF COMPOUNDS
ON 293 CELLS AND 293/EBV-TK
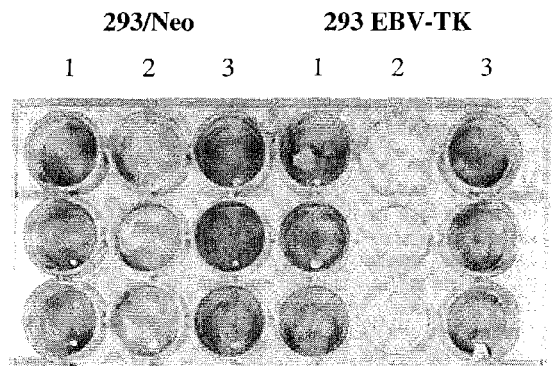
Cells were split into 24-well plates at $10^5$ cells per well and cultured in media containing 20 µM of the indicated drug for 5 days. Cells were then fixed and stained with crystal violet as described in methods.
Drugs
1. none (DMSO)
2. β-D-2'-Deoxy-5-vinyluridine (5-vinyl-dU)
3. 1-[[3-Hydroxy-2-bis(hydoxymethyl)propoxy]methyl]-5-fluorouracil FIGURE 16. CYTOTOXICITY OF 5-VINYL-dU ON 293NEO
CELLS OR 293/EBV-TK CELLS AT DIFFERENT CONCENTRATIONS (μM)
ND    20μM  10μM  5μM    1μM  0.1μM of β-D-2'-deoxy-5-vinyluridine (5-vinyl-dU)
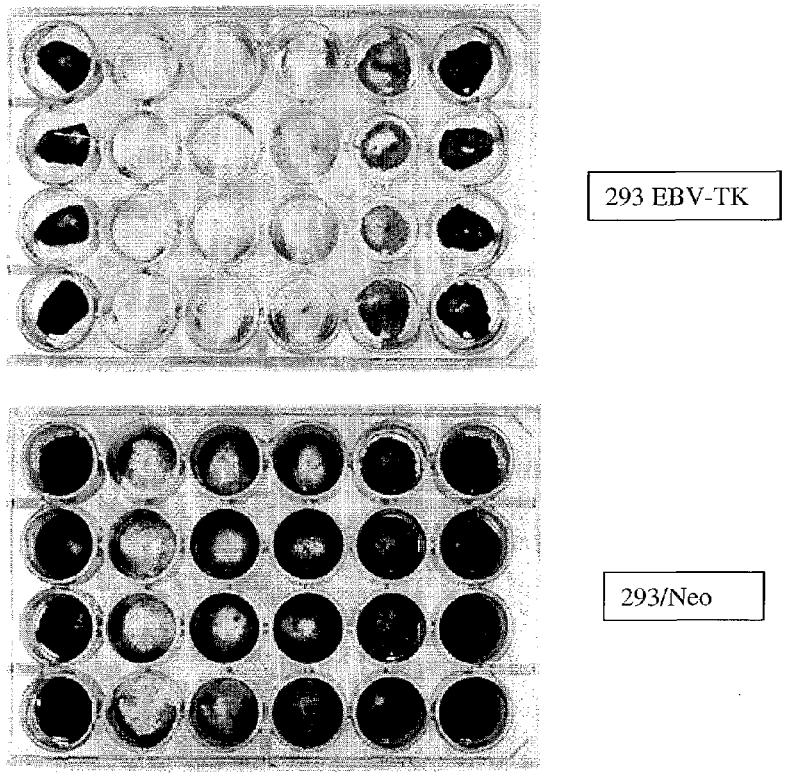
293 EBV-TK
293/Neo
Cells were split into 24-well plates at $10^5$ cells per well and cultured in the presence of the indicated amount of 5-vinyl-dU for 5 days. Cells were then fixed and stained with crystal violet as described in methods.

FIGURE 17. CYTOTOXICITY OF MODIFIED NUCLEOSIDES ON 143B VERSUS 143 EBV-TK CELLS AFTER 5 DAYS TREATMENT AT 20 μM.
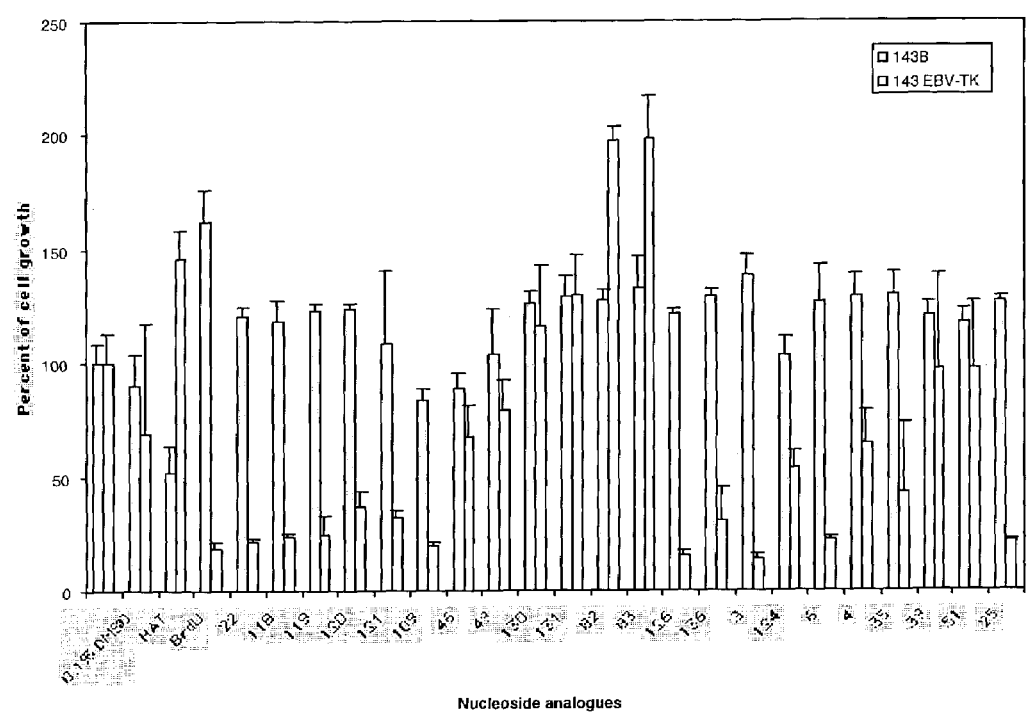

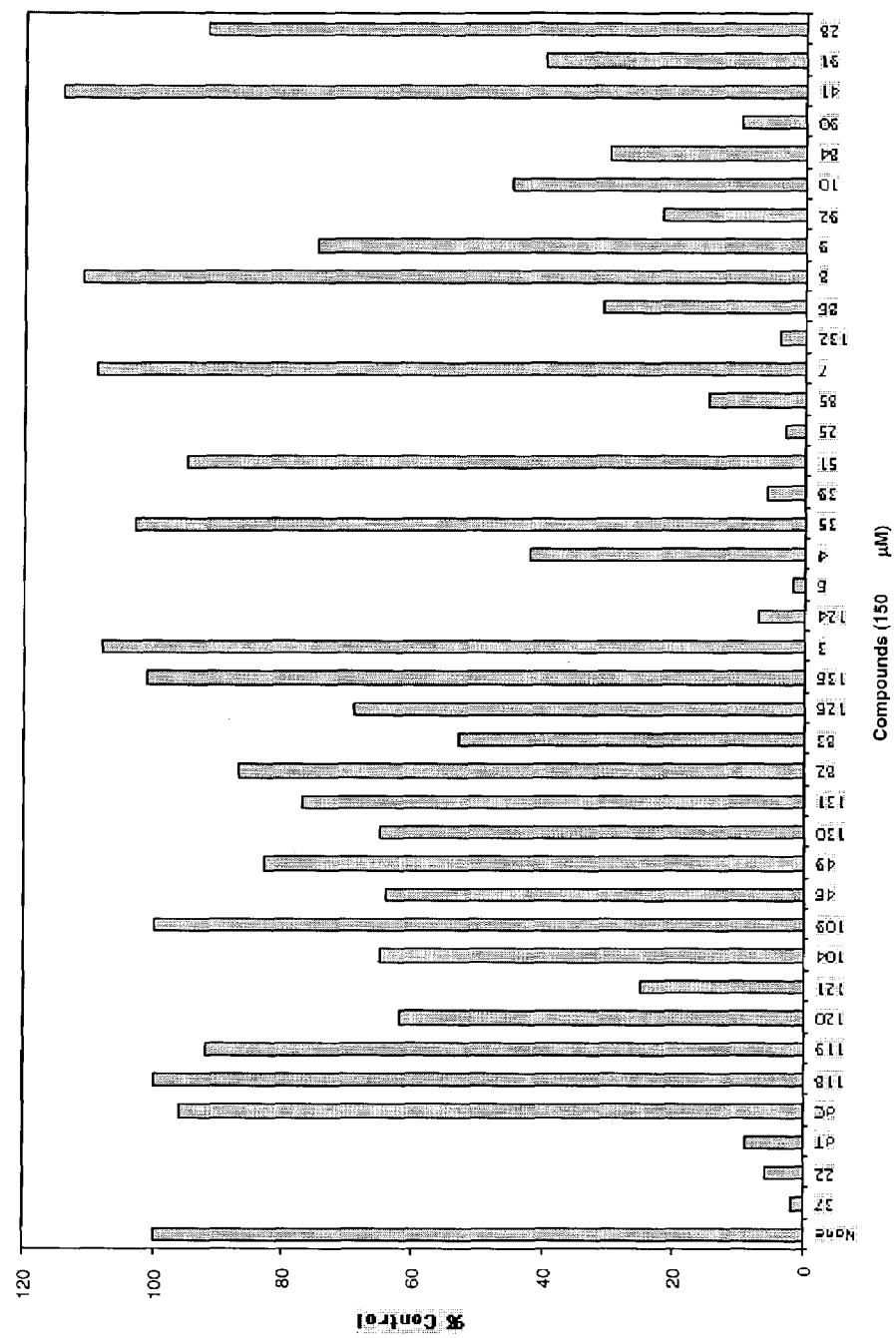
FIGURE 18. COMPETITION ASSAY BETWEEN NUCLEOSIDE ANALOGUES AND RADIO-LABELED THYMIDINE WITH PURIFIED GST-EBV TK FUSION PROTEIN

TREATMENT OF EBV AND KHSV INFECTION

This application claims priority to U.S. provisional application No. 60/345,130, filed on Dec. 20, 2001.

FIELD OF THE INVENTION

The present invention is directed to (i) compounds, compositions and methods for the treatment or prophylaxis of abnormal cellular proliferation in Epstein-Barr virus (EBV) or Kaposi's sarcoma-associated herpes ("KHSV") positive cells; (ii) treatment of EBV- or KHSV-infections; and (iii) gene therapy treatment of abnormally proliferating cells that are EBV and KHSV negative.

BACKGROUND OF THE INVENTION

Epstein-Barr virus (EBV) was discovered in 1964 in the neoplastic B cells of a patient with Burkitt's lymphoma. EBV thus became the first candidate for a human tumor virus. Early studies indicated the viral genome was present in two endemic tumors, Burkitt's lymphoma (equatorial Africa) and nasopharyngeal carcinoma (Southern China and coastal Asia) (Henle W. & Henle G. (1985) Epstein-Barr virus and human malignancies, *Adv. Viral Oncol.* 5, 201). By the late 1970s, it became evident that EBV plays a role in the development of B-cell lymphoproliferative disorders/lymphomas (BLPD) in T-cell immunocompromised patients, including solid organ and bone marrow transplant recipients, patients infected with HIV and children with congenital immunodeficiencies (Hanto D. W., Gajl-Peczalska K. J., Frizzera G., Arthur D. C., Balfour H. H., Jr., McClain K. (1983) EBV-induced polyclonal and monoclonal B-cell lymphoproliferative diseases occurring after renal transplantation. Clinical, pathologic, and virologic findings and implications for therapy, *Ann Surg.* 198, 356–69). In recent years, EBV has been identified in the hematopoietic tumor cells of approximately 50% of cases of Hodgkins disease, a large number of T-lymphomas and rare NK/monocytoid/dendritic cell malignancies, as well as in sporadic epithelial carcinomas (including in particular gastric carcinoma, and possibly aggressive breast carcinomas) (Kieff E. (2001) EBV and its Replication, In: *Fields Virology.* Phila., Pa.: Lippincott-Raven; p. 2511–2573; Pagano J. S. (1999) EBV: the first human tumor virus and its role in cancer, *Proc. Assoc. Am. Physicians,* 111, 573–580; Bonnet M., Guinebretiere J. M., Kremmer E., Grunewald V., Benhamou E., Contesso G. (1999) Detection of EBV in invasive breast cancers, *J. Natl. Cancer Inst.* 91, 1376–1381). An association with leiomyosarcomas in immunodeficient patents has also been found (Rogatsch H., Bonatti H., Menet A., Larcher C., Feichtinger H., Dirnhofer S. (2000) EBV-associated multicentric leiomyosarcoma in an adult patient after heart transplantation: case report and review of the literature. *Am. J. Surg. Path.* 24, 614–21). Several lines of evidence indicate that viral gene products contribute to multi-step tumorigenesis in these diverse neoplasms.

EBV is a member of the human herpesvirus family. Infection in childhood is usually asymptomatic; however, approximately 50% of individuals with delayed exposure develop a self-limited lymphoproliferative syndrome, acute infectious mononucleosis. Similar to other herpesviruses, EBV persists in a latent form for the life of the host. Serological surveys indicate that greater than 90% of the world population is infected with EBV (Henle W. & Henle G. (1979) Seroepidemiology of the virus, In: The Epstein-Barr Virus (Epstein M. A. & Achong B. G. eds), Springer Verlag, New York, pp. 61–73). The ubiquity of infection, coupled with increasing evidence for a broad role in virus-associated malignancies (in the immuno-compromised as well as the normal host) demonstrates a critical need to develop preventive and therapeutic strategies to limit EBV infection and the effects thereof.

Several approaches to prevent and treat the manifestations of EBV-associated malignancies are being investigated. These include generation of vaccines (for prevention, though one does not exist at this time), delivery of humoral and cell-based immune therapies, chemotherapy, gene therapy (for treatment) and antiviral drug therapy, based on decreasing EBV lytic replication in the hope that this will indirectly result in a decrease in the number of EBV-infected cells able to develop into tumors (for prophylaxis).

Treatment of EBV and EBV-Associated Diseases

Immunomodulatory agents such as α- and γ-interferons, IVIG, retinoic acid, and others, either alone or in combination have been used to treat B-cell lymphoproliferative disease (BLPD), with variable success. However, responses have not been observed in other EBV-associated tumors (Shapiro R. S., Chauvenet A., McGuire W., Pearson A., Craft A. W., McGlave P., Filipovich A. (1988) Treatment of B-cell lymphoproliferative disorders with interferon alfa and intravenous gamma globulin, *N. Engl. J. Med.* 318, 1334; Pomponi F., Cariati R., Zancai P., De Paoli P., Rizzo, S., Tedeschi, R. M. (1996) Retinoids irreversibly inhibit in vitro growth of EBV-immortalized B lymphocytes, *Blood,* 88, 3147–3159).

The use of complement-fixing, anti-B cell monoclonal antibodies to treat EBV-infected B-lymphomas previously achieved limited success. A B-cell-directed Mab to CD20 (Rituximab) is now commercially available and has achieved the greatest success in treatment of BLPD/lymphoma to date. However, anaphylactic reactions have limited therapy in some cases and not all B-cell tumors bear CD20. Moreover, Rituximab confers no specificity for the virus-infected cell, causing long-term impairment of new humoral immune responses; Rituximab also has no efficacy for a spectrum of non-B-cell, EBV-associated diseases (Fischer A., Blanche S., Le Bidois J., Bordigoni P., Garnier J. L., Niaudet P. (1991) Anti-B-cell monoclonal antibodies in the treatment of severe B-cell lymphoproliferative syndrome following bone marrow and organ transplantation, *N. Engl. J. Med.* 324, 1451–1456; Milpied N., Vasseur B., Parquet N., Gamier J. L., Antoine C., Quartier P. (2000) Humanized anti-CD20 monoclonal antibody (Rituximab) in post transplant B-lymphoproliferative disorder: a retrospective analysis on 32 patients, *Ann. Oncol.* 11(Suppl 1), 113–116).

Individual cell-based immune strategies are promising, but they incur a risk of graft-versus-host-disease and of transmission of pathogens during ex vivo propagation/preparation of cells, and will be expensive (Papadopoulos E. B., Ladanyi M., Emanuel D., Mackinnon S., Boulad F., Carabasi M. H. (1994) Infusions of donor leukocytes to treat EBV-associated lymphoproliferative disorders after allogeneic BMT, *N. Engl. J. Med.* 330, 1185–1191; Aguilar L. K., Rooney C. M., Heslop H. E. (1999) Lymphoproliferative disorders involving EBV after hemopoietic stem cell transplantation, *Curr. Opin. Oncol.* 11, 96–101).

Gene therapy strategies to introduce novel compounds that inhibit EBV oncoproteins or that inhibit cellular genes that are critical for virus-associated oncogenesis or that introduce cytotoxic gene products (such as the HSV1-TK gene into EBV-infected tumor cells followed by ganciclovir therapy) are under study. All are in early development and suffer from standard problems of delivery to the appropriate tumor site.

In the chemotherapy field, currently there are few or no clinically effective anti-EBV agents that are without undesirable side effects. Although several drug candidates have been shown to be effective against EBV replication in cell culture, their clinical application has been restricted by their lack of effect on the course of latency associated disease, because all of these antiviral agents target only EBV replication.

The greatest challenge in EBV therapy is the latent infection. There are no drugs, licensed or even experimental, regardless of mechanism of action, that have shown any specific effect on latent EBV or other gamma herpesvirus infection (Lin, J. C. (1999) Antiviral therapy for Epstein-Barr virus: the challenge ahead, *Recent Res. Develop. Antimicrob. Agents and Chemother.* 3, 191–223; Pagano J. S. (1995) Epstein-Barr virus: therapy of active and latent infection, in *Antiviral Chemotherapy* (eds. Jeffries & De Clercq), John Wiley & Sons, Chichester, pp. 155–195).

Several compounds have been shown to have activity against EBV replication in culture at concentrations nontoxic to cell growth. These include acyclovir (ACV), ganciclovir (DHPG), pencyclovir, D-FMAU and its analogs, 5-bromovinyl dUrd, phosphonoformate and phosphorothioate oligonucleotides. See Lin et al., Antimicrob. Agents Chemo. 32:265–267 (1988); Lin et al., Antimicrob. Agents Chemo., 32:1068–1072 (1988); Cheng et al., Proc. Natl., Acad. Sci. USA, 80:2767–2770(1983); Datta et al., Proc. Natl., Acad. Sci. USA, 77:5163–5166 (1980); Datta et al., Virol., 114:52–59 (1981); Lin et al., Antimicrob. Agents & Chemo., 31:1431–1433 (1987); Olka & Calendar, Virol. 104:219–223 (1980); Lin et al., J. Virol., 50:50–55 (1984); Yao et al., Antimicrob. Agents & Chemo. 37:1420–1425 (1993) and Yao et al., Biochem. Pharm., 51:941–947 (1966).

U.S. Pat. Nos. 5,565,438, 5,567,688 and 5,587,362 (Chu et al.) disclose the use of 2'-fluoro-5-methyl-β-L-arabino-furanolyluridine (L-FMAU) for the treatment of hepatitis B and Epstein-Barr virus.

WO96/13512 (Genencor International, Inc. and Lipitek, Inc.) discloses the preparation of L-ribofuranosyl nucleosides as antitumor agents and virucides.

Tsai et al. in Biochem. Pharmacol. 1994, 48(7), 1477–81, disclose the effect of anti-HIV agents 2'-β-D-F-2',3'-dideoxynucleoside analogs on the cellular content of mitochondrial DNA and lactate production.

WO 96/40164 and WO 95/07287 (Emory University, UAB Research Foundation, and the Centre National de la Recherche Scientifique) disclose several β-L-2',3'-dideoxynucleosides for the treatment of hepatitis B virus and HIV, respectively.

Novirio Pharmaceuticals, Ltd. (WO 00/09531) disclose 2'-deoxy-β-L-erythropento-furanonucleosides (also referred to as β-L-dN or β-L-2'-dN), including β-L-deoxyribothymidine (β-L-dT) and β-L-deoxyribouridine (β-L-dU).

U.S. Pat. Nos. 5,792,773, 6,022,876 and 6,274,589 (Yale University and The University of Georgia Research Foundation, Inc.) disclose certain β-L dioxolanyl uracil-based nucleosides for the treatment of EBV. The compounds preferably have a 5-halosubstituted uracil base, and reportedly exhibit unexpectedly high activity against EBV, Varicella-Zoster virus (VZV) and Kaposi's Sarcoma virus (HV-8).

Gene Therapy

In studies of gene therapy for cancer, researchers are working to recruit the immune response to fight the disease or to make the cancer cells more sensitive to ablative treatment, such as chemotherapy. Some of the gene therapy techniques under study include:

Substitution of a "working" copy of a gene for an inactive or defective gene. For example, this technique could be used to restore the ability of a defective gene (such as mutant p53) to suppress or block the development of cancer cells.

Introduction of a "survival gene," such as the multidrug resistance (MDR) gene into stem cells (cells in the bone marrow that produce blood cells). The MDR gene is used to make the stem cells more resistant to the side effects of the high doses of anticancer drugs.

Injection of cancer cells with a gene that makes them more susceptible to treatment with an anticancer drug. Scientists hope that treatment with the drug will kill only the cells that contain the drug-sensitive gene. This is known as suicide gene therapy.

Suicide gene therapy is defined as the transduction of a gene that converts a prodrug into a toxic substance. Independently, the gene product and the prodrug are nontoxic. Two such systems have been widely investigated: the *Escherichia coli* cytosine deaminase (CD) gene plus 5-fluorocytosine (5-FC) and the herpes simplex virus thymidine kinase gene (HSV1-TK) plus ganciclovir (GCV).

The CD gene product converts 5-FC to the chemotherapeutic agent, 5-fluorouracil (5-FU) (Huber Be Austin, E A Good, S S, et al. (1993) In vivo antitumor activity of 5-fluorocytosine on human colorectal carcinoma cells genetically modified to express cytosine deaminase. Cancer Res. 53:4619–4626) and has been studied primarily as a treatment for hepatic metastases of gastrointestinal tumors, for which 5-FU is commonly used. A significant bystander effect is active through production of locally high levels of freely diffusible 5-FU (Trinh Q T, Austin E A, Murray D M, et al., Enzyme/prodrug gene therapy: Comparison of cytosine deaminase/5-fluorcytosine versus thymidine kinase/ganciclovir enzyme/prodrug systems in a human colorectal carcinoma cell line. Cancer Res 55:4808–4812, 1995). Systemic therapy with 5-FC results in growth suppression of CD-transduced tumors, whereas little growth inhibition is achieved in the same tumors with high doses of systemic 5-FU (Huber B E, Austin E A, Good S S et al. (1993) In vivo antitumor activity of 5-fluorocytosine on human colorectal carcinoma cells genetically modified to express cytosine deaminase. Cancer Res. 53:4619–4626). No systemic growth suppression was seen in non-transduced tumors growing in the same animals, indicating the lack of serum 5-FU levels sufficient for antitumor activity. Interestingly, other investigators have noted that successful treatment of CD-transduced tumors with 5-FC can result in activity against challenge tumors (Mullen C A, Kilstrup M, Blaese R M (1992) Transfer of the bacterial gene for cytosine deaminase to mammalian cells confers lethal sensitivity to 5-fluorocytosine: a negative selection system. Proc. Natl. Acad. Sci. USA 89:33–37). Depletion of CD8+ T-cells or granulocytes abrogates the effects of CD plus 5-FC (Consalvo M., Mullen C. A., Modesti A., Musiani P., Allione A., Cavallo F., Giovarelli M., Forni G. (1995) 5-Fluorocytosine-induced eradication of murine adenocarcinomas engineered to express the cytosine deaminase suicide gene requires host immune competence and leaves an efficient memory. J. Immunol. 154, 5302–5312), indicating that inadvertent stimulation of immunological activity in this system may further enhance the efficacy of this approach.

Strategies for treating liver metastases have focused on regional delivery of the CD gene into areas surrounding metastases (Ohwada A, Hirschowitz E A, Crystal R G (1996) Regional delivery of an adenovirus vector containing the *Escherichia coli* cytosine deaminase gene to provide local activation of 5-fluorocytosine to suppress the growth of colon carcinoma metastatic to liver. Hum. Gene Ther. 7:1567–1576). Further refinements for systemic gene delivery are being explored through the use of tissue-specific promoters, such as carcinoembryonic antigen (CEA) or alfetoprotein genes, for targeting gene expression to liver tumor cells after hepatic-artery infusion of the CD vector (Richards C A, Austin E A, Huber B E (1995) Transcriptional regulatory sequences of carcinoembryonic antigen: identification and use with cytosine deaminase for tumor-specific gene therapy. Hum. Gene Ther. 6:881–893; Kanai F, Lan K H, Shiratori Y, et al. (1997) In vivo gene therapy for alpha-fetoprotein-producing hepatocellular carcinoma by adenovirus-mediated transfer of cytosine deaminase gene. Cancer Res. 57:461–465).

The selective toxicity of ganciclovir (GCV) for cells expressing HSV-1-TK has been utilized similarly to promote tumor killing in a gene therapy model. In an original report (Culver K. W., Ram Z., Wallbridge S., Ishii H., Oldfield E. H., Blaese R. M. (1992) In vivo gene transfer with retroviral vector-producer cells for treatment of experimental brain tumors, *Science*, 256, 1550–1552), rapidly dividing murine glioma cells were infected in vivo with an amphotropic retrovirus vector containing HSV-TK. The animals were then treated with GCV. This resulted in the death of tumor cells expressing the viral TK, but spared adjacent normal cells that replicated too slowly for efficient retroviral infection. Because of the so-called bystander effects, this treatment is effective in destroying the tumor cells that contain as few as 10% TK-expressing cells. Adjacent cells that replicate rapidly also take up the cytotoxic phosphorylated nucleosides.

HSV1-TK phosphorylates GCV to GCV-monophosphate (GCV-MP) in a rate-limiting step, which can be further converted to a nucleotide analogue that inhibits DNA synthesis via cellular enzymes (Moolten F. L. (1986) Tumor chemosensitivity conferred by inserted herpes thymidine kinase genes: paradigm for a prospective cancer control strategy. Cancer Res. 46, 5276–5281). This metabolic change causes a significant by-stander effect through several mechanisms: gap junctions transport non-diffusible phosphorylated GCV to non-transduced cells; non-transduced cells endocytose debris containing phosphorylated GCV from dying cells; and an induced immune response leads to tumor killing (Vile R. G., Nelson J. A., Castleden S., Chong H., Hart I. R. (1994) Systemic gene therapy of murine melanoma using tissue specific expression of the HSVtk gene involves an immune component. Cancer Res. 54, 6228–6234; Elshami A A, Saavedra A, Zhang H, et al. Gap junction plays a role in the "bystander effect" of the herpes simplex virus thymidine kinase/ganciclovir system in vitro. Gene Ther 1996; 3:85–92; Hamel W, Magnelli L, Chiarugi V P, Israel M A. Herpes simplex virus thymidine kinase/ganciclovir-mediated apoptotic death of bystander cells. Cancer Res 1996 56:2697–2702; Mesnil M.; Piccoli C.; Tiraby G., Willecke K.; Yamasaki H. Bystander killing of cancer cells by herpes-simplex virus thymidine kinase gene is mediated by connexins. Proc. Natl. Acad. Sci. USA 93, 1831–1835; 1996). This type of gene therapy has been explored for a variety of cancers, including localized brain tumors (Culver K W, Ram Z, Walbridge S, Ishii H, Oldfield E H, Balese, R M 1992. In vivo gene transfer with retroviral vector producer cells for treatment of experimental brain tumors. *Science* 256:1550–1552; Barba D. Hardin J, Sadelain M, et al. Development of anti-tumor immunity following thymidine kinase-mediated killing of experimental brain tumors. Proc Natl Acad Sci USA 1994; 91, 4348–52; Chen S, Shine H D, Goodman J C, Grossman R G, Woo S L C 1994. Gene therapy for brain tumors: regression of experimental gliomas by adenovirus-mediated gene transfer in vivo. *Proc Natl Acad Sci USA* 91: 3054–3057) and mesotheliomas (Elshami A A, Saavedra A, Zhang H, et al. Gap junction plays a role in the "bystander effect" of the herpes simplex virus thymidine kinase/ganciclovir system in vitro. Gene Ther 1996; 3:85–92), liver metastases (Caruso M., Panis Y., Gagandeep S., Houssin D., Salzmann J. L., Klatzmann D. Regression of established macroscopic liver metastases after in-situ transduction of a suicide gene. Proc. Natl. Acad. Sci. USA 90, 7024–7028, (1993)), and peritoneal-based metastases (Tong X W, Block A, Chen S H, Woo S L C, Kieback D G. Adenovirus-mediated thymidine kinase gene transduction in human epithelial ovarian cancer cell lines followed by exposure to ganciclovir. Anticancer Res 1996 16, 1611–1617; Yee D, McGuire S E, Brunner N, Kozelsky T W, Allred D C, Chen S H, Woo S L C. Adenovirus-mediated gene transfer of herpes simplex virus thymidine kinase in an ascites model of human breast cancer. Hum Gene Ther 1996 7, 1251–1257). There have been more than 35 clinical trials using this approach for human cancers worldwide. Although the growth-suppressive activities of HSV-TK plus GCV are significant, cure rates thus far are low, as in situ transduction (gene delivery) remains inadequate and the bystander effect is variable. Notably, both the CD and HSV-TK systems, and p53 gene therapy, additionally sensitize cancer cells to radiation, suggesting possible combination therapies to control advanced tumors (Kim J H, Kim S H, Kolozsvary A, Brown S L, Lim O B, Freytag S O. Selective enhancement of radiation response of herpes simplex virus thymidine kinase transduced 9L gliosarcoma cells in vitro and in vivo by antiviral agents. Int J Radiat Oncol Biol Phys 33: 861–868, 1995; Khil M. S.; Kim J. H., Mullein C. A., Kim S. H., Freytag S. O. Radiosensitization by 5-fluorocytosine of human colorectal carcinoma cells in culture transduced with cytosine deaminase gene. Clinical Cancer Res. 2, 53–57 (1996)).

Use of HSV-TK plus GCV for the treatment of metastatic disease presents several problems. Treatment of tumors with HSV-TK suppresses growth of tumors derived from challenge injections of the parental cell line, indicating the induction of systemic anti-tumor activity in some models (Barba D. Hardin J, Sadelain M et al. Development of anti-tumor immunity following thymidine kinase-mediated killing of experimental brain tumors. Proc Natl Acad Sci USA 1994 91, 4348–52; Vile R. G., Nelson J. A., Castleden S., Chong H., Hart I. R. Systemic gene-therapy of murine melanoma using tissue-specific expression of the HSVtk gene involves an immune component. Cancer Res. 54, 6228–6234; 1994). Some evidence exists that this suppression is mediated by immune cells (Vile R. G., Nelson J. A., Castleden S., Chong H., Hart I. R. Systemic gene-therapy of murine melanoma using tissue-specific expression of the HSVtk gene involves an immune component. Cancer Res. 54, 6228–6234; 1994; Yamamoto S., Suzuki S., Hoshino A., Akimoto M., Shimada T. (1997) Herpes simplex virus thymidine kinase/ganciclovir-mediated killing of tumor cells induces tumor-specific cytotoxic T-cells in mice. *Cancer Gene Ther.* 4, 91–96), but the significance and generality of these observations are largely unknown. Furthermore, systemic delivery of HSV-tk to target metastatic lesions through intravenous (Vile R. G., Nelson J. A., Castleden S., Chong H., Hart I. R. Systemic gene-therapy of murine melanoma using tissue-specific expression of the HSVtk gene involves an immune component. Cancer Res. 54, 6228–6234; 1994) or peritoneal (Tong X W, Block A, Chen S H, Woo S L, Kieback D G. Adenovirus-mediated thymidine kinase gene transduction in human epithelial ovarian cancer cell lines followed by exposure to ganciclovir. Anticancer Res 1996 16: 1611–1617; Yee D, McGuire S E, Brunner N, Kozelsky T W, Allred D C, Chen S H, Woo S L. Adenovirus-mediated gene transfer of herpes simplex virus thymidine kinase in an ascites model of human breast cancer. Hum Gene Ther 1996; 7, 1251–1257) routes may lead to significant liver injury (Yee D, McGuire S E, Brunner N, Kozelsky T W, Allred D C, Chen S H, Woo S L C. Adenovirus-mediated gene transfer of herpes simplex virus thymidine kinase in an ascites model of human breast cancer. Hum Gene Ther 1996; 7, 1251–1257; Brand K., Arnold W., Bartels T., Lieber A., Kay M. A., Strauss M., Dorken B. Liver-associated toxicity of the HSV-tk/GCV approach and adenoviral vectors. Cancer Gene Therapy 4, 9–16; 1997; Qian C, Idoate M, Bilbao R, Sangro B, Bruna O. Vazquez J et al. Gene transfer and therapy with adenoviral vector in rats with diethyInitrosamine-induced hepatocellular carcinoma. Hum Gene Ther 1997; 8, 349–358); tissue-specific vectors may be required for safe systemic delivery of this gene.

Epstein Barr Virus Thymidine Kinase (EBV-TK)

EBV-associated diseases are primarily manifest as virus-infected tumors in which the viral genome is present, however, infection is latent and few EBV genes are expressed. Increased levels of EBV lytic replication have been observed in the setting of acute infectious mononucleosis, a usually self-limited lymphoproliferative disorder and in oral hairy leukoplakia, a lytic disease of the oral cavity that occurs primarily in patients with AIDS. Increased levels of EBV lytic replication have been observed in the blood of immunocompromised patients and correlates with the subsequent development of lymphoproliferative disorders in these patients. There is no standard therapy for any of these conditions.

EBV encodes a thymidine kinase (TK), which is strictly a kinase with the capacity to phosphorylate thymidine and a range of thymidine analogs that is localized to the BamHI X fragment of the genome (Tung P. P. & Summers W. C. (1994) Substrate specificity of Epstein-Barr virus thymidine kinase. Antimicrob. Agents Chemother. 38, 2175–79; Gustafson E. A., Chillemi A. C., Sage D. R., Fingeroth J. D. (1998) The Epstein-Barr virus thymidine kinase does not phosphorylate ganciclovir or acyclovir and demonstrates a narrow specificity compared to herpes simplex virus type 1 thymidine kinase. Antimicrob. Agents Chemother. 42, 2923–31). Although latently EBV-infected B-cells and EBV+ tumors do not routinely express EBV-TK, in vitro exposure of latently infected cells to the tumor promoter (12-O-tetradecanoylphorbol-13-acetate) PMA/TPA or to the polar organic compound sodium butyrate (NaB) results in modest induction of lytic replication (1%–40% of cells depending on the line) that is accompanied by EBV-TK expression (Stinchcobe T. & Clough W. (1985) EBV induces a unique pyrimidine 2'-deoxynucleoside kinase activity in superinfected and virus producer B cell lines. *Biochemistry,* 24, 2021–2033). In several EBV+ B-cell lines, the use of TPA and NaB together has been found to synergistically activate the lytic cycle (Anisimova E., Prachova K., Roubal J., Vonka V. (1984) Effects of n-butyrate and phorbol ester (TPA) on induction of EBV antigens and cell differentiation. *Arch. Virol.* 81, 223–237). Even when production of virus is minimal, EBV genes active during the lytic cycle are induced by drug treatment, suggesting that drug-induced gene expression is not identical to expression triggered in the course of a normal, productive infection. Although herpesvirus replication proceeds in a defined sequence, with synthesis of immediate early (IE) genes preceding early (E) and late (L) genes, artificial inducers of productive infection can alter the normal stoichiometry of viral gene expression. Induction is often abortive with IE, and E proteins synthesized in the absence of late proteins and virus assembly. In recent studies, NaB and arginine butyrate (ArgB) and related compounds have been administered to healthy adults and children without major side-effects (Daniel P., Brazier M., Cerutti I., Pieri F., Tardivel I., Desmet G. (1989) Pharmacokinetic study of butyric acid administered in vivo as sodium and arginine butyrate salts. *Clin. Chim. Acta* 181, 255–263; Perrine S. P., Ginder G. D., Faller D. V., Dover G. H., Ikuta T., Witkowska H. E. (1993) A short-term trial of butyrate to stimulate fetal globin-gene expression in beta-globin disorders. *N. Engl. J. Med.* 328, 81–86). ArgB is FDA approved to induce fetal hemoglobin and abort hemolytic crisis in children with sickle cell anemia and β-thalassemia (Perrine S. P., Ginder G. D., Faller D. V., Dover G. H., Ikuta T., Witkowska, H. E. (1993) A short-term trial of butyrate to stimulate fetal-globin-gene expression in the beta-globin disorders. *N. Engl. J. Med.* 328, 81–86). In addition, protein kinase C activators pharmacologically distinct from TPA, such as the bryostatins, which lack tumor-promoting activity, are currently in clinical trials for cancer patients (Prendiville J., Crowther D., Thatcher N., Woll P. J., Fox B. W., McGown A. (1993) A phase I study of intravenous bryostatin 1 in patients with advanced cancer. *Br. J. Cancer* 68, 418–424).

Related gammaherpesvirus HHV8 expresses a thymidine kinase with similar substrate specificity to Epstein Barr virus (Gustafson E A, Schinazi R F, Fingeroth J D (2000) Human herpesvirus 8 open reading frame 21 is a thymidine and thymidylate kinase of narrow substrate specificity that efficiently phosphorylates zidovudine but not ganciclovir. J. Virol. 74, 684–692)). This virus is currently referred to in the literature as KHSV. See also Moore S M, Cannon J S, Tanhehco Y C, Hamzeh F M, Ambinder R F. (2001) Induction of Epstein-Barr virus kinases to sensitize tumor cells to nucleoside analogues. *Antimicrob Agents Chemother,* 45(7): 2082–91; Ansari A, Emery V C. (1999) The U69 gene of human herpesvirus 6 encodes a protein kinase which can confer ganciclovir sensitivity to baculoviruses. *J Virol,* 73(4):3284–91; Cannon J S, Hamzeh F, Moore S, Nicholas J, Ambinder R F. (1999) Human herpesvirus 8-encoded thymidine kinase and phosphotransferase homologues confer sensitivity to ganciclovir. *J Virol,* 73(6):4786–93; and Emery V C, Griffiths P D. (2000) Prediction of cytomegalovirus load and resistance patterns after antiviral chemotherapy. *Proc Natl Acad Sci* 97(14): 8039–44.

Therefore, it is an object of the present invention to provide compounds, compositions and methods for the treatment or prophylaxis of a host, particularly a human patient or other host animal, infected with EBV (or the related gammaherpesvirus KHSV).

It is another object of the present invention to provide compounds, compositions and methods for the treatment or prophylaxis of a host, particularly a human patient or other host animal, suffering from a disease associated with the lytic replication of EBV (or the related gammaherpesvirus KHSV).

It is further another object of the present invention to provide compounds, compositions and methods for the treatment or prophylaxis of a host, particularly a human patient or other host animal, suffering from a disease associated with abnormally proliferating cells that are infected with EBV (or the related gammaherpesvirus KHSV).

It is another objective of the present invention to provide cell lines that can be used in gene therapy, in particular, cell lines transfected with EBV-TK, or the related gammaherpesvirus thymidine kinase (KHSV-TK).

It is a further objective of the present invention to provide compounds, compositions and methods for gene therapy of a host, particularly a human patient or other host animal exhibiting a cancer or infection related to Epstein Barr Virus.

Finally, it is an objective of the present invention to provide kits and assays to assess the effects of compounds and/or compositions in reducing abnormal cellular proliferation using transduced cell lines.

SUMMARY OF THE INVENTION

It has been found that certain 5-substituted uracil-nucleosides are selectively phosphorylated by EBV thymidine kinase and/or KHSV thymidine kinase, and are not substantially phophorylated by human cellular thymidine kinase. Therefore, based on this and other observations, several embodiments of the invention are provided.

(i) A method for the treatment of a host with an abnormal cellular proliferation or abnormal cell disorder, wherein the cell is EBV or KHSV positive, that includes administering an effective amount of one or a combination of the described 5-substituted uracil-nucleosides or its pharmaceutically acceptable salt or prodrug, optionally in a pharmaceutically acceptable carrier. In this embodiment, 5-substituted uracil-nucleosides that are substrates for the host cellular polymerase are selected. When the uracil nucleoside is administered to the cell, it is selectively phosphorylated by the viral thymidine kinase and then is incorporated into cellular DNA by the action of the cellular polymerase, which reduces or terminates the proliferation. This can initiate the cellular repair mechanism, resulting in apoptosis. In an alternative or additional embodiment, the uracil nucleoside may act as an inhibitor of thymidylate synthetase. This method can be used to treat any abnormal cellular proliferation or disorder, including tumor or cancer growth, in which the abnormal cell includes the EBV genome. Examples of diseases that can be treated Burkitt's lymphoma, nasopharyngeal carcinoma, any B-cell lymphoproliferative disorders/lymphoma (BLPD), including those in T-cell immunocompromised patients, transplant recipients, patients infected with HIV and children with congenital immunodeficiencies, EBV-induced polyclonal and monoclonal B-cell lymphoproliferative diseases occurring after transplantation (including renal), Hodgkins disease, T-lymphomas and rare NK/monocytoid/dendritic cell malignancies, sporadic epithelial carcinomas, leiomyosarcomas in immunodeficient patients and multicentric leiomyosarcoma in immunocompromised patients. Abnormal cells bearing the KHSV genome include Kaposi's infected cells, primary effusion lymphoma (which usually have both KHSV and EBV), multicentric Castleman's Disease (plasmablastic variant always KHSV-infected) and germanotrophic lymphoma.

(ii) A method, use, compound and composition for the treatment of a host with an EBV or KHSV infection, comprising administering an effective amount of one or a combination of the described 5-substituted uracil-nucleosides or its pharmaceutically acceptable salt or prodrug, optionally in a pharmaceutically acceptable carrier. In this embodiment, the uracil nucleoside is administered to the cell, selectively phosphorylated by the viral thymidine kinase and then acts as an inhibitor of one or more viral enzymes, for example, EBV or KHSV polymerase. In this embodiment, the 5-substituted uracil-nucleoside acts as a competitive inhibitor of viral growth. Examples of disorders that can be treated with this embodiment include mononucleosis (a disease caused by EBV that creates an excess of large lymphocytes that have a resemblance to monocytes in circulating blood), including complicated acute infectious mononucleosis, oral hairy leukoplakia, for reduction of EBV lytic replication following iatrogenic immunosuppression-a circumstance that may predispose a host to the development of EBV-associated lymphomas, and any other manifestation of viral infection.

(iii) A method use, compound and composition for the treatment of a host with an abnormal cellular proliferation or abnormal cell disorder, wherein the cell is EBV or KHSV negative. In this embodiment, the EBV-thymidine kinase or KHSV thymidine kinase gene is administered to or directly surrounding the abnormal cell in a manner that causes the incorporation of the gene into the natural cellular nucleic acid. The viral thymidine kinase is then expressed in the host cell, and acts to phophorylate the separately administered 5-substituted uracil-nucleoside. The therapy then proceeds as described in (i) above.

It is of importance to note that over half of diagnosed Hodgkins disease involves EBV and that substantial lymphoproliferative disease is associated with HIV infected patients. Certain of the uracil nucleosides described herein also have activity against HIV, and thus can be used to treat patients that exhibit both HIV infection and a resulting lymphoproliferative disease.

In one embodiment of the invention, the selected compound is of the formula (I), (II), or (III):

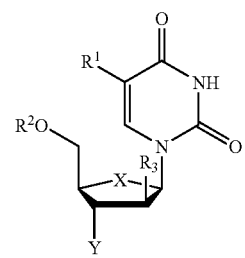

I

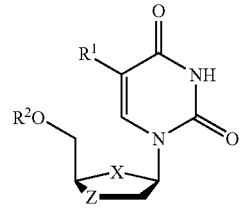

II

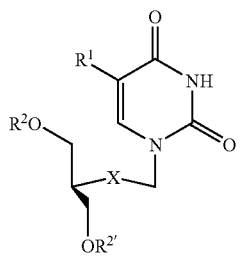

or its pharmaceutically acceptable salt or prodrug thereof, wherein i) X is O, S, $NR^4$, $CH_2$, CHF or $CF_2$;
ii) $R^1$ is H, halogen (Cl, Br, I, F), alkyl (including $C_1$, $C_2$, $C_3$, $C_4$, $C_5$, and $C_6$), haloalkyl (including $C_1$, $C_2$, $C_3$, $C_4$, $C_5$, and $C_6$), alkenyl (including $C_2$, $C_3$, $C_4$, $C_5$, and $C_6$), haloalkenyl (including $C_2$, $C_3$, $C_4$, $C_5$, and $C_6$), alkynyl (including $C_2$, $C_3$, $C_4$, $C_5$, and $C_6$), haloalkynyl (including $C_2$, $C_3$, $C_4$, $C_5$, and $C_6$), cycloalkyl (including $C_3$, $C_4$, $C_5$, $C_6$, $C_7$, and $C_8$), CN, $CF_3$, $N_3$, $NO_2$, aryl (including $C_6$, $C_7$, $C_8$, $C_9$, and $C_{10}$), heteroaryl (including $C_4$, $C_5$, $C_6$, $C_7$, $C_8$, $C_9$, and $C_{10}$), acyl (including $C_2$, $C_3$, $C_4$, $C_5$, and $C_6$), and $COR^5$ where $R^5$ is chosen from one of H, OH, SH, alkyl (including $C_1$, $C_2$, $C_3$, $C_4$, $C_5$, and $C_6$), aminoalkyl (including $C_1$, $C_2$, $C_3$, $C_4$, $C_5$, and $C_6$), alkoxy (including $C_1$, $C_2$, $C_3$, $C_4$, $C_5$, and $C_6$), or thioalkyl (including $C_1$, $C_2$, $C_3$, $C_4$, $C_5$, and $C_6$);
iii) $R^2$ and $R^{2'}$ are independently H, carbonyl substituted with an alkyl (including $C_1$, $C_2$, $C_3$, $C_4$, $C_5$, and $C_6$), alkenyl (including $C_2$, $C_3$, $C_4$, $C_5$, and $C_6$), alkynyl (including $C_2$, $C_3$, $C_4$, $C_5$, and $C_6$), aryl (including $C_6$, $C_7$, $C_8$, $C_9$, and $C_{10}$); benzyl, wherein the phenyl group is optionally substituted with one or more substituents; phosphate (including monophosphate, diphosphate, triphosphate or a stabilized phosphate prodrug); phosphate ester; sulfonate ester including alkyl or arylalkyl sulfonyl including methanesulfonyl; a lipid including a phospholipid; amino acid; peptide; cholesterol, or other pharmaceutically acceptable leaving group, preferably such that when administered in vivo, is capable of providing a compound wherein $R^2$ and/or $R^{2'}$ is independently H;
iv) $R^3$ is OH, halo (F, Cl, Br, I), a protected hydroxyl group or $CH_2OR^4$;
v) each $R^4$ is independently H, acyl (including $C_2$, $C_3$, $C_4$, $C_5$, and $C_6$), alkyl (including $C_1$, $C_2$, $C_3$, $C_4$, $C_5$, and $C_6$), alkenyl (including $C_2$, $C_3$, $C_4$, $C_5$, and $C_6$), alkynyl (including $C_2$, $C_3$, $C_4$, $C_5$, and $C_6$), or cycloalkyl (including $C_3$, $C_4$, $C_5$, $C_6$, $C_7$, and $C_8$);
vi) Y is H, OH, halogen (F, Cl, Br, I), $N_3$, CN, or $OR^{2'}$; and
vii) Z is O, S, alkyl (including $C_1$, $C_2$, $C_3$, $C_4$, $C_5$, and $C_6$), alkenyl (including $C_2$, $C_3$, $C_4$, $C_5$, and $C_6$), alkynyl (including $C_2$, $C_3$, $C_4$, $C_5$, and $C_6$), $CH_2$, CHF, or $CF_2$.

The compound of the present invention can be in the form of the β-L or β-D configuration, or any mixture of the two configurations, including a racemic mixture.

$R^2$ and $R^{2'}$ are independently hydrogen or pharmaceutically acceptable leaving group, which when administered in vivo, is capable of providing a compound wherein $R^2$ and/or $R^{2'}$ is independently H. For example, $R^2$ and $R^{2'}$ independently can be hydrogen, acyl, including a carbonyl substituted with a alkyl (including $C_1$, $C_2$, $C_3$, $C_4$, $C_5$, and $C_6$), alkenyl (including $C_2$, $C_3$, $C_4$, $C_5$, and $C_6$), alkynyl (including $C_2$, $C_3$, $C_4$, $C_5$, and $C_6$), aryl (including $C_6$, $C_7$, $C_8$, $C_9$, and $C_{10}$); benzyl, wherein the phenyl group is optionally substituted with one or more substituents which may be cleaved by cellular esterase. Alternatively, $R^2$ and $R^{2'}$ independently can be hydrogen or an acid or base labile leaving group, though preferably an acid-labile leaving group, such as phosphate (including monophosphate, diphosphate, triphosphate or a stabilized phosphate prodrug); phosphate ester; sulfonate ester including alkyl or arylalkyl sulfonyl including methanesulfonyl; a lipid including a phospholipid; amino acid; peptide or cholesterol. In a preferred embodiment, $R^2$ and/or $R^{2'}$ are independently hydrogen or a group that increases the activity, bioavailability and/or stability of the selected compound, which when administered in vivo, is capable of providing a compound wherein $R^2$ and/or $R^{2'}$ is independently H.

The selected uracil nucleoside derivatives are produced by synthetic methods that are readily known to those of ordinary skill in the art, a number of which are described below.

In one preferred embodiment, β-D-2'-deoxy-5-vinyluridine (also referred to as 5-vinyl-dU) is administered. This compound shows selectivity for EBV-TK, i.e. is specifically phosphorylated and converted into a cytotoxic agent by EBV-TK. Another specific example of a selected compound includes β-D-2'-deoxy-5-ethynyluridine (5-ethynyl-dU) that is also active against human immunodeficiency virus type 1 with an $EC_{50}$ of 0.61 µM.

In other preferred embodiments, the selected compounds are β-L-2'-deoxy-5-vinyluridine, β-L-5-vinyluridine, β-L-2'-deoxy-5-iodouridine, β-D-2'-deoxy-5-(hydroxymethyl) uridine, β-D-5-butyl-2'-deoxyuridine, β-D-5-E-(2-carboxyvinyl)-2'-deoxyuridine, (2S,4S)-5-(2-furanyl)-1-[2-(hydroxymethyl)-1,3-dioxolan-4-yl]uracil, (2S,4S)-5-(5-bromo-2-furanyl)-1-[2-(hydroxymethyl)-1,3-dioxolan-4-yl]uracil, (2S,4S)-5-(2-thienyl)-1-[2-(hydroxymethyl)-1,3-dioxolan-4-yl]uracil, (2S,4S)-5-(5-bromthien-2-yl)-1-[2-(hydroxymethyl)-1,3-dioxolan-4-yl]uracil, and (2S,4S)-5-(3-hydroxypropenyl)-1-[2-(hydroxymethyl)-1,3-dioxolan-4-yl]uracil. These compounds show selectivity for EBV-TK (i.e., are specifically phosphorylated and converted into a cytotoxic agent by EBV-TK).

In another embodiment, the present therapy is used in combination or alternation with other known or developed therapies for EBV or KHSV infected cells, including but not limited to Ganciclovir with or without arginine butyrate, Valaciclovir (Valtrex), donor white blood cells that have been treated in the laboratory to kill cells infected with EBV, white blood cells from donors who are immune to Epstein-Barr virus, LFMAU, and the compounds in U.S. Pat. Nos. 5,792,773, 6,022,876 and 6,274,589 (Yale University and The University of Georgia Research Foundation, Inc.).

Gene Therapy

The invention includes suicide gene therapy that employs the EBV-TK or KHSV-TK gene plus a selected uracil nucleoside derivative as described herein. The EBV-TK or KHSV-TK gene is delivered into areas within and surrounding the abnormal cellular proliferation or disorder to be treated, is taken up by the cells and can be incorporated into the cellular nucleic acid. The virus then expresses the viral thymidine kinase which phosphorylates the separately administered uracil nucleoside. A bystander effect can be achieved through production of locally high levels of the resulting phosphorylated uracil nucleoside. Because of the bystander effect, this treatment is effective in destroying the tumor cells that contain as few as 10% TK-expressing cells.

Adjacent cells that replicate rapidly take up the cytotoxic phosphorylated nucleoside. The EBV-TK and KHSV-TK genes additionally sensitize abnormal cells to radiation, suggesting possible combination therapies to control advanced tumors.

Thus, similar to GCV-HSV-1-TK gene therapy, gene therapy using the selected nucleoside analogues and EBV-TK may be employed in the treatment of EBV, EBV-associated disease and cancer cells transfected with the gene encoding EBV-TK. Upon phosphorylation of the nucleoside analogue by these EBV-TK-expressing cells, the nucleoside triphosphate exerts its toxicity, resulting in the death of the transfected cancer or tumor cells.

The amount of EBV-TK or KHSV-TK can be increased in latently infected cells or transfected cells by administration of a compound that causes increased expression of the enzyme. Examples are the tumor promoter (12-O-tetradecanoylphorbol-13-acetate) PMA/TPA and the polar organic compound sodium butyrate (NaB). In another embodiment, arginine butyrate (ArgB) is administered. Other inducing agents include, but are not limited to, azacytidine, hydroxyurea, interferons, gamma radiation, retinoic acid and related retinoids.

In an alternative embodiment, cell lines transfected with EBV-TK, and their use in gene therapy are also provided. For example, a cell can be selected that will optimally target to the location of interest in the host for efficient therapy. The cell therapy can be autologous or heterologous. In autologous therapy, the host's own cells are removed, transfected with the EBV-TK or KHSV-TK gene as described in detail below or as otherwise known in the art, and then transferred back into the host. During heterologous therapy, third party donor cells are transfected with the gene of interest and then transplanted into the host in need of therapy.

The cells transfected with the EBV-TK or HH8V-TK gene express the enzyme after transplantation into the host. The viral thymidine kinase acts as a selective phosphorylating agent for a uracil nucleoside administered before, during and/or after cell transplantation, which in final triphosphorylated form, inhibits EBV or KHSV growth. This produces a therapeutic effect on any cells that include and express the EBV genome, regardless of the type of cell infection. The EBV-TK transfected cell lines can be used in screening and cytotoxicity assays. Cells transfected with EBV-TK or KHSV-TK that do not have an adverse biological effect on the host animal can be used in gene therapy in accordance with the present invention.

As one non-limiting example, the Epstein-Barr virus (EBV) thymidine kinase (TK) gene from the viral strain B-958 was cloned into the vector pCMV as described (Gustafson E A, Chillemi A C, Sage D R, Fingeroth J D. The Epstein-Barr virus thymidine kinase does not phosphorylate ganciclovir or acyclovir and demonstrates a narrow substrate specificity compared to the herpes simplex virus type 1 thymidine kinase. *Antimicrob Agents Chemother* 1998; 42(11), 2923–31). The vector was then transfected using Lipofectamine reagent into 2 human cell lines. The cells were selected and expression of the TK gene (RNA and protein) was determined. The cells were used to create two assay systems to assess the ability of EBV-TK to sensitize cells to candidate nucleoside analogs. Cells that expressed KHSV-TK were similarly prepared for assay.

As an additional non-limiting example, immortalized human embryonic kidney cells (293 cells) were used to produce 293 EBV-TK cells and 293 KHSV-TK cells. The 293 cells were co-transfected with pCMV EBV-TK and pSV2 neo and the 293 KHSV-TK cells were prepared similarly using the vector pCMV KHSV-TK together with pSV2 neo (co-transfection) or by using the single vector pcDNA3-KHSV-TK (which contains an endogenous selectable neo marker). The cells were selected and clones were documented to express KHSV-TK by RNA blot hybridization.

Positive EBV-TK clones were pooled to produce bulk populations and were used in cytotoxicity assays to screen candidate nucleoside analogs. Two cell systems are employed in the cytotoxicity assays to determine the toxicity of each nucleoside. The information obtained depends upon the system used. In 143B TK-cells, cytotoxic drugs that are dependent upon phosphorylation by a TK are easily identified. 143B TK-cells expressing either EBV-TK or hTK1 permit assessment of whether either enzyme independently may cause a drug to become cytotoxic. Thus, drugs that can be activated by hTK1, which would cause non-specific cytotoxicity, are readily identified, but these cells are grown in HAT media that "forces" nucleosides through the TK salvage pathway (EBV-TK or hTK1) and presents the possibility of a false positive. The 293 cells have endogenous hTK1 and EBV-TK is maintained by selection in G418. Thus, the normal hTK1 salvage pathway is operational, and nucleosides can be expected to flux through the cells normally. Drugs are incubated with 293 cells transformed with a neomycin (Neo) expressing plasmid (Neo control) and with cells transfected with the same plasmid also expressing EBV-TK. A nucleoside selectively activated by EBV-TK should cause toxicity on 293 EBV-TK and not on 293 Neo control cells. In both the 143B and 293 cell systems, toxicity is evaluated by cell survival.

An example of an assay in which the transfected cell lines may be employed is the colony formation assay, done with 293 transfectants. This assay is designed to identify nucleosides whose toxicity is due to incorporation into cellular DNA forming a lethal lesion as described for GCV (Rubsam L Z, Davidson B L, and Shewach D S. "Superior cytotoxicity with ganciclovir compared with acyclovir and 1-β-D-arabinofuranosylthymine in herpes simplex virus-thymidine kinase-expressing cells: a novel paradigm for cell killing" *Cancer Res* 1998; 58(17):3873–82). Such toxicity is not dependent upon constant exposure to drug, but only exposure to drug during log phase growth. Nucleosides that act via a different mechanism, such as chain termination or inhibition of an enzyme in a metabolic pathway, are often only cytostatic, and the cells may return to normal growth after drug removal. This assay exposes cells in log growth and then fixes them. A nucleoside that works effectively causes a decrease in the number of colonies, which is a direct indication of the number of cells able to survive and replicate after the initial exposure to drug.

BRIEF DESCRIPTION OF THE FIGURES

FIG. 1 is a non-limiting example of a synthesis of selected compounds of the present invention, and in particular, a synthesis of 5-E-(2-chlorovinyl)uracil nucleosides.

FIG. 2 is a non-limiting example of a synthesis of selected compounds of the present invention, and in particular, a synthesis of 5-vinyluracil nucleosides.

FIG. 3 is a non-limiting example of a synthesis of selected compounds of the present invention, and in particular, a synthesis of 5-ethynyluracil nucleosides.

FIG. 4 is a non-limiting example of a synthesis of selected compounds of the present invention, and in particular, a synthesis of acyclic 5-substituted uracil nucleosides.

FIG. 5 is a non-limiting example of a synthesis of selected compounds of the present invention, and in particular, a synthesis of 5-substituted uracil 4'-thionucleosides.

FIG. 6 is a non-limiting example of a synthesis of selected compounds of the present invention, and in particular, a synthesis of 5-substituted uracil carbocyclic nucleosides.

FIG. 7 is a non-limiting example of a synthesis of selected compounds of the present invention, and in particular, a synthesis of 5-substituted dioxolane nucleosides.

FIG. 8 is a non-limiting example of a synthesis of selected compounds of the present invention, and in particular, a synthesis of 5-substituted-thienyl uracil nucleosides.

FIG. 9 is a non-limiting example of a synthesis of selected compounds of the present invention, and in particular, a synthesis of 5-thienyl substituted dioxolane nucleosides.

FIG. 10 is a non-limiting example of a synthesis of selected compounds of the present invention, and in particular, a synthesis of 5-substituted 2'-deoxyuridine nucleosides.

FIG. 11 is a graphical representation of the competition effect of selected compounds with purified GST EBV-TK fusion proteins.

FIG. 12 is a graphical representation of the competition effect of selected compounds, comparing 143B TK-minus cells expressing EBV-TK with 143B TK-minus cells expressing re-introduced human TK-1 (hTK-1).

FIG. 13 is a graphical representation of the effects of 5-vinyl-2'-deoxyuridine (also referred to as 5-vinyl-dU) on colony formation in cells expressing EBV-TK versus endogenous hTK-1.

FIG. 14 is a graphical representation of the cytotoxicity of selected compounds on 143B cells expressing EBV-TK, hTK-1, or TK deficient (TK−) at 20 µM concentration.

FIG. 15 is a direct demonstration of the cytotoxic effect of selected compounds on 293 EBV-TK cells versus 293 Neo cells.

FIG. 16 is a representation of the dose-dependent inhibition of 5-vinyl-2'-deoxyuridine (5-vinyl-dU) on cells transfected with EBV-TK (293 EBV-TK cells) compared with 293 Neo cells.

FIG. 17 is a graphical representation of the cytotoxicity of selected compounds on 143B versus 143 EBV-TK cells after 5 days treatment at 20 µM.

FIG. 18 is a graphical representation of a competition assay between selected compounds and radio-labeled thymidine with purified GST-EBV-TK fusion protein

DETAILED DESCRIPTION OF THE INVENTION

It has been found that certain 5-substituted uracil-nucleosides are selectively phosphorylated by EBV thymidine kinase and/or KHSV thymidine kinase, and are not substantially phophorylated by human cellular thymidine kinase. EBV-TK is strictly a thymidine kinase with the capacity to phosphorylate thymidine and some thymidine analogs. Similar to the combination of HSV1-TK with ganciclovir (GCV), certain 5-substituted uracil nucleosides effectively kill EBV-TK-expressing cells, but not cells that do not express this enzyme. In one embodiment of the present invention, the nucleoside analogs are conditionally toxic to cells, dependent upon phosphorylation selectively by EBV-TK and the compounds' specificity for a cellular polymerase or transcriptase. Such toxicity will result in the selective destruction of tumor cells that express EBV-TK, but not human TK1 or -2 or other human nucleoside or nucleotide kinases. Notably, this is a distinct paradigm from that of traditional antiviral nucleoside analogues that seek to selectively inhibit the virus replication cycle and not interfere with that of the cell.

Several embodiments of the invention are provided.

(i) A method for the treatment of a host with an abnormal cellular proliferation or abnormal cell disorder, wherein the cell is EBV or KHSV positive, that includes administering an effective amount of one or a combination of the described 5-substituted uracil-nucleosides or its pharmaceutically acceptable salt or prodrug, optionally in a pharmaceutically acceptable carrier.

(ii) A method, use, compound and composition for the treatment of a host with an EBV or KHSV infection, comprising administering an effective amount of one or a combination of the described 5-substituted uracil-nucleosides or its pharmaceutically acceptable salt or prodrug, optionally in a pharmaceutically acceptable carrier. In this embodiment, the uracil nucleoside is administered to the cell, selectively phosphorylated by the viral thymidine kinase and then acts as an inhibitor of one or more viral enzymes, for example, EBV or KHSV polymerase. In this embodiment, the 5-substituted uracil-nucleoside acts as a competitive inhibitor of viral growth.

(iii) A method use, compound and composition for the treatment of a host with an abnormal cellular proliferation or abnormal cell disorder, wherein the cell is EBV or KHSV negative. In this embodiment, the EBV-thymidine kinase or KHSV thymidine kinase gene is administered to or directly surrounding the abnormal cell in a manner that causes the incorporation of the gene into the natural cellular nucleic acid. The viral thymidine kinase is then expressed in the host cell, and acts to phophorylate the separately administered 5-substituted uracil-nucleoside. The therapy then proceeds as described in (i) above.

In one embodiment of the present invention, the tumor cells already express EBV-TK and therefore there is no need for gene delivery, unlike in the HSV1-TK and GCV system.

The present invention therefore provides compounds, pharmaceutical compositions and methods for the treatment, inhibition or prophylaxis of a disease associated with infection or lytic replication of an Epstein-Barr virus (or the related gammaherpesvirus KHSV) including diseases associated with abnormally proliferating cells infected with EBV, in a host, particularly a human patient or other host animal, comprising administering an effective amount of at least one compound as described in the present invention, or its pharmaceutically acceptable salt or prodrug thereof, optionally in a pharmaceutically acceptable carrier or excipient.

In another aspect of the present invention, there is provided a pharmaceutical composition for the treatment, inhibition and/or prophylaxis of a disease associated with infection or lytic replication of an Epstein-Barr virus (or the related gammaherpesvirus KHSV) including diseases associated with abnormally proliferating cells infected with EBV in a host, particularly a human patient or other host animal, comprising administering an effective amount of at least one compound of the present invention, or its pharmaceutically acceptable salt or prodrug thereof, in combination with one or more other effective anti-EBV agent and/or agent that can induce and/or upregulate EBV-TK expression, or its pharmaceutically acceptable salt or prodrug thereof, optionally in a pharmaceutically acceptable carrier or excipient.

In still another aspect of the present invention, there is provided a method for the treatment, inhibition and/or prophylaxis of a disease associated with infection or lytic replication of an Epstein-Barr virus (or the related gammaherpesvirus KHSV) including diseases associated with abnormally proliferating cells infected with EBV in a host, particularly a human patient or other host animal, comprising administering an effective amount of at least one compound of the invention, its pharmaceutically acceptable salt or prodrug thereof, optionally in combination or alternation with one or more other effective anti-EBV agent and/or agent that can induce and/or upregulate EBV-TK expression, or its pharmaceutically acceptable salt or prodrug thereof, optionally in a pharmaceutically acceptable carrier or excipient.

In yet another aspect of the present invention, there is provided a use of at least one of the compounds of the present invention, or its pharmaceutically acceptable salt or prodrug, for the treatment, inhibition and/or prophylaxis of an EBV infection in a host, particularly a human patient or other host animal, optionally in combination or alternation with one or more other effective anti-EBV agent and/or agent that can induce and/or upregulate EBV-TK expression, or its pharmaceutically acceptable salt or prodrug thereof, optionally in a pharmaceutically acceptable carrier or excipient.

In yet another aspect of the present invention, there is provided a use of at least one of the compounds, or its pharmaceutically acceptable salts or prodrugs, for the treatment, inhibition and/or prophylaxis of a disease associated with infection or lytic replication of an Epstein-Barr virus (or the related gammaherpesvirus KHSV) including diseases associated with abnormally proliferating cells infected with EBV in a host, particularly a human patient or other host animal, optionally in combination or alternation with one or more other effective anti-EBV agent and/or agent that can induce and/or upregulate EBV-TK expression, or its pharmaceutically acceptable salt or prodrug thereof, optionally in a pharmaceutically acceptable carrier or excipient.

In yet another aspect of the present invention, there is provided a use of at least one of the compounds of the present invention, or its pharmaceutically acceptable salt or prodrug, in the manufacture of a medicament for the treatment, inhibition and/or prophylaxis of a disease associated with infection or lytic replication of an Epstein-Barr virus (or the related gammaherpesvirus KHSV) including diseases associated with abnormally proliferating cells that bear the EBV genome in a host, particularly a human patient or other host animal, optionally in combination or alternation with one or more other effective anti-EBV agent and/or agent that can induce and/or upregulate EBV-TK expression, or its pharmaceutically acceptable salt or prodrug thereof, optionally in a pharmaceutically acceptable carrier or excipient.

In an additional embodiment of the present invention, cell lines transfected with EBV-TK are provided. Another embodiment of the present invention, there is provided a use of a cell line transfected with EBV-TK for the treatment, inhibition and/or prophylaxis of a disease associated with infection or lytic replication of an Epstein-Barr virus (or the related gammaherpesvirus KHSV) including diseases associated with abnormally proliferating cells infected with EBV in a host, particularly a human patient or other host animal, is provided, by administering to said cell line an effective amount of an agent selectively activated by EBV-TK into a cytotoxic agent, or its pharmaceutically acceptable salt or prodrug thereof, optionally in combination or alternation with one or more other effective agent, or its pharmaceutically acceptable salt or prodrug thereof, optionally in a pharmaceutically acceptable carrier or excipient. In a preferred embodiment of the present invention, the agent selectively activated by EBV-TK is a compound of the present invention. In one embodiment of the invention, the effective agent administered in combination or alternation with the agent selectively activated by EBV-TK is an effective anti-proliferative agent. In an additional embodiment of the invention, the effective agent administered in combination or alternation with the agent selectively activated by EBV-TK is an effective anti-EBV agent, and in particular an agent selectively activated by EBV-TK. In yet another embodiment of the invention, the effective agent administered in combination or alternation with the agent selectively activated by EBV-TK is an effective agent that can induce and/or upregulate EBV-TK expression.

Therefore, assays and kits for detecting inhibition of abnormal cellular proliferation using the cell lines transfected with EBV-TK are also provided. In another embodiment of the present invention, assays and kits are provided to analyze and predict the desired cytotoxic and virotoxic activities in cells in which EBV-TK is expressed either independently of or together with viral and cellular enzymes that are potentially able to utilize and modify nucleoside analog substrates, such as cellular kinases.

A method for the treatment, inhibition and/or prophylaxis of a disease associated with infection or lytic replication of an Epstein-Barr virus (or the related gammaherpesvirus KHSV) including diseases associated with abnormally proliferating cells infected with EBV in a host, particularly a human patient or other host animal, is provided comprising transfecting cells with EBV-TK, if necessary, and administering an effective amount of an agent selectively activated by EBV-TK into a cytotoxic agent, or its pharmaceutically acceptable salt or prodrug thereof, optionally in combination or alternation with one or more other effective agent, or its pharmaceutically acceptable salt or prodrug thereof, optionally in a pharmaceutically acceptable carrier or excipient. In a preferred embodiment of the present invention, the agent selectively activated by EBV-TK is a compound of the present invention. In one embodiment of the invention, the effective agent administered in combination or alternation with the agent selectively activated by EBV-TK is an effective anti-proliferative agent. In an additional embodiment of the invention, the effective agent administered in combination or alternation with the agent selectively activated by EBV-TK is an effective anti-EBV agent, and in particular an agent selectively activated by EBV-TK. In yet another embodiment of the invention, the effective agent administered in combination or alternation with the agent selectively activated by EBV-TK is an effective agent that can induce and/or upregulate EBV-TK expression.

In yet another embodiment of the invention, there is provided a use of at least one of the compounds of the present invention, or its pharmaceutically acceptable salt or prodrug thereof, for the treatment, inhibition and/or prophylaxis of a disease associated with infection or lytic replication of an Epstein-Barr virus (or the related gammaherpesvirus KHSV) including diseases associated with abnormally proliferating cells infected with EBV in a host, particularly a human patient or other host animal, is provided, optionally in combination or alternation with one or more other effective agent, or its pharmaceutically acceptable salt or prodrug thereof, optionally in a pharmaceutically acceptable carrier or excipient. In a preferred embodiment of the present invention, the agent selectively activated by EBV-TK is a compound of the present invention. In one embodiment of the invention, the effective agent administered in combination or alternation with the agent selectively activated by EBV-TK is an effective anti-proliferative agent. In an additional embodiment of the invention, the effective agent administered in combination or alternation with the agent selectively activated by EBV-TK is an effective anti-EBV agent, and in particular an agent selectively activated by EBV-TK. In yet another embodiment of the invention, the effective agent administered in combination or alternation with the agent selectively activated by EBV-TK is an effective agent that can induce and/or upregulate EBV-TK expression.

In yet another embodiment of the invention, there is provided a use of at least one of the compounds of the present invention, or its pharmaceutically acceptable salt or prodrug, in the manufacture of a medicament for the treatment, inhibition and/or prophylaxis of a disease associated with infection or lytic replication of an Epstein-Barr virus (or the related gammaherpesvirus KHSV) including diseases associated with abnormally proliferating cells infected with EBV, where cells can be transfected with EBV-TK, if necessary, in a host, particularly a human patient or other host animal, is provided, optionally in combination or alternation with one or more other effective agent, or its pharmaceutically acceptable salt or prodrug thereof, optionally in a pharmaceutically acceptable carrier or excipient. In a preferred embodiment of the present invention, the agent selectively activated by EBV-TK is a compound of the present invention. In one embodiment of the invention, the effective agent administered in combination or alternation with the agent selectively activated by EBV-TK is an effective anti-proliferative agent. In an additional embodiment of the invention, the effective agent administered in combination or alternation with the agent selectively activated by EBV-TK is an effective anti-EBV agent, and in particular an agent selectively activated by EBV-TK. In yet another embodiment of the invention, the effective agent administered in combination or alternation with the agent selectively activated by EBV-TK is an effective agent that can induce and/or upregulate EBV-TK expression.

In another embodiment of the present invention, a use of a cell line transfected with EBV-TK in the manufacture of a medicament for the treatment, inhibition and/or prophylaxis of a disease associated with infection or lytic replication of an Epstein-Barr virus (or the related gammaherpesvirus KHSV) including diseases associated with abnormally proliferating cells infected with EBV in a host, particularly a human patient or other host animal, is provided, by administering to said cell line an effective amount of an agent selectively activated by EBV-TK into a cytotoxic agent, or its pharmaceutically acceptable salt or prodrug thereof, optionally in combination or alternation with one or more other effective agent, or its pharmaceutically acceptable salt or prodrug thereof, optionally in a pharmaceutically acceptable carrier or excipient. In a preferred embodiment of the present invention, the agent selectively activated by EBV-TK is a compound of the present invention. In one embodiment of the invention, the effective agent administered in combination or alternation with the agent selectively activated by EBV-TK is an effective anti-proliferative agent. In an additional embodiment of the invention, the effective agent administered in combination or alternation with the agent selectively activated by EBV-TK is an effective anti-EBV agent, and in particular an agent selectively activated by EBV-TK. In yet another embodiment of the invention, the effective agent administered in combination or alternation with the agent selectively activated by EBV-TK is an effective agent that can induce and/or upregulate EBV-TK expression.

I Selected Compounds

In one embodiment of the invention, the selected compound is of formula (I), (II), or (III):

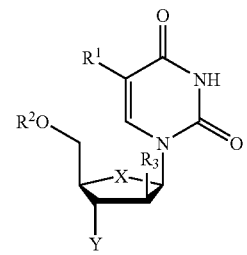

I

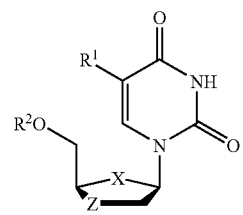

II

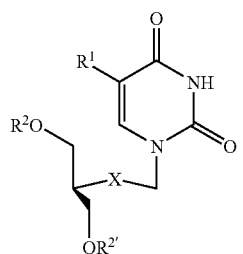

III or its pharmaceutically acceptable salt or prodrug thereof, wherein i) X is O, S, $NR^4$, $CH_2$, CHF or $CF_2$;

ii) $R^1$ is H, halogen (Cl, Br, I, F), alkyl (including $C_1$, $C_2$, $C_3$, $C_4$, $C_5$, and $C_6$), haloalkyl (including $C_1$, $C_2$, $C_3$, $C_4$, $C_5$, and $C_6$), alkenyl (including $C_2$, $C_3$, $C_4$, $C_5$, and $C_6$), haloalkenyl (including $C_2$, $C_3$, $C_4$, $C_5$, and $C_6$), alkynyl (including $C_2$, $C_3$, $C_4$, $C_5$, and $C_6$), haloalkynyl (including $C_2$, $C_3$, $C_4$, $C_5$, and $C_6$), cycloalkyl (including $C_3$, $C_4$, $C_5$, $C_6$, $C_7$, and $C_8$), CN, $CF_3$, $N_3$, $NO_2$, aryl (including $C_6$, $C_7$, $C_8$, $C_9$, and $C_{10}$), heteroaryl (including $C_4$, $C_5$, $C_6$, $C_7$, $C_8$, $C_9$, and $C_{10}$), acyl (including $C_2$, $C_3$, $C_4$, $C_5$, and $C_6$), and $COR^5$ where $R^5$ is chosen from one of H, OH, SH, alkyl (including $C_1$, $C_2$, $C_3$, $C_4$, $C_5$, and $C_6$), aminoalkyl (including $C_1$, $C_2$, $C_3$, $C_4$, $C_5$, and $C_6$), alkoxy (including $C_1$, $C_2$, $C_3$, $C_4$, $C_5$, and $C_6$), or thioalkyl (including $C_1$, $C_2$, $C_3$, $C_4$, $C_5$, and $C_6$);

iii) $R^2$ and $R^{2'}$ are independently H, carbonyl substituted with an alkyl (including $C_1$, $C_2$, $C_3$, $C_4$, $C_5$, and $C_6$), alkenyl (including $C_2$, $C_3$, $C_4$, $C_5$, and $C_6$), alkynyl (including $C_2$, $C_3$, $C_4$, $C_5$, and $C_6$), aryl (including $C_6$, $C_7$, $C_8$, $C_9$, and $C_{10}$); benzyl, wherein the phenyl group is optionally substituted with one or more substituents; phosphate (including monophosphate, diphosphate, triphosphate or a stabilized phosphate prodrug); phosphate ester; sulfonate ester including alkyl or arylalkyl sulfonyl including methanesulfonyl; a lipid including a phospholipid; amino acid; peptide; cholesterol, or other pharmaceutically acceptable leaving group, preferably such that when administered in vivo, is capable of providing a compound wherein $R^2$ and/or $R^{2'}$ is independently H;

iv) $R^3$ is OH, halo (F, Cl, Br, I), protected hydroxyl group or $CH_2OR^4$;

v) each $R^4$ is independently H, acyl (including $C_2$, $C_3$, $C_4$, $C_5$, and $C_6$), alkyl (including $C_1$, $C_2$, $C_3$, $C_4$, $C_5$, and $C_6$), alkenyl (including $C_2$, $C_3$, $C_4$, $C_5$, and $C_6$), alkynyl (including $C_2$, $C_3$, $C_4$, $C_5$, and $C_6$), or cycloalkyl (including $C_3$, $C_4$, $C_5$, $C_6$, $C_7$, and $C_8$);

vi) Y is H, OH, halogen (F, Cl, Br, I), $N_3$, CN, or $OR^{2'}$; and vii) Z is O, S, $NO_2$, alkyl (including $C_1$, $C_2$, $C_3$, $C_4$, $C_5$, and $C_6$), alkenyl (including $C_2$, $C_3$, $C_4$, $C_5$, and $C_6$), alkynyl (including $C_2$, $C_3$, $C_4$, $C_5$, and $C_6$), $CH_2$, CHF, or $CF_2$.

The compound of the present invention can be in the form of the β-L or β-D configuration, or a racemic mixture.

In one embodiment of the invention, it is desired for the compound to be selectively activated by EBV-TK (or the related KHSV-TK); therefore $R^2$ and $R^{2'}$ are independently hydrogen or pharmaceutically acceptable leaving group, which when administered in vivo, is capable of providing a compound wherein $R^2$ and/or $R^{2'}$ is independently H. For example, $R^2$ and $R^{2'}$ independently can be hydrogen or carbonyl substituted with a alkyl (including $C_1$, $C_2$, $C_3$, $C_4$, $C_5$, and $C_6$), alkenyl (including $C_2$, $C_3$, $C_4$, $C_5$, and $C_6$), alkynyl (including $C_2$, $C_3$, $C_4$, $C_5$, and $C_6$), aryl (including $C_6$, $C_7$, $C_8$, $C_9$, and $C_{10}$); benzyl, wherein the phenyl group is optionally substituted with one or more substituents which may be cleaved by cellular esterase. Alternatively, $R^2$ and $R^{2'}$ independently can be hydrogen or an acid or base labile leaving group, though preferably an acid-labile leaving group, such as phosphate (including monophosphate, diphosphate, triphosphate or a stabilized phosphate prodrug); phosphate ester; sulfonate ester including alkyl or arylalkyl sulfonyl including methanesulfonyl; a lipid including a phospholipid; amino acid; peptide or cholesterol. In a preferable embodiment, $R^2$ and/or $R^{2'}$ are independently hydrogen or a group that increases the activity, bioavailability and/or stability of the selected compound, which when administered in vivo, is capable of providing a compound wherein $R^2$ and/or $R^{2'}$ is independently H.

In one preferred embodiment, the selected compound is β-D-2'-deoxy-5-vinyluridine (also referred to as 5-vinyl-dU) of the structure:

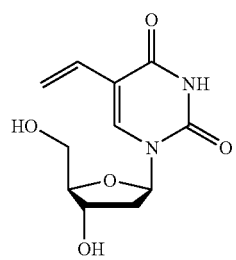

or a pharmaceutically acceptable salt or prodrug thereof.

In an additional embodiment, the selected compound is β-D-2'-deoxy-5-ethynyluridine (also referred to as 5-ethynyl-dU) of the structure:

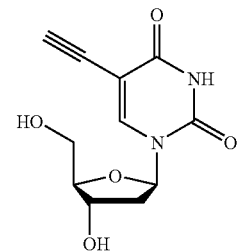

or a pharmaceutically acceptable salt or prodrug thereof. This compound shows also activity against human immunodeficiency virus with an $EC_{50}$ of 0.61 μM.

In one preferred embodiment, the selected compound is β-L-2'-deoxy-5-vinyluridine of the structure:

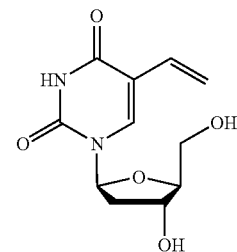

or a pharmaceutically acceptable salt or prodrug thereof.

In another preferred embodiment, the selected compound is β-L-5-vinyluridine of the structure:

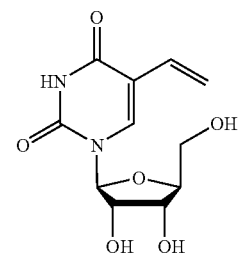

or a pharmaceutically acceptable salt or prodrug thereof.

In another preferred embodiment, the selected compound is β-L-2'-deoxy-5-iodouridine of the structure:

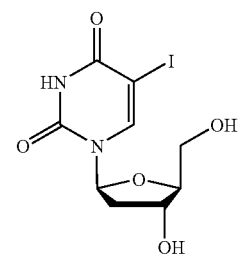

or a pharmaceutically acceptable salt or prodrug thereof.

In another preferred embodiment, the selected compound is β-D-2'-deoxy-5-(hydroxymethyl)uridine of the structure:

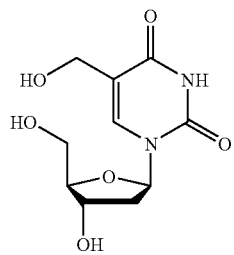

or a pharmaceutically acceptable salt or prodrug thereof.

In one preferred embodiment, the selected compound is β-D-5-butyl-2'-deoxyuridine of the structure:

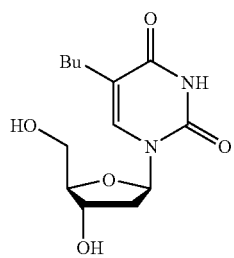

or a pharmaceutically acceptable salt or prodrug thereof.

In one preferred embodiment, the selected compound is β-D-5-E-(2-carboxyvinyl)-2'-deoxyuridine of the structure:

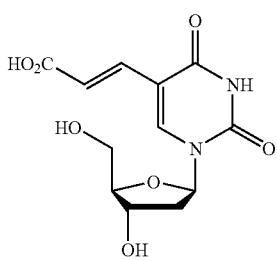

or a pharmaceutically acceptable salt or prodrug thereof.

In one preferred embodiment, the selected compound is (2S,4S)-5-(2-furanyl)-1-[2-(hydroxymethyl)-1,3-dioxolan-4-yl]uracil of the structure:

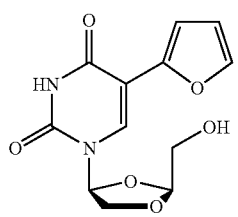

or a pharmaceutically acceptable salt or prodrug thereof.

In one preferred embodiment, the selected compound is (2S,4S)-5-(5-bromo-2-furanyl)-1-[2-(hydroxymethyl)-1,3-dioxolan-4-yl]uracil of the structure:

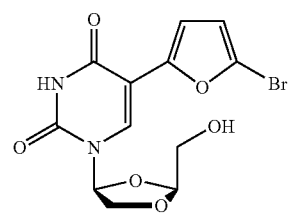

or a pharmaceutically acceptable salt or prodrug thereof.

In one preferred embodiment, the selected compound is (2S,4S)-5-(2-thienyl)-1-[2-(hydroxymethyl)-1,3-dioxolan-4-yl]uracil of the structure:

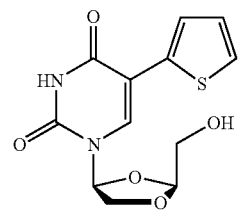

or a pharmaceutically acceptable salt or prodrug thereof.

In one preferred embodiment, the selected compound is, (2S,4S)-5-(5-bromthien-2-yl)-1-[2-(hydroxymethyl)-1,3-dioxolan-4-yl]uracil of the structure:

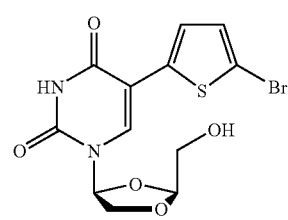

or a pharmaceutically acceptable salt or prodrug thereof.

In one preferred embodiment, the selected compound is (2S,4S)-5-(3-hydroxypropenyl)-1-[2-(hydroxymethyl)-1,3-dioxolan-4-yl]uracil of the structure:

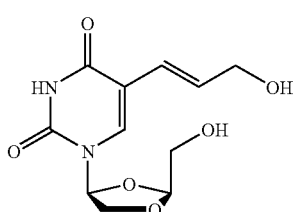

or a pharmaceutically acceptable salt or prodrug thereof.

II Definitions

The term "independently" is used herein to indicate that the variable, which is independently applied, varies independently from application to application. Thus, in a compound such as R"XYR", wherein R" is "independently carbon or nitrogen," both R" can be carbon, both R" can be nitrogen, or one R" can be carbon and the other R" nitrogen.

As used herein, the term "enantiomerically pure" refers to a nucleoside composition that comprises at least approximately 95%, and preferably approximately 97%, 98%, 99% or 100% of a single enantiomer of that nucleoside.

As used herein, the term "substantially free of" or "substantially in the absence of" refers to a nucleoside composition that includes at least 85 or 90% by weight, preferably 95% to 98% by weight, and even more preferably 99% to 100% by weight, of the designated enantiomer of that nucleoside. In a preferred embodiment, in the methods and compounds of this invention, the compounds are substantially free of enantiomers.

Similarly, the term "isolated" refers to a nucleoside composition that includes at least 85 or 90% by weight, preferably 95% to 98% by weight, and even more preferably 99% to 100% by weight, of the nucleoside, the remainder comprising other chemical species or enantiomers.

The term "alkyl," as used herein, unless otherwise specified, refers to a saturated straight, branched, or cyclic, primary, secondary, or tertiary hydrocarbon of typically $C_1$, $C_2$, $C_3$, $C_4$, $C_5$, $C_6$, $C_7$, $C_8$, $C_9$, or $C_{10}$, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups. Moieties with which the alkyl group can be substituted are selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene et al., *Protective Groups in Organic Synthesis,* John Wiley & Sons, 2$^{nd}$ Edition, 1991, hereby incorporated by reference.

The term "lower alkyl," as used herein, and unless otherwise specified, refers to a $C_1$, $C_2$, $C_3$, or $C_4$ saturated straight, branched, or if appropriate, a cyclic (for example, cyclopropyl) alkyl group, including both substituted and unsubstituted forms. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The terms "alkylamino" or "arylamino" refer to an amino group that has one or two alkyl or aryl substituents, respectively.

The term "alkoxy" as used herein includes linear or branched oxy-containing radicals having alkyl moieties, such as methoxy radical. The term "alkoxyalkyl" also embraces alkyl radicals having one or more alkoxy radicals attached to the alkyl radical, that is, to form monoalkoxyalkyl and dialkoxyalkyl radicals. The "alkoxy" radicals may be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "protected," as used herein and unless otherwise defined, refers to a group that is added to an oxygen, nitrogen, or phosphorus atom to prevent its further reaction or for other purposes. A wide variety of oxygen and nitrogen protecting groups are known to those skilled in the art of organic synthesis.

The term "aryl," as used herein, and unless otherwise specified, refers to phenyl, biphenyl, or naphthyl, and preferably phenyl. The term includes both substituted and unsubstituted moieties. The aryl group can be substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis,* John Wiley and Sons, Second Edition, 1991.

The terms "alkaryl" or "alkylaryl" refer to an alkyl group with an aryl substituent. The terms "aralkyl" or "arylalkyl" refer to an aryl group with an alkyl substituent.

The term "halo," as used herein, includes chloro, bromo, iodo and fluoro.

The term "acyl" refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen (F, Cl, Br, I), alkyl (including $C_1$, $C_2$, $C_3$, and $C_4$) or alkoxy (including $C_1$, $C_2$, $C_3$, and $C_4$), sulfonate esters such as alkyl or aralkyl sulfonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group.

The terms "heteroaryl" or "heteroaromatic," as used herein, refer to an aromatic that includes at least one sulfur, oxygen, nitrogen or phosphorus in the aromatic ring.

The term "lower acyl" refers to an acyl group in which the non-carbonyl moiety is lower alkyl.

The term "host," as used herein, refers to a unicellular or multicellular organism in which the virus can replicate, including cell lines and animals, and preferably a human. Alternatively, the host can be carrying a part of the viral genome, whose replication or function can be altered by the compounds of the present invention. The term host specifically refers to infected cells, cells transfected with all or part of the viral genome and animals, in particular, primates and humans. In most animal applications of the present invention, the host is a human-patient. Veterinary applications, in certain indications, however, are clearly anticipated by the present invention.

III Pharmaceutically Acceptable Salts or Prodrugs

The term "pharmaceutically acceptable salt or prodrug" is used throughout the specification to describe any pharmaceutically acceptable form (such as an ester, phosphate ester, salt of an ester or a related group) of a compound which, upon administration to a patient, provides the active compound. Pharmaceutically acceptable salts include those derived from pharmaceutically acceptable inorganic or organic bases and acids. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the selected compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. The compounds of this invention possess antiviral activity against Epstein-Barr virus and/or cytotoxic activity against cells expressing EBV-TK, i.e., EBV-infected cells, and, in particular, EBV-infected cells that abnormally proliferate (develop into tumors), or EBV-TK transduced cells, or are metabolized to a compound that exhibits such activity.

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate and α-glycerophosphate. Suitable inorganic salts may also be formed, including, sulfate, nitrate, bicarbonate and carbonate salts.

Alternatively, pharmaceutically acceptable salts may be obtained, for example by reacting a sufficiently basic compound such as an amine with a suitable acid affording a physiologically acceptable anion. Alkali metal (for example, sodium, potassium or lithium) or alkaline earth metal (for example calcium and magnesium) salts of, for example, carboxylic acids can also be made.

Any of the compounds described herein can be administered as a prodrug to increase the activity, bioavailability, stability or otherwise alter the properties of the selected compound. A number of prodrug ligands are known. In general, alkylation, acylation or other lipophilic modification of the mono, di or triphosphate of the compound, for example the nucleoside will increase the stability of the compound, for example as a nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones & N. Bischofberger, *Antiviral Research*, 27 (1995) 1–17. Any of these can be used in combination with the disclosed nucleosides to achieve a desired effect.

The selected compounds can also be provided as a 5'-phosphoether lipid or a 5'-ether lipid, as disclosed in the following references, which are incorporated by reference herein: Kucera L. S., N. Iyer, E. Leake, A. Raben, Modest E. K., Daniel L. W., C. Piantadosi, "Novel membrane-interactive ether lipid analogs that inhibit infectious HIV-1 production and induce defective virus formation," *AIDS Res. Hum. Retroviruses*, 1990, 6, 491–501; Piantadosi C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, E. J. Modest, "Synthesis and evaluation of novel ether lipid nucleoside conjugates for anti-HIV activity," *J. Med. Chem.*, 1991, 34, 1408–1414; Hostetler K. Y., D. D. Richman, D. A. Carson, L. M. Stuhmiller, G. M. T. van Wijk, H. van den Bosch, "Greatly enhanced inhibition of human immunodeficiency virus type 1 replication in CEM and HT4-6C cells by 3'-deoxythymidine diphosphate dimyristoylglycerol, a lipid prodrug of 3,-deoxythymidine," *Antimicrob. Agents Chemother.*, 1992, 36, 2025–2029; Hostetler K. Y., L. M. Stuhrmiller, H. B. Lenting, H. van den Bosch, D. D. Richman, "Synthesis and antiretroviral activity of phospholipid analogs of azidothymidine and other antiviral nucleosides." *J. Biol. Chem.*, 1990, 265, 61127.

Nonlimiting examples of U.S. patents that disclose suitable lipophilic substituents that can be covalently incorporated into the compound, preferably at the 5'-OH position of the compound or lipophilic preparations, include U.S. Pat. No. 5,149,794 (Yatvin et al.); U.S. Pat. No. 5,194,654 (Hostetler et al., U.S. Pat. No. 5,223,263 (Hostetler et al.); U.S. Pat. No. 5,256,641 (Yatvin et al.); U.S. Pat. No. 5,411,947 (Hostetler et al.); U.S. Pat. No. 5,463,092 (Hostetler et al.); U.S. Pat. No. 5,543,389 (Yatvin et al.); U.S. Pat. No. 5,543,390 (Yatvin et al.); U.S. Pat. No. 5,543,391 (Yatvin et al.); and U.S. Pat. No. 5,554,728 (Basava et al.), all of which are incorporated by reference. Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721, all of which are incorporated by reference.

Prodrugs also include amino acid esters of the disclosed nucleosides (see, e.g., European Patent Specification No. 99493, the text of which is incorporated by reference, which describes amino acid esters of acyclovir, specifically the glycine and alanine esters which show improved water-solubility compared with acyclovir itself, and U.S. Pat. No. 4,957,924 (Beauchamp), which discloses the valine ester of acyclovir, characterized by side-chain branching adjacent to the alpha-carbon atom, which showed improved bioavailability after oral administration compared with the alanine and glycine esters). A process for preparing such amino acid esters is disclosed in U.S. Pat. No. 4,957,924 (Beauchamp), the text of which is incorporated by reference. As an alternative to the use of valine itself, a functional equivalent of the amino acid may be used (e.g., an acid halide such as the acid chloride, or an acid anhydride). In such a case, to avoid undesirable side-reactions, it may be is advantageous to use an amino-protected derivative.

IV Combination or Alternation Therapy

In another embodiment, for the treatment, inhibition, prevention and/or prophylaxis of Epstein-Barr viral infection, the selected compound or its derivative or salt can be administered in combination or alternation with another antiviral agent, such as anti-EBV agent, including those of the formula above. In general, in combination therapy, effective dosages of two or more agents are administered together, whereas during alternation therapy, an effective dosage of each agent is administered serially. The dosage will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Nonlimiting examples of antiviral agents that can be used in combination with the compounds disclosed herein include acyclovir (ACV), AZT, 3TC, d4T, ganciclovir (GCV or DHPG) and its prodrugs (e.g., valyl-ganciclovir), E-5-(2-bromovinyl)-2'-deoxyuridine (BVDU), (E)-5-vinyl-1-β-D-arabonosyluracil (VaraU), (E)-5-(2-bromovinyl)-1-β-D-arabinosyluracil (BV-araU), 1-(2-deoxy-2-fluoro-β-D-arabinosyl)-5-iodocytosine (D-FIAC), 1-(2-deoxy-2-fluoro-β-L-arabinosyl)-5-methyluracil (L-FMAU), (S)-9-(3-hydroxy-2-phosphonylmethoxypropyl)adenine [(S)-HPMPA], (S)-9-(3-hydroxy-2-phosphonylmethoxypropyl)-2,6-diaminopurine [(S)-HPMPDAP], (S)-1-(3-hydroxy-2-phosphonyl-methoxypropyl)cytosine [(S)-HPMPC, or cidofivir], and (2 S,4S)-1-[2-(hydroxymethyl)-1,3-dioxolan-4-yl]-5-iodouracil (L-5-IoddU).

In one embodiment, the compounds of the invention may be employed together with at least one other antiviral agent chosen from polymerase inhibitors.

In addition, compounds according to the present invention can be administered in combination or alternation with one or more anti-retrovirus, anti-hepatitis B virus (HBV), anti-hepatitis C virus (HCV), anti-EBV or anti-herpetic agent or interferon, anti-cancer or antibacterial agents, including other compounds of the present invention. Certain compounds according to the present invention may be effective for enhancing the biological activity of certain agents according to the present invention by reducing or otherwise altering the metabolism, catabolism or inactivation of other compounds and as such, are co-administered for this intended effect.

Additionally, an anti-proliferative agent can be administered in combination or alternation therapy for the present invention. The anti-proliferative agent, as used herein, is any agent that decreases the hyperproliferation of cells. Any of the anti-proliferative agents listed below, or any other such agent known or discovered to exhibit an anti-proliferative effect can be used in accordance with this invention.

Proliferative disorders are currently treated by a variety of classes of compounds including alkylating agents, antimetabolites, natural products, enzymes, biological response modifiers, miscellaneous agents, hormones and antagonists, such as those listed below. Examples, include, but are not limited to:

Monoclonal Antibodies

Monoclonal antibodies directed to proliferating cells such as Rituximab (anti-CD20) for B-cell tumors.

Alkylating Agents

Nitrogen mustards: mechlorethamine (Hodgkins disease, non-Hodgkins lymphomas), Cyclophosphamide Ifosfamide (acute and chronic lymphocytic leukemias, Hodgkins disease, non-Hodgkins lymphomas, multiple myeloma, neuroblastoma, breast, ovary, lung, Wilms' tumor, cervix, testis, soft-tissue sarcomas), melphalan (L-sarcolysin) (multiple myeloma, breast, ovary), chlorambucil (chronic lymphocytic leukemia, primary macroglobulinemia, Hodgkins disease, non-Hodgkins lymphomas).

Ethylenimines and methylmelamines: hexamethylmelamine (ovary), Thiotepa (bladder, breast, ovary).

Alkyl sulfonates: busulfan (chronic granuloytic leukemia).

Nitrosoureas: Carmustine (BCNU) (Hodgkin's disease, non-Hodgkins lymphomas, primary brain tumors, multiple myeloma, malignant melanoma), Lomustine (CCNU) (Hodgkins disease, non-Hodgkins lymphomas, primary brain tumors, small-cell lung), Semustine (methyl-CCNU) (primary brain tumors, stomach, colon), Streptozocin (streptozocin) (malignant pancreatic insulinoma, malignant carcinoin).

Triazenes: Dacarbazine (DTIC; dimethyltriazenoimidazolecarboxamide) (malignant melanoma, Hodgkins disease, soft-tissue sarcomas).

Anti-metabolites

Folic acid analogs: methotrexate (amethopterin) (acute lymphocytic leukemia, choriocarcinoma, mycosis fungoides, breast, head and neck, lung, osteogenic sarcoma).

Pyrimidine analogs: fluorouracil (5-fluorouracil; 5-FU) Floxuridine (fluorodeoxyuridine; FUdR) (breast, colon, stomach, pancreas, ovary, head and neck, urinary bladder, premalignant skin lesions) (topical), Cytarabine (cytosine arabinoside) (acute granulocytic and acute lymphocytic leukemias).

Purine analogs and related inhibitors: mercaptopurine (6-mercaptopurine; 6-MP) (acute lymphocytic, acute granulocytic and chronic granulocytic leukemia), thioguanine (6-thioguanine: TG) (acute granulocytic, acute lymphocytic and chronic granulocytic leukemia), Pentostatin (2'-deoxycyoformycin) (hairy cell leukemia, mycosis fungoides, chronic lymphocytic leukemia).

Vinca alkaloids: Vinblastine (VLB) (Hodgkins disease, non-Hodgkins lymphomas, breast, testis), vincristine (acute lymphocytic leukemia, neuroblastoma, Wilms' tumor, rhabdomyosarcoma, Hodgkins disease, non-Hodgkins lymphomas, small-cell lung).

Epipodophyl-lotoxins: etoposide (testis, small-cell lung and other lung, breast, Hodgkins disease, non-Hodgkins lymphomas, acute granulocytic leukemia, Kaposi's sarcoma), teniposide (testis, small-cell lung and other lung, breast, Hodgkins disease, non-Hodgkins lymphomas, acute granulocytic leukemia, Kaposi's sarcoma).

Natural Products

Antibiotics: dactinomycin (actinonmycin D) (choriocarcinoma, Wilms' tumor rhabdomyosarcoma, testis, Kaposi's sarcoma), daunorubicin (daunomycin; rubidomycin) (acute granulocytic and acute lymphocytic leukemias), doxorubicin (soft tissue, osteogenic, and other sarcomas; Hodgkins disease, non-Hodgkins lymphomas, acute leukemias, breast, genitourinary thyroid, lung, stomach, neuroblastoma), bleomycin (testis, head and neck, skin and esophagus lung, and genitourinary tract, Hodgkins disease, non-Hodgkins lymphomas), plicamycin (mithramycin) (testis, malignant hypercalcema), mitomycin (mitomycin C) (stomach, cervix, colon, breast, pancreas, bladder, head and neck).

Enzymes: L-asparaginase (acute lymphocytic leukemia).

Biological response modifiers: interferon-alfa (hairy cell leukemia, Kaposi's sarcoma, melanoma, carcinoid, renal cell, ovary, bladder, non Hodgkins lymphomas, mycosis fungoides, multiple myeloma, chronic granulocytic leukemia), interferon-gamma, IL-2 and IL-12.

Hormones and Antagonists

Estrogens: Diethylstibestrol ethinyl estradiol (breast, prostate)

Antiestrogen: Tamoxifen (breast).

Androgens: Testosterone propionate Fluxomyesterone (breast).

Antiandrogen: Flutamide (prostate).

Gonadotropin-Releasing Hormone Analog: Leuprolide (prostate).

Miscellaneous Agents

Platinum coordination complexes: cisplatin (cis-DDP) carboplatin (testis, ovary, bladder, head and neck, lung, thyroid, cervix, endometrium, neuroblastoma, osteogenic sarcoma).

Anthracenedione: mixtozantrone (acute granulocytic leukemia, breast).

Substituted Urea: hydroxyurea (chronic granulocytic leukemia, polycythemia vera, essential thrombocytosis, malignant melanoma).

Methylhydrazine derivative: procarbazine (N-methylhydrazine, MIH) (Hodgkins disease).

Adrenocortical suppressant: miotane (o,p'-DDD) (adrenal cortex), aminoglutethimide (breast).

Adrenorticosteriods: prednisone (acute and chronic lymphocytic leukemias, non-Hodgkins lymphomas, Hodgkins disease, breast).

Progestins: hydroxprogesterone caproate, medroxyprogesterone acetate, megestrol acetate (endometrium, breast).

Demethylating agents: azacytidine

PKC activators: bryostatins

Differentiating agents: butyrates, retinoic acid and related retinoids

Microtubule inhibitors: taxols and taxanes

Topoisomerase inhibitors: topotecan

Miscellaneous: valproic Acid, HMBA, NF-kappaB Inhibitors.

Radiation Therapy

Both the CD and HSV-TK systems additionally sensitize cancer cells to radiation, providing possible combination therapies to control advanced tumors (Kim J H, Kim S H, Kolozsvary A, Brown S L, Lim O B, Freytag S O. Selective enhancement of radiation response of herpes simplex virus thymidine kinase transduced 9L gliosarcoma cells in vitro and in vivo by antiviral agents. Int J Radiat Oncol Biol Phys 33: 861–868, 1995; Khil M. S.; Kim J. H.; Mullein C. A.; Kim S. H.; Freytag S. O. Radiosensitization by 5-fluorocytosine of human colorectal carcinoma cells in culture transduced with cytosine deaminase gene. Clinical Cancer Res.2, 53–57; 1996). Therefore, in one embodiment of the invention, the compounds are administered in combination or alternation with radiation therapy, i.e., as used herein, radiation is included as a viable effective antiproliferative agent.

V Pharmaceutical Compositions

Host, including humans, infected with an Epstein-Barr virus, or a gene fragment thereof, can be treated by administering to the patient an effective amount of the selected compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

A preferred dose of the compound will be in the range from about 1 to 50 mg/kg, preferably 1 to 20 mg/kg, of body weight per day, more generally 0.1 to about 100 mg per kilogram body weight of the recipient per day. The effective dosage range of the pharmaceutically acceptable salts and prodrugs can be calculated based on the weight of the parent nucleoside to be delivered. If the salt or prodrug exhibits activity in itself, the effective dosage can be estimated as above using the weight of the salt or prodrug, or by other means known to those skilled in the art.

The compound is conveniently administered in unit any suitable dosage form, including but not limited to one containing 7 to 3000 mg, preferably 70 to 1400 mg of active ingredient per unit dosage form. An oral dosage of 50–1000 mg is usually convenient.

Ideally the active ingredient should be administered to achieve peak plasma concentrations of the selected compound of from about 0.2 to 70 M, preferably about 1.0 to 10 M. This may be achieved, for example, by the intravenous injection of a 0.1 to 5% solution of the active ingredient, optionally in saline, or administered as a bolus of the active ingredient.

The concentration of selected compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the selected compound is oral. Oral compositions will generally include an inert diluent or an edible carrier. They may be enclosed in gelatin capsules or compressed into tablets. For the purpose of oral therapeutic administration, the selected compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the selected compounds, sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories or other antivirals, including other nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetra acetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the selected compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (incorporated by reference). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the selected compound or its monophosphate, diphosphate, and/or triphosphate derivatives is then introduced into the container. The container is then swirled by hand to free lipid material from the sides of the container and to disperse lipid aggregates, thereby forming the liposomal suspension.

VI Processes for the Preparation of Selected Compounds

The compounds according to the present invention are produced by synthetic methods that are readily known to those of ordinary skill in the art and include various chemical synthetic methods.

A method for the facile preparation of 5-substituted uracil nucleosides is also provided.

The 5-substitued uracil nucleosides disclosed herein can be prepared as described in detail below, or by other assays known to those skilled in the art. For example, such methods are described in the following references: Bergstrom D. E., Ruth J. L. (1981) U.S. Pat. No. 4,247,544; De Clercq E. D. A., Verhelst G. A., Jones A. S., Walker R. T. (1984) U.S. Pat. No. 4,382,925; Jones A. S., Walker R. T., De Clercq E. D. A., Barr P. J. (1984) U.S. Pat. No. 4,424,211; Sakata S., Machida H. (1985) U.S. Pat. No. 4,542,210; Walker R. T., Coe P. L. (1994) U.S. Pat. No. 5,356,882; Spector T., Porter D. J. T., Rahim S. G. (2001) U.S. Pat. No. 6,177,436; Robins M. J., Barr P. J. (1983) *J. Org. Chem.* 48, 1854–1862; Ogilvie K. K., Hamilton R. G., Gillen M. F., Radatus B. K. (1984) *Can. J. Chem.* 62, 16–21; Watanabe K. A., Su T.-L., Reichman U., Greenberg N., Lopez C., Fox J. J. (1984) *J. Med. Chem.* 27, 91–94; McGee D. P. C., Martin J. C., Smee D. F., Matthews T. R., Verheyden P. H. (1985) *J. Med. Chem.* 28, 1242–1245; Beauchamp L. M., Serling B. L., Kelsey J. E., Biron K. K., Collins P., Selway J., Lin J.-C., Schaeffer H. J. (1988) *J. Med. Chem.* 31, 144–149; Balzarini J., Baumgartner H., Bodenteich M., De Clercq E., Griengl H. (1989) *J. Med. Chem.* 32, 1861–1865; Dyson M. R., Coe P. L., Walker R. T. (1991) *J. Med. Chem.* 34, 2782–2786; Lin T.-S., Luo M.-Z., Liu M.-C. (1995) *Tetrahedron*, 51, 1055–1068; Rahim S. G., Trivedi N., Bogunovic-Batchelor M. V., Hardy G. W., Mills G., Selway J. W. T., Snowden W., Littler E., Coe P. L., Basnak I., Whale R. F., Walker R. T. (1996) *J. Med. Chem.* 39, 789–795; Ma T., Pai S. B., Zhu Y. L., Lin J. S., Shanmuganathan K., Du J., Wang C., Kim H., Newton M. G., Cheng Y. C., Chu C. K. (1996) *J. Med. Chem.* 39, 2835–2843; Basnak I., Otter G. P., Duncombe R. J., Westwood N. B., Pietrarelli M., Hardy G. W., Mills G., Rahim S. G., Walke R. T. (1998) *Nucleosides and Nucleotides*, 17, 29–38; Choi Y., Li L., Grill S., Gullen E., Lee C. S., Gumina G., Tsujii E., Cheng Y.-C., Chu C. K. (2000) *J. Med. Chem.* 43, 2538–2546.

VII Processes for the Preparation of Transfected Cell Lines with EBV-TK

The EBV-TK gene can be cloned into an expression vector by any means known in the art. In particular, EBV-TK gene from the viral strain B-958 can be cloned into the vector pCMV as described by Gustafson E. A. et al. *Antimicrob. Agents Chemother.* 1998, 42(11), 2923–31. The vector can then be transferred using any known reagent in the art into any desired viable cell line, for example, using Lipofectamine reagent to transfect the vector into human cell lines.

VIII Gene Therapy

Eukaryotic cells that may be transduced with vectors (infectious viral particles or plasmids) containing a gene for the expression of EBV-TK include, but are not limited to, primary cells, such as primary nucleated blood cells, such as leukocytes, granulocytes, monocytes, macrophages, lymphocytes (including T-lymphocytes and B-lymphocytes), totipotent stem cells, and tumor infiltrating lymphocytes (TIL cells); bone marrow cells; endothelial cells; epithelial cells; keratinocytes; stem cells; hepatocytes, including hepatocyte precursor cells; hepatocytes, including hepatocyte precursor cells; fibroblasts; mesenchymal cells; mesothelial cells; parenchymal cells, or other cells of tumor derivation.

In one embodiment, the cells may be targeted to a specific site, whereby the cells function as a therapeutic at such site. Alternatively, the cells may be cells that are not targeted to a specific site, and such cells function as a systemic therapeutic.

Transduced cells may be used, for example, in the treatment of abnormal cellular proliferation in a host, and in particular a human, by introducing to host cells, such as blood cells that specifically "target" to a site of abnormal cellular proliferation (for example a tumor), that have been removed from a cancer patient and expanded in culture, transduced with a vector (infectious viral particles or plasmid) in accordance with the present invention which contain genes that encode EBV-TK. Optionally, the vector can also contain genes that enhance the anti-tumor effects of the cell. The cells can be expanded in number before or after transduction with the vector containing the desired genes. Thus, the procedure is performed in such a manner that upon injection into the patient, the transformed cells will produce EBV-TK in the patient's body, preferably at the site of the tumor itself.

The gene of the present invention carried by the transduced cells specifically comprises the sequence for EBV-TK, but can be also comprise any sequence that directly or indirectly enhances the therapeutic effects of the cells. The gene carried by the transduced cells can also include sequences that allow the transduced cells to exert a therapeutic effect that it would not ordinarily have, such as a gene encoding a clotting factor useful in the treatment of hemophilia. The gene can encode one or more products having therapeutic effects. Examples of suitable genes include those that encode cytokines such as TNF, GMCSF, interleukins (interleukins 1–18), interferons (alpha, beta, gamma-interferons), T-cell receptor proteins and Fe receptors for antigen-binding domains of antibodies, such as immunoglobulins. Additional examples of suitable genes include genes that modify cells to "target" to a site in the body to which the cells would not ordinarily target, thereby making possible the use of the cell's therapeutic properties at that site. For example, blood cells such as TIL cells can be modified, for example, by introducing a Fab portion of a monoclonal antibody into the cells, thereby enabling the cells to recognize a chosen antigen. Likewise, blood cells having therapeutic properties can be used to target, for example, a tumor, that the blood cells would not normally target. Other genes useful in cancer therapy can be used to encode chemotactic factors that cause an inflammatory response at a specific site, thereby having a therapeutic effect. Other examples of suitable genes include genes encoding soluble CD4 that is used in the treatment of AIDS and genes encoding alpha-1-antitrypsin, which is useful in the treatment of emphysema caused by alpha-1-antitrypsin deficiency.

IX Gene Therapy Vectors

In general, a gene cannot be directly inserted into a cell. It must be delivered to the cell using a carrier known as a "vector." The most common types of vectors used in gene therapy are viruses. Scientists use viruses because they have a unique ability to attach to or enter a cell's DNA. Viruses used as vectors in gene therapy are genetically disabled; they are unable to reproduce themselves, though they can replicate coordinately with the cellular DNA. Many gene therapy clinical trials rely on mouse retroviruses to deliver the desired gene. Other viruses used as vectors include adenoviruses, adeno-associated viruses, poxviruses and the herpes virus.

For example, cells from the patient are removed and grown in the laboratory. The cells are exposed to the virus that is carrying the desired gene. The virus enters the cells, and the desired gene becomes part of the cells' DNA. The cells grow in the laboratory and are then returned to the patient. This type of gene therapy is called ex vivo, which means "outside the body." The gene is transferred into the patient's cells while the cells are outside the patient's body. In other studies, vectors (viral, bacterial) or liposomes (fatty particles) are used to deliver the desired gene to cells in the patient's body. This form of gene therapy is called in vivo, because the gene is transferred to cells inside the patient's body.

When these gene delivery vectors are used to carry genes into the body, they might alter more than the intended cells. Another danger is that the new gene might be inserted in the wrong location in the DNA, possibly causing cancer or other damage. In addition, when using in vivo gene delivery systems, there is a chance that the DNA could be introduced into reproductive cells, producing inheritable changes.

Other concerns include the possibility that transferred genes could be "overexpressed," producing so much of a protein as to be harmful; that a pathogen vector could cause inflammation or an immune reaction; and in the case where a virus is used as the vector, it could be transmitted from the patient to other individuals or into the environment.

There are many vectors known in the art. Any known vector can be used in the present invention. In a preferred embodiment of the present invention, the vector can target a specific cell type for specific gene delivery.

Adenoviral Vectors

Any of the adenoviral vectors can be used to transfect cells and/or cell lines with EBV-TK. Adenoviruses are non-enveloped viruses containing a linear double stranded DNA genome. While there are over 40 serotype strains of adenovirus, most of which cause benign respiratory tract infections in humans, subgroup C serotypes 2 or 5 are predominantly used as vectors. The life cycle does not normally involve integration into the host genome, rather they replicate as episomal elements in the nucleus of the host cell and consequently there is no risk of insertional mutagenesis. The wild type adenovirus genome is approximately 35 kb of which up to 30 kb can be replaced with foreign DNA (Smith A. E. (1995) Viral vectors in gene therapy. Annual Review of Microbiology 49: 807–838; Verma I. M. & Somia N. (1997) Gene therapy—promises, problems and prospects. Nature 389: 239–242). There are four early transcriptional units (E1, E2, E3 and E4) that have regulatory functions, and a late transcript, which codes for structural proteins. Progenitor vectors have either the E1 or E3 gene inactivated, with the missing gene being supplied in trans either by a helper virus, plasmid or integrated into a helper cell genome (human fetal kidney cells, line 293; Graham F. L., Smiley J., Russell W. L., Nairn R. (1997) Characterization of a human cell line transformation by DNA from adenovirus 5. Gen. Virol. 36: 59–72). Second generation vectors additionally use an E2a temperature sensitive mutant (Engelhardt J. F., Litsky L., Wilson, J. M. (1994) Prolonged gene expression in cotton rat lung with recombinant adenoviruses defective in E2a. Human Gene Therapy 5: 1217–1229) or an E4 deletion (Armentano D., Zabner J., Sacks C., Sookdeo C. C., Smith M. P., St. George J. A., Wadsworth S. C., Smith A. E., Gregory R. J. (1997) Effect of the E4 region on the presistence of transgene expression from adenovirus vectors. J. Virol. 71: 2408–2416). The most recent "gutless" vectors contain only the inverted terminal repeats (ITRs) and a packaging sequence around the transgene, all the necessary viral genes being provided in trans by a helper virus (Chen H., Mack L. M., Kelly R., Ontell M., Kochanek S., Clemens P. R. (1997) Persistence in muscle of an adenoviral vector that lacks all viral genes. Proc. Natl. Acad. Sci. USA 94: 1645–1650).

Adenoviral vestors are very efficient at transducing target cells in vitro and vivo, and can be produced at high titres ($>10^{11}$/mL). With the exception of Geddes et al. (Geddes B. J., Harding T. C., Lightman S. L., Uney J. B. (1997) Long term gene therapy in the CNS: Reversal of hypothalamic diabetes insipidus in the Brattleboro rat by using an adenovirus expressing arginine vasopressin. Nature Medicine 3: 1402–1404), who showed prolonged transgene expression in rat brains using an E1 deletion vector, transgene expression in vivo from progenitor vectors is typically transient (Verma I. M. & Somia N. (1997) Gene therapy—promises, problems and prospects. Nature 389: 239–242). Following intravenous injection, 90% of the administered vector is degraded in the liver by a non-immune mediated mechanism (Worgall S., Wolff G., Falck-Pedersen E., Crystal R. G. (1997) Innate immune mechanisms dominate elimination of adenoviral vectors following in vivo administration. Human Gene Therapy 8: 37–44). Thereafter, an MHC class I restricted immune response occurs, using CD8+ CTLs to eliminate virus infected cells and CD4+ cells to secrete IFN-alpha which results in anti-adenoviral antibody (Yang Y., Wilson J. M. (1995) Clearance of adenovirus-infected hepatocytes by MHC class I restricted CD4+ CTLs in vivo. J. Immmunol. 155: 2564–2569). Alteration of the adenoviral vector can remove some CTL epitopes, however the epitopes recognized differ with the host MHC haplotype (Sparer T. E., Wynn S. G., Clark D. J., Kaplan J. M., Cardoza L. M., Wadsworth S. C., Smith A. E., Gooding L. R. (1997) Generation of cytotoxic T lymphocytes against immunorecessive epitopes after multiple immunizations with adenovirus vectors is dependent on haplotype. J. Virol. 71: 2277–2284; Jooss K., Ertl H. C. J., Wilson J. M. (1998) Cytotoxic T-lymphocyte target proteins and their histocompatibility complex class I restriction in response to adenovirus vectors delivered to mouse liver. J. Virol. 72: 2945–2954). The remaining vectors, in those cells that are not destroyed, have their promoter inactivated (Armentano D., Zabner J., Sacks C., Sookdeo C. C., Smith M. P., St.

George J. A., Wadsworth S. C., Smith A. E., Gregory R. J. (1997) Effect of the E4 region on the persistence of transgene expression from adenovirus vectors. J. Virol. 71: 2408–2416) and persisting antibody prevents subsequent administration of the vector.

Approaches to avoid the immune response involving transient immunosuppressive therapies have been successful in prolonging transgene expression and achieving secondary gene transfer (Jooss K., Yang Y., Wilson J. M. (1996) Cyclophosphamide diminishes inflammation and prolongs expression following delivery of adenoviral vectors to mouse liver and lung. Human Gene Therapy 7: 1555–1566; Kay M. A., Meuse L., Gown A. M., Linsley P., Hollenbaugh D., Aruffo A., Ochs H. D., Wilson C. B. (1997) Transient immunomodulation with anti-CD40 ligand and CTLA41g enhances presistence and secondary adenovirus-mediated gene transfer into mouse liver. Proc. Natl. Acad. Sci. USA 94: 4686–4691). A less interventionist method has been to induce oral tolerance by feeding the host UV inactivated vector (Kagami H., Atkinson J. C., Michalek S. M., Handelman B., Yu S., Baum B. J., O'Connell B. (1998) Repetitive adenovirus administration to the parotid gland: role of immunological barriers and induction of oral tolerance. Human Gene Therapy 9: 305–313). However, it is desirable to manipulate the vector rather than the host. Although only replication-deficient vectors are used, viral proteins are expressed at a very low level, which are presented to the immune system. The development of vectors containing fewer genes, culminating in the "gutless" vectors which contain no viral coding sequences, has resulted in prolonged in vivo transgene expression in liver tissue (Schiedner G., Morral N., Parks R. J., Wu Y., Koopmans S. C., Langston C., Graham F. L., Beaudet A. L., Kochanek S. (1998) Genomic DNA transfer with a high-capacity adenovirus vector results in improved in vivo gene expression and decreased toxicity. Nature Genetics 18: 180–183). The initial delivery of large amounts of DNA packaged within adenovirus proteins, the majority of which will be degraded and presented to the immune system may still cause problems for clinical trials. Moreover the human population is heterogeneous with respect to MHC haplotype and a proportion of the population will have been already exposed to the adenoviral strain (Gahry-Sdard H., Molinier-Frenkel V., Le Boulaire C., Saulnier P., Opolon P., Lengange R., Gautier E., Le Cesne A., Zitvogel L., Venet A., Schatz C., Courtney M., Le Chevalier T., Tursz T., Guillet J., Farace F. (1997) Phase I trial of recombinant adenovirus gene transfer in lung cancer. J. Clin. Invest. 100: 2218–2226).

Until recently, the mechanism by which the adenovirus targeted the host cell was poorly understood. Tissue specific expression was therefore only possible by using cellular promoter/enhancers, such as the myosin light chain 1 promoter (Shi Q., Wang Y., Worton R. (1997) Modulation of the specificity and activity of a cellular promoter in an adenoviral vector. Human Gene Therapy 8: 403–410) or the smooth muscle cell SM22a promoter (Kim S., Lin H., Barr E., Chu L., Leiden J. M., Parrnacek M. S. (1997) Transcriptional targeting of replication-defective adenovirus transgene expression to smooth muscle cells in vivo. J. Clin. Invest. 100: 1006–1014), or by direct delivery to a local area (Rome J. J., Shayani V., Newman K. D., Farrell S., Lee S. W., Virmani R., Dicheck D. A. (1994) Adenoviral vector mediated gene transfer into sheep arteries using a double-balloon catheter. Human Gene Therapy 5: 1249–1258). Uptake of the adenovirus particle has been shown to be a two stage process involving an initial interaction of a fiber coat protein in the adenovirus with a cellular receptor or receptors, which include the MHC class I molecule (Hong S. S., Karayan L., Tournier J., Curiel D. T., Boulanger P. A. (1997) Adenovirus type 5 fiber knob binds to MHC class I a2 domain at the surface of human epithelial and B lymphoblastoid cells. EMBO J. 16: 2294–2306) and the Coxsackie virus-adenovirus receptor (Bergelson J. M., Cunningham J. A., Droguett G., Kurt-Jones A. E., Krithivas A., Hong J. S., Horwitz M. S., Crowell R. L., Finberg R. W. (1997) Isolation of a common receptor for Coxsackie virus B viruses and adenoviruses 2 and 5. Science 275: 1320–1323). The penton base protein of the adenovirus particle then binds to the integrin family of cell surface heterodimers (Wickham T. J., Mathias P., Cheresh D. A., Nemerow G. R. (1993) Integrins avb3 and avb5 promote adenovirus internalization but not virus attachment. Cell 73: 309–319) allowing internalization via receptor mediated endocytosis. Most cells express primary receptors for the adenovirus fiber coat protein, however internalization is more selective (Harris J. D. & Lemoine N. R. (1996) Strategies for targeted gene therapy. Trends in Genetics 12: 400–404). Methods of increasing viral uptake include stimulating the target cells to express an appropriate integrin (Davison E., Diaz R. M., Hart I. R., Santis G., Marshall J. F. (1997) Integrin a5b1-mediated adenovirus infection is enhanced by the integrin-activating antibody TS2/16. Journal of Virology 71: 6204–6207) and conjugating an antibody with specificity for the target cell type to the adenovirus (Wickham T. J., Lee G. M., Titus J. A., Titus J. A., Sconocchia G., Bakacs T., Kovesdi I., Segal D. M. (1997b). Targeted adenovirus-mediated gene delivery to T cells via CD3. J. Virol. 71: 7663–7669; Goldman C. K., Rogers B. E., Douglas J. T., Sonsowski B. A., Ying W., Siegal G. P., Baird A., Campain J. A., Curiel D. T. (1997) Targeted gene delivery to Kaposi's sarcoma cells via the fibroblast growth factor receptor. Cancer Res. 57: 1447–1451). The use of antibodies though increases the production difficulties of the vector and the potential risk of activating the complement system. By incorporating receptor binding motifs into the fiber coat protein (Wickham T. J., Tzeng E., Shears II, L. L., Roelvink P. W., Li Y., Lee G. M., Brough D. E., Lizonova A., Kovesdi I. (1997a) Increased in vitro and in vivo gene transfer by adenovirus vectors containing chimeric fiber proteins. J. Virol. 71: 8221–8229) were able to redirect the virus to bind the integrin expressed by damaged endothelial or smooth muscle cells, or heparin sulfate receptors, which are expressed by many cell types.

Adeno-Associated Viral Vectors

Any of the adeno-associated viral vectors can be used to transfect cells and/or cell lines with EBV-TK or KHSV-TK. Adeno-associated viruses (AAV) are non-pathogenic human parvoviruses, dependant on a helper virus, usually adenovirus, to proliferate. They are capable of infecting both dividing and non dividing cells, and in the absence of a helper virus integrate at a specific point of the human host genome (19q13→qter) at a high frequency (Kotin R. M., Siniscalco M., Samulski R. J., Zhu X. D., Hunter L., Laughlin C. A., McLaughlin S., Muzyczka N., Rocchi M., Bems K. I. (1990) Site-specific integration by adeno-associated virus. Proc. Natl. Acad. Sci. USA 87: 2211–2215). The wild type genome is a single stranded DNA molecule, consisting of two genes; rep, coding for proteins which control viral replication, structural gene expression and integration into the host genome, and cap, which codes for capsid structural proteins. At either end of the genome is a 145 bp terminal repeat (TR), containing a promoter.

When used as a vector, the rep and cap genes are replaced by the transgene and its associated regulatory sequences. The total length of the insert cannot greatly exceed 4.7 kb, the length of the wild type genome (Smith A. E. (1995) Viral vectors in gene therapy. Ann. Rev. Microbiol. 49: 807–838). Production of the recombinant vector requires that rep and cap are provided in trans, along with helper virus gene products (E1a, E1b, E2a, E4 and VA RNA from the adenovirus genome). The conventional method is to cotransfect two plasmids, one for the vector and another for rep and cap, into 293 cells infected with adenovirus (Samulski R. J., Chang L., Shenk T. (1989) Helper free stocks of recombinant adeno-associated viruses: normal integration does not require viral gene expression. J. Virol. 63: 3822–3828). This method, however, is cumbersome, low yielding (<$10^4$ particles/ml) and prone to contamination with adenovirus and wild type AAV. One of the reasons for the low yield is the inhibitory effect of the rep gene product on adenovirus replication (Vincent K. A, Piraino S. T., Wadsworth S. C. (1997) Analysis of recombinant adeno-associated virus packaging and requirements for rep and cap gene products. J. Virol. 71: 1897–1905). More recent protocols remove all adenoviral structural genes and use rep resistant plasmids (Xiao X., Li J., Samulski R. J. (1998) Production of high-titer recombinant adeno-associated virus vectors in the absence of helper adenovirus. J. Virol. 72: 2224–2232) or conjugate a rep expression plasmid to the mature virus prior to infection (Fisher K. J., Kelley W. M, Burda J. F., Wilson J. M. (1996) A novel adenovirus-adeno-associated virus hybrid vector that displays efficient rescue and delivery of the AAV genome. Human Gene Therapy 7: 2079–2087).

In the absence of rep, the AAV vector will only integrate at random, as a single provirus or head to tail concatamers, once the terminal repeats have been slightly degraded (Rutledge E. A. & Russell D. W. (1997) Adeno-associated virus vector integration junctions. J. Virol. 71: 8429–8436). Interest in AAV vectors has been due to their integration into the host genome allowing prolonged transgene expression. Gene transfer into vascular epithelial cells (Maeda Y., Ikeda U., Ogasawara Y., Urabe M., Takizawa T., Saito T., Colosi P., Kurtzman G., Shimada K., Ozawa, K. (1997) Gene transfer into vascular cells using adeno-associated virus (AAV) vectors. Cardiovascular Res. 35: 514–521), striated muscle (Fisher K. J., Jooss K., Alston J., Yang Y., Haecker S. E., High K., Pathak R., Raper S. E., Wilson J. M. (1997) Recombinant adeno-associated virus for muscle directed gene delivery. Nature Medicine 3: 306–316; Herzog R. W., Hagstrom J. N., Kung S., Tai S. J., Wilson J. M., Fisher K. J., High K. A. (1997) Stable gene transfer and expression of human blood coagulation factor IX after intramuscular injection of recombinant adeno-associated virus. Proc. Natl. Acad. Sci. USA 94: 5804–5809) and hepatic cells (Snyder R. O., Miao C. H., Patijn G. A., Spratt S. K., Danos O., Nagy D., Gown A. M., Winter B., Meuse L., Cohen L. K., Thompson A. R., Kay, M. A. (1997) Persistent and therapeutic concentrations of human factor IX in mice after hepatic gene transfer of recombinant AAV vectors. Nature Genetics 16: 270–275) has been reported, with prolonged expression when the transgene is not derived from a different species. Neutralizing antibody to the AAV capsid may be detectable, but does not prevent readministration of the vector or shut down promoter activity. It is possibly due to the simplicity of the viral capsid, that the immune response is so muted. As AAV antibodies will be present in the human population this will require further investigation. There has been no attempt to target particular cell types other than by localized vector delivery.

In particular, the adeno-associated vectors disclosed in U.S. Pat. No. 5,693,531, which is hereby incorporated by reference, can be used, including AAVp5neo; pSV-β-galactosidase; TRF169; LZ11; pSP72; pSP72nLacZ; pAdRSV4; pAdRSVnLacZ; AAVrnLac; SV40; pBluescriptSK; pSV40 ori AAV1; and pKMT11.

Retroviral Vectors

Any of the retroviral vectors can be used to transfect cells and/or cell lines with EBV-TK. Retroviruses are a class of enveloped viruses containing a single stranded RNA molecule as the genome. Following infection, the viral genome is reverse transcribed into double stranded DNA, which integrates into the host genome and is expressed as proteins. The viral genome is approximately 10 kb, containing at least three genes: gag (encoding core proteins), pol (encoding reverse transcriptase) and env (encoding the viral envelope protein). At each end of the genome are long terminal repeats (LTRs) which include promoter/enhancer regions and sequences involved with integration. In addition there are sequences required for packaging the viral DNA (psi) and RNA splice sites in the env gene. Some retroviruses contain proto-oncogenes, which when mutated can cause cancers; however, in the production of vectors these are removed. Retroviruses can also transform cells by integrating near a cellular proto-oncogene and driving inappropriate expression from the LTR, or by disrupting a tumor suppresser gene. Such as event, termed insertional mutagenesis, though extremely rare, could still occur when retroviruses are used as vectors.

Retroviral vectors are most frequently based upon the Moloney murine leukemia virus (Mo-MLV), which is an amphotrophic virus, capable of infecting both mouse cells, enabling vector development in mouse models, and human cells, enabling human treatment. The viral genes (gag, pol and env) are replaced with the transgene of interest and expressed from plasmids in the packaging cell line. Because the non-essential genes lack the packaging sequence (psi) they are not included in the virion particle. To prevent recombination resulting in replication-competent retroviruses, all regions of homology with the vector backbone should be removed and non-essential genes should be expressed in at least two transcriptional units (Markowitz D., Goff S., Bank A. (1988) A safe packaging line for gene transfer: separating viral genes on two different plasmids. J. Virol. 62: 1120–1124). Even so, replication-competent retroviruses do arise at a low frequency.

The essential regions include the 5'- and 3'-LTRs, and the packaging sequence lying downstream of the 5'-LTR. Transgene expression can either be driven by the promoter/enhancer region in the 5'-LTR, or by alternative viral (e.g., cytomegalovirus, Rous sarcoma virus) or cellular (e.g., beta actin, tyrosine) promoters. Mutational analysis has shown that up to the entire gag coding sequence and the immediate upstream region can be removed without effecting viral packaging or transgene expression (Kim S. H., Yu S. S., Park J. S, Robbins P. D, An C. S., Kim S. (1998) Construction of retroviral vectors with improved safety, gene expression, and versatility. J. Virol. 72: 994–1004). However the exact positioning of the transgene start codon and small alterations of the 5'-LTR influence transgene expression (Rivire I., Brose K., Mulligan R. C. (1995) Effects of retroviral vector design on expression of human adenosine deaminase in murine bone marrow transplant recipients engrafted with genetically modified cells. Proc. Natl. Acad. Sci. USA 92: 6733–6737). To aid identification of transformed cells selectable markers, such as neomycin and beta-galactosidase, can be included and transgene expression can be improved by the addition of internal ribosome-binding sites (Saleh M. (1997) A retroviral vector that allows co-expression of two genes and the versatility of alternate selection markers. Human Gene Therapy 8: 979–983). The available carrying capacity for retroviral vectors is approximately 7.5 kb (Verma I. M. & Somia N. (1997) Gene therapy—promises, problems and prospects. Nature 389: 239–242), which is too small for some genes, even if the cDNA is used.

The retroviral envelope interacts with a specific cellular protein to determine the target cell range. Altering the env gene or its product has proved a successful means of manipulating the cell range. Approaches have included direct modifications of the binding site between the envelope protein and the cellular receptor, however these approaches tend to interfere with subsequent internalization of the viral particle (Harris J. D. & Lemoine N. R. (1996) Strategies for targeted gene therapy. Trends in Genetics 12: 400–404). By replacing a portion of the env gene with 150 codons from the erythropoietin protein (EPO), Kasahara et al. (Kasahara N., Dozy A. M., Kan Y. W. (1994) Tissue-specific targeting of retroviral ligand-receptor interactions. Science 266: 1374–1376) were able to target EPO receptor bearing cells with high affinity. Coupling an antibody to the viral particle with affinity for a second cell specific antibody via a streptavodin bridge, improves viral uptake, but internalization tends to lead to viral degradation (Roux P., Jeanteur P., Piechaczyk M. (1989) A versatile and potentially general approach to the targeting of specific cell types by means of major histocompatibility complex class I and class II antigens by mouse ecotropic murine leukemia virus-derived viruses. Proc. Natl. Acad. Sci. USA 86: 9079–9083). Neda et al. (Neda H., Wu C. H., Wu G. Y. (1991) Chemical modification of an ecotropic murine leukemia virus results in redirection of its target cell specificity. J. Biol. Chem. 266: 14143–14146) treated viral particles with lactose, which resulted in uptake by cells, principally hepatocytes, expressing asialoglycoprotein receptors. Subsequently, there was efficient viral transgene expression, possibly due to acidification of the endosome, allowing fusion of the viral envelope with the endosome membrane.

Viruses differ with respect to their tropisms; therefore, by replacing the env gene with that of another virus, the host range can be extended, in a technique known as pseudotyping. Vesicular stomatitis virus G protein has been included in Mo-MLV derived vectors (Burns J. C., Matsubara T., Lozinski G., Yee J., Freidmann T., Washabaugh C. H., Tsonis P. A. (1994) Pantropic retroviral vector-mediated gene transfer, integration, and expression in cultured newt limb cells. Dev. Biol. 165: 285–289), which are also more stable when purified by ultracentrifugation. Recently, Qing et al. (Qing K., Bachelot T., Mukherjee P., Wang X., Peng L., Yoder M. C., Leboulch P., Srivastava A. (1997) Adeno-associated virus type 2-mediated transfer of ecotropic retrovirus receptor cDNA allows ecotropic retroviral transduction of established and primary human cells. J. Virol. 71: 5663–5667) improved transduction into numerous cell lines by first treating the recipient cells with an adeno-associated vector (discussed below) expressing the cellular receptor for retroviral envelope protein.

A requirement for retroviral integration and expression of viral genes is that the target cells should be dividing. This limits gene therapy to proliferating cells in vivo or ex vivo, whereby cells are removed from the body, treated to stimulate replication and then transduced with the retroviral vector, before being returned to the patient. When treating cancers in vivo, tumor cells are preferentially targeted (Roth J. A., Nguyen D., Lawrence D. D., Kemp B. L., Carrasco C. H., Ferson D. Z., Hong W. K., Komaki R., Lee J. J., Nesbitt J. C., Pisters K. M. W., Putnam J. B., Schea R., Shin D. M., Walsh G. L., Dolormente M. M., Han C. I., Martin F. D., Yen N., Xu K., Stephens L. C., McDonnell T. J., Mukhopadhyay T., Cai D. (1996). Retrovirus mediated wild-type p53 gene transfer to tumors of patients with lung cancer. Nature Medicine 2: 985–991; Tait D. L., Obermiller P. S., Redlin-Frazier S., Jensen R. A., Welcsh P., Dann J., King M, Johnson D. H., Holt J. T. (1997). A phase I trial of retroviral BRCA1sv gene therapy in ovarian cancer. Clin. Cancer Res. 3: 1959–1968). However, ex vivo cells can be more efficiently transduced, because of exposure to higher virus titers and growth factors (Glimm H., Kiem H. P., Darovsky B., Storb R., Wolf J., Diehl V., Mertelsmann R., Kalle C. V. (1997). Efficient gene transfer in primitive CD34+/CD38lo human bone marrow cells reselected after long term exposure to GALV-pseudotyped retroviral vector. Human Gene Therapy 8: 2079–2086). Furthermore ex vivo-treated tumor cells will associate with the tumor mass and can direct tumoricidal effects (Oldfield E. H. & Ram Z. (1995) Intrathecal gene therapy for the treatment of leptomeningeal carcinomatosis. Human Gene Therapy 6: 55–85; Abdel-Wahab Z., Weltz C., Hester D., Pickett N., Vervaert C., Barber J. R., Jolly D., Seigler H. F. (1997) A phase I clinical trial of immunotherapy with interferon-gamma gene-modified autologous melanoma cells. Cancer 80: 401–412).

Though transgene expression is usually adequate in vitro and initially in vivo, prolonged expression is difficult to attain. Retroviruses are inactivated by c1 complement protein and an anti-alpha galactosyl epitope antibody, both present in human sera (Rother P. R., William L. F., Springhom J. P., Birks W. C., Sandrin M. S., Squinto S. P., Rollins S. A. (1995) A novel mechanism of retrovirus inactivation in human serum mediated by anti-a-galactosyl natural antibody. J. Exp. Med. 182: 1345–1355; Rollins S. A., Birks C. W., Setter E., Squinto S, P., Rother R. P. (1996) Retroviral vector producer cell killing in human serum is mediated by natural antibody and complement: strategies for evading the humoral immune response. Human Gene Therapy 7: 619–626). Transgene expression is also reduced by inflammatory interferons, specifically IFN-alpha and IFN-gamma acting on viral LTRs (Ghazizadeh S., Carroll J. M., Taichman L. B. (1997) Repression of retrovirus-mediated transgene expression by interferons: implications for gene therapy. J. Virol. 71: 9163–9169). As the retroviral genome integrates into the host genome, it is most likely that the viral LTR promoters are inactivated; therefore, one approach has been to use promoters for host cell genes, such as tyrosine (Diaz R. M., Eisen T., Hart I. R., Vile R. G. (1998) Exchange of viral promoter/enhancer elements with regulatory sequences generated targeted hybrid long terminal repeat vectors for gene therapy of melanoma. J. Virol. 72: 789–795). Clearly this is an area where continued research is needed.

Lentiviruses are a subclass of retroviruses that are able to infect both proliferating and non-proliferating cells. They are considerably more complicated than simple retroviruses, containing an additional six proteins, tat, rev, vpr, vpu, nef and vif. Current packaging cell lines have separate plasmids for a pseudotype env gene, a transgene construct, and a packaging construct supplying the structural and regulatory genes in trans (Naldini L., Blmer U., Gallay P., Ory D., Mulligan R., Gage F. H., Verma I. M., Trono D. (1996) In vivo gene delivery and stable transduction of non-dividing cells by a lentiviral vector. Science 272: 263–267). Early results using marker genes have been promising, showing prolonged in vivo expression in muscle, liver and neuronal tissue (Blmer U., Naldini L., Kafri T., Trono D., Verma I. M., Gage F. H. (1997) Highly efficient and sustained gene transfer in adult neurons with a lentivirus vector. J. Virol. 71: 6641–6649; Miyoshi H., Takahashi M., Gage F. H., Verma I. M. (1997) Stable and efficient gene transfer into the retina using an HIV-based lentiviral vector. Proc. Natl. Acad. Sci. USA 94: 10319–10323; Kafri T., Blmer U., Peterson D. A., Gage F. H., Verma I. M. (1997) Sustained expression of genes delivered into liver and muscle by lentiviral vectors. Nature Genetics 17: 314–317). Interestingly the transgenes are driven by an internally engineered cytomegalovirus promoter, which unlike the situation in MoMLV vectors, is not inactivated. This may be due to the limited inflammatory response to vector injection, which was equal in magnitude to the saline control (Blmer U., Naldini L., Kafri T., Trono D., Verma I. M., Gage F. H. (1997) Highly efficient and sustained gene transfer in adult neurons with a lentivirus vector. J. Virol. 71: 6641–6649).

The lentiviral vectors used are derived from the human immunodeficiency virus (HIV) and are being evaluated for safety, with a view to removing some of the non-essential regulatory genes. Mutants of vpr and vif are able to infect neurons with reduced efficiency, but not muscle or liver cells (Blmer U., Naldini L., Kafri T., Trono D., Verma I. M., Gage F. H. (1997) Highly efficient and sustained gene transfer in adult neurons with a lentivirus vector. J. Virol. 71: 6641–6649; Kafri T., Blmer U., Peterson D. A., Gage F. H., Verma I. M. (1997) Sustained expression of genes delivered into liver and muscle by lentiviral vectors. Nature Genetics 17: 314–317).

In a particular embodiment, the retroviral vectors pLXIN, pSIR, pLXSH, pLNCX, pLAPSN, pFB and pFB-Neo are used.

Herpes Simplex Viral Vectors

Any of the herpes simplex viral vectors can be used to transfect cells and/or cell lines with EBV-TK. Herpes simplex virus type 1 (HSV-1) is a human neurotropic virus; consequently interest has largely focused on using HSV-1 as a vector for gene transfer to the nervous system. Wild-type HSV-1 virus is able to infect neurons and either proceed into a lytic life cycle or persist as an intranuclear episome in a latent state. Latently infected neurons function normally and are not rejected by the immune system. Though the latent virus is transcriptionally almost silent, it does possess neuron-specific promoters that are capable of functioning during latency. Antibodies to HSV-1 are common in the human population; however complications due to herpes infection, such as encephalitis, are very rare.

The viral genome is a linear, double-stranded DNA molecule of 152 kb. There are two unique regions, long and short (termed UL and US) which are linked in either orientation by internal repeat sequences (IRL and IRS). At the non-linker end of the unique regions are terminal repeats (TRL and TRS). There are up to 81 genes (Marconi P., Krisky D., Oligino T., Poliani P. L., Ramakrishnan R., Goins W. F., Fink D. A., Glorioso J. C. (1996) Replication-defective herpes simplex virus vectors for gene transfer in vivo. Proc. Natl. Acad. Sci. USA 93: 11319–11320), of which about half are not essential for growth in cell culture. Once these non-essential genes have been deleted, 40–50 kb of foreign DNA can be accommodated within the virus (Glorioso J. C., DeLuca N. A., Fink D. J. (1995) Development and application of herpes simplex virus vectors for human gene therapy. Annual Review of Microbiology 49: 675–710). Three main classes of HSV-1 genes have been identified: the immediate-early (IE or alpha) genes, early (E or beta) genes, and late (L or gamma) genes.

Following infection in susceptible cells, lytic replication is regulated by a temporally coordinated sequence of gene transcription. Vmw65 (a tegument structural protein) activates the immediate early genes (IP0, ICP4, ICP22, ICP27 and ICP477) that are transactivating factors allowing the production of early genes. The early genes encode proteins for nucleotide metabolism and DNA replication. Late genes are activated by the early genes and encode structural proteins. The entire cycle takes less than 10 h and invariably results in cell death.

The molecular events leading to the establishment of latency have not been fully determined. Gene expression during latency is driven by the latency associated transcripts (LATs) located in the IRL region of the genome. Two LATs (2.0 and 1.5 kb) are transcribed in the opposite direction to the IE gene ICP0. LATs have a role in HSV-1 reactivation from latency (Steiner I., Spivack J. G., Lirette R. P., Brown S. M., MacLean A. R., Subak-Sharpe J. H., Fraser N. W. (1989) Herpes simplex virus type 1 latency associated transcripts are evidently not essential for latent infection. EMBO Journal 8: 505–511) and the establishment of latency (Sawtell N. M. & Thompson R. L. (1992) Herpes simplex virus type 1 latency-associated transcription unit promotes anatomical site-dependant establishment and reactivation from latency. J. Virol. 66: 2157–2169). Two latency active promoters that drive expression of the LATs have been identified (Marconi P., Krisky D., Oligino T., Poliani P. L., Ramakrishnan R., Goins W. F., Fink D. A., Glorioso J. C. (1996) Replication-defective herpes simplex virus vectors for gene transfer in vivo. Proc. Natl. Acad. Sci. USA 93: 11319–11320) and may prove useful for vector transgene expression.

Two basic approaches have been used for production of HSV-1 vectors, namely amplicons and recombinant HSV-1 viruses. Amplicons are bacterially produced plasmids containing col E1 ori (an *Escherichia coli* origin of replication), OriS (the HSV-1 origin of replication), HSV-1 packaging sequence, the transgene under control of an immediate-early promoter and a selectable marker (Federoff H. J., Geschwind M. D., Geller A. I., Kessler J. A. (1992) Expression of nerve factor in vivo from a defective herpes simplex virus 1 vector prevents effects of axotomy on sympathetic ganglia. Proc. Natl. Acad. Sci. USA 89: 1636–1640). The amplicon is transfected into a cell line containing a helper virus (a temperature sensitive mutant), which provides all the missing structural and regulatory genes in trans. Both the helper- and amplicon-containing viral particles are delivered to the recipient. More recent amplicons include an Epstein-Barr virus-derived sequence for plasmid episomal maintenance (Wang S. & Vos J. (1996) A hybrid herpesvirus infectious vector based on Epstein-Barr virus and herpes simplex virus type 1 for gene transfer into human cells in vitro and in vivo. J. Virol. 70: 8422–8430).

Recombinant viruses are made replication-deficient by deletion of one of the immediate-early genes (e.g., ICP4), which is provided in trans. Though they are less pathogenic and can direct transgene expression in brain tissue, they are toxic to neurons in culture (Marconi P., Krisky D., Oligino T., Poliani P. L., Ramakrishnan R., Goins W. F., Fink D. A., Glorioso J. C. (1996) Replication-defective herpes simplex virus vectors for gene transfer in vivo. Proc. Natl. Acad. Sci. USA 93: 11319–11320). Deletion of a number of immediate-early genes substantially reduces cytotoxicity and also allows expression from promoters that would be silenced in the wild-type latent virus. These promoters may be of use in directing long term gene expression.

Replication-conditional mutants are only able to replicate in certain cell lines. Permissive cell lines are all proliferating and supply a cellular enzyme to complement for a viral deficiency. Mutants include thymidine kinase (During M. J., Naegele J. R., O'Malley K. L., Geller A. I. (1994) Long-term behavioral recovery in Parkinsonian rats by an HSV vector expressing tyrosine hydroxylase. Science 266: 1399–1403), ribonuclease reductase (Kramm C. M., Chase M., Herrlinger U., Jacobs A., Pechan P. A., Rainov N. G., Sena-esteves M., Aghi M., Barnett F. H., Chiocca E. A., Breakefield X. O. (1997) Therapeutic efficiency and safety of a second-generation replication-conditional HSV1 vector for brain tumor gene therapy. Human Gene Therapy 8: 2057–2068), UTPase, or the neurovirulence factor g34.5 (Kesari S., Randazzo B. P., Valyi-Nagy T., Huang Q. S., Brown S. M., MacLean A. R., Lee V. M., Trojanowski J. Q., Fraser N. W. (1995) Therapy of experimental human brain tumors using a neuroattenuated herpes simplex virus mutant. Lab. Invest. 73: 636–648). These mutants are particularly useful for the treatment of cancers, killing neoplastic cells, which proliferate faster than other cell types (Andreansky S. S., He B., Gillespie G. Y., Soroceanu L., Market J., Chou J., Roizman B., Whitley R. J. (1996) The application of genetically engineered herpes simplex viruses to the treatment of experimental brain tumors. Proc. Natl. Acad. Sci. USA 93: 11313–11318; Andreansky S. S., Sorcoceanu L., Flotte E. R., Chou J., Markert J. M., Gillespie G. Y., Roizman B., Whitley R. J. (1997) Evaluation of genetically engineered herpes simplex virus as oncolytic agents for human malignant brain tumors. Cancer Res. 57: 1502–1509).

A number of neurological diseases could be amenable to gene therapy by HSV-1 vectors (Kennedy P. G. E. (1997) Potential uses of herpes simplex virus (HSV) vectors for gene therapy of neurological disorders. Brain 120: 1245–1259). Though most attention has focused on cancers, there has been some success in Parkinson's disease by expressing tyrosine hydroxylase in striatal cells (Geller A. I., During M. J., Oh J. Y., Freese F., O'Malley K. (1995) An HSV-1 vector expressing tyrosine hydroxylase causes production and release of L-DOPA from cultured rat striatal cells. J. Neurochem. 64: 487–496; During M. J., Naegele J. R., O'Malley K. L., Geller A. I. (1994) Long-term behavioral recovery in Parkinsonian rats by an HSV vector expressing tyrosine hydroxylase. Science 266: 1399–1403), thus replacing the supply of L-dopa. Federoff et al. (Federoff H. J., Geschwind M. D., Geller A. I., Kessler J. A. (1992) Expression of nerve factor in vivo from a defective herpes simplex virus 1 vector prevents effects of axotomy on sympathetic ganglia. Proc. Natl. Acad. Sci. USA 89: 1636–1640) induced nerve repair following axotomy of the superior cervical ganglion, by injection of a vector expressing nerve growth factor. This resulted in restored levels of tyrosine hydroxylase.

However, Wood et al. (Wood M. J. A., Byrnes A. P., Pfaff D. W., Rabkin S. D., Charlton H. M. (1994) Inflammatory effects of gene-transfer into the CNS with defective HSV-1 vectors. Gene Therapy 1: 283–291) observed strong inflammatory responses to HSV-1 amplicon vectors, both at the primary site of the injection and at secondary sites supplied by nerve fibers originating from area of the injection. In addition up to 20% of experimental animals may die shortly after injection with HSV-1 vector (Kucharczuk J. C., Randazzo B., Chang M. Y., Amin K. M., Elshami A. A., Sterman D. H., Rizk N. P., Molnar-Kimber K. L., Brown S. M., MacLean A. R., Litzky L. A., Fraser N. W., Albelda S. M., Kaiser L. R. (1997) Use of a replication-restricted herpes virus to treat experimental human malignant mesothelioma. Cancer Research 57: 466–471), though the reason is unknown. A viral protein, ICP47, has been identified, which reduces viral antigen presentation and may be employed in future HSV-1 vectors to reduce cytotoxicity (York I. A., Roop C., Andrews D. W., Riddell R., Graham F. L., Johnson D. C. (1994) A cytosolic herpes simplex virus protein inhibits antigen presentation to CD8+ T lymphocytes. Cell 77: 525–535).

Because of its tropism for neuronal tissue issues of cellular targeting have been largely overlooked. However, wild type HSV-1 can infect and lyse other non-neuronal cell types, such as skin cells (Al-Saadi S. A., Clements G. B., Subak-Sharpe J. H. (1983) Viral genes modify herpes simplex virus latency both in mouse footpad and sensory ganglia. J. Gen. Virol. 64: 1175–1179), and it would be advantageous to target a specific subset of neurons. As HSV-1 will travel down the length of nerve efficient cellular targeting would improve its safety profile when used as a vector. Indeed a replication-restricted HSV-1 vector has been used to treat human malignant mesothelioma (Kucharczuk J. C., Randazzo B., Chang M. Y., Amin K. M., Elshami A. A., Sterman D. H., Rizk N. P., Molnar-Kimber K. L., Brown S. M., MacLean A. R., Litzky L. A., Fraser N. W., Albelda S. M., Kaiser L. R. (1997) Use of a replication-restricted herpes virus to treat experimental human malignant mesothelioma. Cancer Res. 57: 466–471).

Pox Virus Vectors

Pox virus vectors can also be used (e.g., Yaba-like disease virus: an alternative replicating poxvirus vector for cancer gene therapy. Hu Y, Lee J, McCart J A, Xu H, Moss B, Alexander H R, Bartlett D L J Virol 2001 75:10300–8).

Non-viral Vectors

Viral vectors all induce some degree of immunological response and may have other safety risks, such as insertional mutagenesis and direct toxicity. Furthermore, large-scale production may be difficult to achieve. Therefore, in some embodiments of the invention, non-viral methods of gene transfer are used, which may require only a small number of proteins, have a virtually infinite capacity, have no infectious or mutagenic capability, and large-scale production is possible using pharmaceutical techniques. There are at least three methods of non-viral DNA transfer, including naked DNA, liposomes and molecular conjugates.

Naked DNA (in the form of a plasmid) can be directly injected into muscle cells (Wolff J. A., Malone R. W., Williams P., Chong W., Acsadi G., Jani A., Felgner P. L. (1990) Direct gene transfer into mouse muscle in vivo. Science 247: 1465–1468) or attached to gold particles that are bombarded into the tissue (Cheng L., Ziegelhoffer P. R., Yang N. S. (1993) In vivo promoter activity and transgene expression in mammalian somatic tissues evaluated by using particle bombardment. Proc. Natl. Acad. Sci. USA 90: 4455–4459). Though not very efficient, this can result in prolonged, low-level expression in vivo. The simplicity of this method and sustained expression has led to the development of DNA vaccines. Compared to conventional attenuated and protein-based vaccines, they are unaffected by pre-existing immunity, such as that due to maternal antibodies, relatively cheap, and can deliver several pathogen antigens on a single plasmid (Manickan E., Karem K. L., Rouse B. T. (1997) DNA vaccines—a modern gimmick or a boon to vaccinology. Critical Reviews in Immunology 17: 139–154). DNA vaccines are being developed for those pathogens where there is no existing vaccine, such as HIV (Lekutis C., Shiver J. W., Liu M. A., Letvin L. N. (1997) HIV1 env DNA vaccine administered to rhesus monkeys elicits MHC class II-restricted CD4+ T helper cells that secrete IFN-gamma and TNF-alpha. J. Immunol. 158: 4471–4477), or where the current vaccine is not fully effective, such as influenza (Macklin M. D., McCabe D., McGregor M. W., Neumann V., Meyer T., Callan R., Hinshaw V. S., Swain W. S. (1998) Immunization of pigs with a particle mediated vaccine to influenza A virus protects against challenge with homologous virus. J. Virol. 72: 1491–1496). By using a highly conserved gene Ulmer et al. (Ulmer J. B., Donnelly J. J., Parker S. E., Rhodes G. H., Felgner P. L., Dwarki J. J., Gromkowski S. H., Deck R., DeWitt C. M., Friedman A., Hawe L. A., Laender K. R., Martinz D., Perry H. C., Shiver J., Montgomery D. L., Liu M. A. (1993) Heterologous protection against influenza by injection of DNA encoding a viral protein. Science 254: 1745–1749) were able to immunize mice against two serologically distinct influenza virus strains. In most cases, however, DNA vaccines have not been shown to be better than the existing vaccines (Macklin M. D., McCabe D., McGregor M. W., Neumann V., Meyer T., Callan R., Hinshaw V. S., Swain W. S. (1998) Immunization of pigs with a particle-mediated vaccine to influenza A virus protects against challenge with homologous virus. J. Virol. 72: 1491–1496). The actual type of immune response can be controlled by cotransformation of a gene encoding an appropriate cytokine (Xiang Z. & Ertl H. C. (1995) Manipulation of the immune response to a plasmid-encoded viral antigen by co-inoculation with plasmids expressing cytokines. Immunity 2: 129–135) and this method may prove useful in redirecting inappropriate immune responses (Manickan E., Karem K. L., Rouse B. T. (1997) DNA vaccines—a modern gimmick or a boon to vaccinology. Critical Reviews in Immunology 17: 139–154). Other uses for naked DNA include cancer immunopotentiation (discussed below; see also Corr M., Tighe H., Lee D., Dudler J., Trieu M., Brinson D. C., Carson D. A. (1997) Costimulation provided by DNA immunization enhances antitumor immunity. J. Lab. Invest. 159: 4999–5004), repair of pancreatic insulin function (Goldfine I. D., German M. S., Tseng H., Wang J., Bolaffi J. L., Chen J., Olson D. C., Rothman S. S. (1997). The endocrine secretion of human insulin and growth hormone by exocrine glands of the gastrointestinal tract. Nature Biotech. 15: 1378–1382), and stimulation of collateral blood vessel development (Takeshita S., Tsurumi Y., Couffinahl T., Asahara T., Bauters C., Symes J., Ferrara N., Isner J. M. (1996) Gene transfer of naked DNA encoding for three isoforms of vascular endothelial growth factor endothelial growth factor stimulates collateral development in vivo. Lab. Invest. 75: 487–501). Expression of the gene product in muscle tissue can be improved by the coadministration of collagenase, papaverine and ischemic conditions (Budker V., Zhang G., Danko I., Williams P., Wolff J. (1998) The efficient expression of intravascularly delivered DNA in rat muscle. Gene Therapy 5: 272–276). The use of a muscle specific promoter (Skarli M., Kiri A., Vrbova G., Lee C. A., Goldspink G. (1998) Myosin regulatory elements as vectors for gene transfer by intramuscular injection. Gene Therapy 5: 514–520) and other intragene regulatory sequences, such as the poly A and transcription termination sequence (Hartikka J., Sawdey M., Conefert-Jensen F., Margalith M., Barnhardt K., Nolasco M., Vahlsing H. L., Meek J., Marquet M., Hobart P., Norman J., Manthorpe M. (1996) An improved plasmid DNA expression vector for direct injection into skeletal muscle. Human Gene Therapy 7: 1205–1217) will also improve transgene expression.

Liposomes are lipid bilayers entrapping a fraction of aqueous fluid. DNA will spontaneously associate to the external surface of cationic liposomes by virtue of its charge, and these liposomes will interact with the cell membrane (Feigner J. H., Kumar R., Sridhar C. N., Wheeler C. J., Tasi Y. J., Border R., Ramsey P., Martin M., Feigner P. L. (1994) Enhanced gene delivery system and mechanism studies with a novel series of cationic lipid formulations. J. Biol. Chem. 269: 2550–2561). In vitro up to 90% of certain cell lines may be transfected. By including a small amount of an anionic lipid in an otherwise cationic liposome, the DNA can be incorporated into the internal surface of the liposome, protecting it from enzymatic degradation (Alio S. F. (1997) Long term expression of the human alpha-1-antitrypsin gene in mice employing anionic and cationic liposome vector. Biochem. Pharmacol. 54: 9–13). To facilitate uptake into the cell as endosomes, targeting proteins have been included in liposomes, such as an anti-MHC antibody (Wang C. & Huang L. (1987) pH-sensitive immunoliposomes mediate target-cell-specific delivery and controlled expression of a foreign gene in mouse. Proc. Natl. Acad. Sci. USA 84: 7851–7855), transferrin (Stavridis J. C., Deliconstantinos G., Psallidopoulos M. C., Armenakas N. S., Hadjiminas D. J., Hadjiminas J. (1986) Construction of transferrin-coated liposomes for in vivo transport of exogenous DNA to bone marrow erythroblasts in rabbits. Experimental Cell Research 164: 568–572), and the Sendai virus or its F protein (Dzau J. V., Mann M. J, Morishita R., Kaneda Y. (1996). Fusigenic viral liposome for gene therapy in cardiovascular disease. Proc. Natl. Acad. Sci. USA 93: 11421–11425). The Sendai virus additionally allows the plasmid DNA to escape from the endosome into the cytoplasm, thus avoiding degradation. The inclusion of a DNA-binding protein (e.g., 28 kDa high mobility group 1 protein) enhances transcription by bringing the plasmid into the nucleus (Dzau J. V., Mann M. J, Morishita R., Kaneda Y. (1996). Fusigenic viral liposome for gene therapy in cardiovascular disease. Proc. Natl. Acad. Sci. USA 93: 11421–11425). Further proposed improvements include incorporating the Epstein-Barr virus Ori p and EBNA1 genes in the plasmid (as described above for HSV-1 amplicons) to maintain the plasmid as an episomal element (Alio S. F. (1997) Long term expression of the human alpha-1-antitrypsin gene in mice employing anionic and cationic liposome vector. Biochem. Pharmacol. 54: 9–13).

Molecular conjugates consist of protein or synthetic ligands to which a DNA binding agent has been attached. Delivery to the cell can be improved by using similar techniques to those for liposomes. Targeting proteins include asialoglycoprotein (Wagner E., Cotten M., Foisner R., Birnstiel M. L. (1991) Transferrin-polycation-DNA complexes: the effect of polycations on the structure of the complex and DNA delivery to cells. Proc. Natl. Acad. Sci. USA 88: 4255–4259), transferrin (Wu C. H., Wilson J. M., Wu. G. Y. (1989) Targeting genes: delivery and persistent expression of a foreign gene driven by mammalian regulatory elements in vivo. J. Biol. Chem. 264: 16985–16987), polymeric IgA (Ferkol T., Kaetzel C. S., Davis P. B. (1993) Gene transfer into respiratory epithelial cells by targeting the polymeric immunoglobulin receptor. J. Clin. Invest. 92: 2394–2400) and adenovirus (Madon J. & Blum H. E. (1996) Receptor mediated delivery of hepatitis B virus DNA and antisense oligodeoxynucleotides to avian liver cells. Hepatology 24: 474–481). Transgene expression tends to be transient and is limited by endosome/lysosomal degradation.

X Assays and Kits

In one embodiment of the present invention, the transfected cells can be used to create two assay systems to assess the ability of EBV-TK to sensitize cells to candidate active compounds. Cells that express KHSV-TK can be prepared similarly for assay purposes.

The present invention is described by way of illustration, in the following examples. It will be understood by one of ordinary skill in the art that these examples are in no way limiting and that variations of detail can be made without departing from the spirit and scope of the present invention.

EXAMPLES

Nucleoside Syntheses

All reagents were used as received unless stated otherwise. Anhydrous solvents were purchased from Aldrich Chemical Company, Inc. (Milwaukee). Melting points (mp) were determined on an Electrothermal digit melting point apparatus and are uncorrected. $^1$H and $^{13}$C NMR spectra were obtained using a Varian Unity Plus 400 spectrometer at room temperature and reported in ppm downfield from internal tetramethylsilane. Deuterium exchange, decoupling experiments or 2D-COSY were performed to confirm proton assignments. Signal multiplicities are represented by s (singlet), d (doublet), dd (doublet of doublets), t (triplet), q (quadruplet), br (broad), bs (broad singlet), m (multiplet). All J-values are in Hz. Mass spectra were recorded using a JEOL JMS-SX/SX102A/E mass spectrometer. Elemental analyses were performed by Atlantic Microlab Inc. (Norcross, Ga.). Analytic TLC was performed on Whatman LK6F silica gel plates, and preparative TLC on Whatman PK5F silica gel plates. Column chromatography was carried out on Silica Gel (Fisher, S733-1) at atmospheric pressure.

Example 1

β-D-5-E-(2-Carbomethoxyvinyl)-2'-deoxyuridine (2)

To a solution of Pd(OAc)$_2$ (96 mg, 0.42 mmol) and Ph$_3$P (240 mg, 0.92 mmol) in 1,4-dioxane (90 mL) was added 2'-deoxy-5-iodouridine (1, 2.68 g, 7.56 mmol), followed by methyl acrylate (1.6 mL, 19.78 mmol). The mixture was heated at reflux under nitrogen atmosphere for 16 h. The hot mixture was filtered through a pad of celite, and the celite was rinsed with hot 1,4-dioxane. The combined filtrate was concentrated in vacuo, and the residue was purified by flash chromatography on silica gel eluting with CH$_2$Cl$_2$/MeOH (85:15 to 75:25) to give the title compound 2 as a pale yellow solid (2.17 g, 92%). $^1$H NMR (DMSO-d$_6$) δ 8.42 (s, 1H, H-6), 7.37, 6.85 (2d, J =16 Hz, 2H, CH=CH), 6.12 (t, J=6.4 Hz, 1H, H-1'), 5.28 (d, J=4.4 Hz, 1H, OH), 5.19 (t, J=5.2 Hz, 1H, OH), 4.25 (m, 1H, H-3'), 3.81–3.78 (m, 1H, H-4'), 3.68 (s, 3H, CH$_3$), 3.66–3.56 (m, 2H, H-5'), 2.19–2.15 (m, 2H, H-2').

In an analogous manner to the preparation of compound 2, β-L-5-E-(2-carbomethoxy-vinyl)-2'-deoxyuridine 7 was prepared from β-L-2'-deoxy-5-iodouridine (6; prepared according to Holy A. (1972) Nucleic acid components and their analogues. CLIII. Preparation of 2'-deoxy-L-ribonucleosides of the pyrimidine series, *Coll. Czech. Chem. Commun.* 37, 4072–4086; Lin T.-S., Luo M.-Z., Liu M.-C. (1995) Synthesis of several pyrimidine L-nucleoside analogues as potential antiviral agents, *Tetrahedron,* 51, 1055–1068). $^1$H NMR (DMSO-d$_6$) δ 8.42 (s, 1H, H-6), 7.37, 6.85 (2d, 2H, J=16 Hz, CH=CH), 6.12 (t, J=6.4 Hz, 1H, H-1'), 5.25 (d, J=4.4 Hz, 1H, OH), 5.20 (t, J=5.2 Hz, 1H, OH), 4.25 (m, 1H, H-3'), 3.78–3.81 (m, 1H, H-4'), 3.68 (s, 3H, CH3), 3.66–3.56 (m, 2H, H-5'), 2.19–2.15 (m, 2H, H-2').

In an analogous manner to the preparation of compound 2, 1-(β-L-arabinofuranosyl)-5-E-(2-carbomethoxyvinyl) uracil 11 was prepared from 1-(β-L-arabinofuranosyl)-5-iodouracil (10; prepared according to Holy A. (1972) Nucleic acid components and their analogues. CLIII. Preparation of 2'-deoxy-L-ribonucleosides of the pyrimidine series, *Coll. Czech. Chem. Commun.* 37, 4072–4086; T.-S. Lin, M.-Z. Luo, M.-C. Liu, (1995) Synthesis of several pyrimidine L-nucleoside analogues as potential antiviral agents, *Tetrahedron,* 51, 1055–1068). $^1$H NMR (DMSO-d$_6$) δ 11.5 (s, 1H, NH), 8.22 (s, 1H, H-6), 7.39, 6.85 (2d, J=16 Hz, 2H, CH=CH), 6.01 (d, 1H, H-1'), 5.58 (d, 1H, OH), 5.47 (d, 1H, OH), 5.23 (t, 1H, OH), 4.15–3.90 (m, 2H, H-2', H-3'), 3.60–3.70 (m, 3H, H-4', H-5'), 3.35 (s, 3H, CH$_3$).

In an analogous manner to the preparation of compound 2, 1-(β-D-arabinofuranosyl)-5-E-(2-carbomethoxyvinyl) uracil 17 was prepared from 16. $^1$NMR (DMSO-d$_6$) δ 11.5 (s, 1H, NH), 8.22 (s, 1H, H-6), 7.39, 6.85 (2d, 2H, J=16 Hz, CH=CH), 6.01 (d, 1H, H-1'), 5.60 (d, 1H, OH), 5.48 (d, 1H, OH), 5.24 (t, 1H, OH), 4.15–3.90 (m, 2H, H-2', H-3'), 3.60–3.70 (m, 3H, H-4', H-5'), 3.35 (s, 3H, CH$_3$).

In an analogous manner to the preparation of compound 2, 5-E-(2-carbomethoxyvinyl)-1-[(1,3-dihydroxy-2-propoxy)methyl]uracil 52 was prepared from 46. $^1$H NMR (DMSO-d$_6$) δ 11.5 (s, 1H, NH), 8.40 (s, 1H, H-6), 7.38, 6.85 (2d, 2H, J=16 Hz, CH=CH), 7.10, 6.50 (2br, 2H, 2 OH), 5.15 (s, 2H, CH$_2$N), 4.60 (m, 2H, CH$_2$O), 3.69 (s, 3H, CH$_3$), 3.52 (m, 1H, CHO), 3.41 (m, 2H, 2 CH$_2$O).

In an analogous manner to the preparation of compound 2, (±)-(1'β,3'α,4'β)-5-E-(2-carbomethoxyvinyl)-1-[3-hydroxy-4-(hydroxymethyl)cyclopentyl]uracil 73 was prepared from (±)-(1'β,3'α,4'β)-1-[3-hydroxy-4-(hydroxymethyl)cyclopentyl]-5-iodouracil (72). $^1$H NMR (DMSO-d$_6$) δ 8.40 (s, 1H, H-6), 7.37, 6.85 (2d, 2H, J=16 Hz, CH=CH), 5.0–4.5 (m, 3H, CHN, 2 OH), 4.00 (m, 1H, CHOH), 3.70 (s, 3H, CH$_3$), 3.42 (m, 2H, CH$_2$OH), 2.25–1.05 (m, 5H).

Compound 72 was prepared according to published procedures from (±)-(1β,2α,3α,4β)-4-amino-2,3-dihydroxy-1-cyclopentanemethanol (71): Shealy Y. F., O'Dell C. A. (1976) *J. Heterocycl. Chem.* 13, 1015; Herdewijn P., De Clercq E., Balzarini J., Vanderhaeghe H. (1985) Synthesis and antiviral activity of the carbocyclic analogues (E)-5-(2-halovinyl)-2'-deoxyuridines and (E)-5-(2-halovinyl)-2'-deoxycytidines, *J. Med. Chem.* 28, 550–555.

Compound 71 was prepared according to Kam B. L. & Oppenheimer N. J. (1981) Carbocyclic sugar amines: synthesis and stereochemistry of racemic α- and β-carbocyclic ribofuranosylamine, carbocyclic lyxofuranosylamine, and related compounds, *J. Org. Chem.* 46, 3268–3272.

In an analogous manner to the preparation of compound 2, (2R,4R)-1-[2-(hydroxymethyl)-1,3-dioxolan-4-yl]-5-E-(2-carbomethoxy-vinyl)uracil 100 was prepared from 99. $^1$NMR (DMSO-d$_6$) δ 11.5 (s, 1H, NH), 7.61 (s, 1H, H-6), 7.36, 6.85 (2d, 2H, CH=CH), 6.25 (m, 1H, H-2'), 5.22 (t, 1H, OH), 5.10 (m, 1H, H-4'), 4.25–4.05 (m, 4H, H-5', H-6'), 3.67 (s, 3H, CH$_3$).

In an analogous manner to the preparation of compound 2, (2S,4S)-1-[2-(hydroxymethyl)-1,3-dioxolan-4-yl]-5-E-(2-carbomethoxy-vinyl)uracil 108 was prepared from 107. $^1$H NMR (DMSO-d$_6$) δ 11.5 (s, 1H, NH), 7.61 (s, 1H, H-6), 7.36, 6.85 (2d, 2H, CH=CH), 6.25 (m, 1H, H-2'), 5.21 (t, 1H, OH), 5.10 (m, 1H, H-4'), 4.25–4.05 (m, 4H, H-5', H-6'), 3.67 (s, 3H, CH$_3$).

Example 2

β-D-2'-Deoxy-5-E-(2-chlorovinyl)uridine (4)

A solution of 2 (1.25 g, 4.0 mmol) in aqueous NaOH (1 N, 50 mL) was stirred at room temperature overnight. The solution was cooled to 0° C. and brought to pH 2 by the addition of 4 N HCl. The mixture was stand in ice for 30 minutes, and the white precipitate was filtered. The filtrate was evaporated to dryness in vacuo and water was added. The resulting precipitate was filtered and washed with water. The combined precipitate was dissolved in water (40 mL) by heating with KOAc (1.96 g, 20 mmol), and N-chlorosuccinimide (536 mg, 4.0 mmol) was added portion-wise. The solution was heated at reflux for 3 h, and then concentrated in vacuo. The residue was purified by flash chromatography on silica gel eluting with $CH_2Cl_2$/MeOH (9:1) to give the title compound 3 as a -white solid (438 mg, 38%). $^1$H NMR (DMSO-$d_6$) δ 11.6 (s, 1H, NH), 8.06 (s, 1H, H-6), 7.18, 6.59 (2d, 2H, J=13.2 Hz, CH=CH), 6.13 (t, J=6.4 Hz, 1H, H-1'), 5.28 (d, J=4.0 Hz, 1H, OH-3'), 5.12 (t, J=5.2 Hz, 1H, OH-5'), 4.24 (m, 1H, H-3'), 3.78 (m, 1H, H-4'), 3.63–3.57 (m, 2H, H-5'), 2.13 (m, 2H, H-2').

In an analogous manner to the preparation of compound 4, β-L-5-E-(2-chlorovinyl)-2'-deoxyuridine 9 was prepared from 7. $^1$H NMR (DMSO-$d_6$) δ 11.6 (s, 1H, NH), 8.05 (s, 1H, H-6), 7.17, 6.58 (2d, 2H, J=13.2 Hz, CH=CH), 6.13 (t, J=6.8 Hz, 1H, H-1'), 5.27 (d, J=4.4 Hz, 1H, OH-3'), 5.11 (t, J=5.2 Hz, 1H, OH-5'), 4.24 (m, 1H, H-3'), 3.78 (m, 1H, H-4'), 3.66–3.56 (m, 2H, H-5'), 2.13 (m, 2H, H-2').

In an analogous manner to the preparation of compound 4, 1-(β-L-arabinofuranosyl)-5-E-(2-chlorovinyl)uracil 13 was prepared from 11. $^1$NMR (DMSO-$d_6$) δ 11.4 (s, 1H, NH), 7.87 (s, 1H, H-6), 7.15, 6.58 (2d, J=13 Hz, 2H, CH=CH), 6.01 (d, 1H, H-1'), 5.56 (d, 1H, OH), 5.45 (d, 1H, OH), 5.05 (t, 1H, OH), 4.05 (m, 1H, H-2'), 3.90 (m, 1H, H-3'), 3.75 (m, 1H, H-4'), 3.61 (m, 2H, H-5').

In an analogous manner to the preparation of compound 4, 1-(β-D-arabinofuranosyl)-5-E-(2-chlorovinyl)uracil 19 was prepared from 17. $^1$H NMR (DMSO-$d_6$) δ 11.45 (s, 1H, NH), 7.87 (s, 1H, H-6), 7.15, 6.58 (2d, J=13 Hz, 2H, CH=CH), 6.01 (d, 1H, H-1'), 5.57 (d, 1H, OH), 5.44 (d, 1H, OH), 5.05 (t, 1H, OH), 4.05 (m, 1H, H-2'), 3.90 (m, 1H, H-3'), 3.75 (m, 1H, H-4'), 3.61 (m, 2H, H-5').

In an analogous manner to the preparation of compound 4, 5-E-(2-chlorovinyl)-1-[(1,3-dihydroxy-2-propoxy)methyl]uracil 53 was prepared from 52. $^1$H NMR (DMSO-$d_6$) δ 11.4 (s, 1H, NH), 8.03 (s, 1H, H-6), 7.28, 6.85 (2d, 2H, J=13 Hz, CH=CH), 7.10, 6.55 (2br, 2H, 2 OH), 5.18 (s, 2H, $CH_2N$), 4.60 (m, 2H, CH2O), 3.50 (m, 1H, CHO), 3.41 (m, 2H, 2 $CH_2O$).

In an analogous manner to the preparation of compound 4, (±)-(1'β,3'α,4'β)-5-E-(2-chlorovinyl)-1-[3-hydroxy-4-(hydroxymethyl)cyclopentyl]uracil 74 was prepared from 73. $^1$H NMR (DMSO-$d_6$) δ 11.4 (s, 1H, NH), 7.96 (s, 1H, H-6), 7.24, 6.75 (2d, J=13 Hz, 2H, CH=CH), 5.0–4.6 (m, 3H, CHN, 2 OH), 4.01 (m, 1H, CHOH), 3.43 (m, 2H, $CH_2OH$), 2.25–1.35 (m, 5H).

Example 3

1-(β-D-Arabinofuranosyl)uracil (15)

A mixture of uridine (14; 13.25 g, 54.5 mmol), diphenyl carbonate (15.48 g, 72.5 mmol), anhydrous $NaHCO_3$ (349 mg, 4.15 mmol), and hexamethylphosphoric triamide (50 mL) was heated with stirring at 150° C. under nitrogen for 20 min, and then cooled to room temperature. The mixture was poured into cold water (400 mL), and washed with $CHCl_3$. $Et_3N$ (25 mL) was added, and the aqueous solution was heated at 70° C. for 5 h. The solvent was evaporated in vacuo, and the residue was crystallized from MeOH/water to give the title compound 15 as a white solid (11.13 g, 84%). $^1$H NMR (DMSO-$d_6$) δ 11.2 (s, 1H, NH), 7.60 (d, J=7.5 Hz, 1H, H-6), 5.95 (d, 1H, H-1'), 5.51 (d, J=7.5 Hz, 1H, H-5), 6.30–5.30 (br, 2H, 2 OH), 4.10–3.50 (m, 6H, H-2', H-3', H-4', H-5', OH).

Example 4

1-(β-D-Arabinofuranosyl)-5-iodouracil (16)

A mixture of 15 (1.2 g, 4.9 mmol), iodine (1.50 g, 5.9 mmol), $CHCl_3$ (6 mL), and 1 N $HNO_3$ (24 mL) was heated at reflux for 2 hours, and then cooled. The crystalline solid was collected by filtration and washed with ether to give the title compound 16 as a white solid (1.12 g, 62%). $^1$H NMR (DMSO-$d_6$) δ 11.6 (s, 1H, NH), 8.10 (s, 1H, H-6), 5.95 (d, 1H, H-1'), 5.52 (br, 1H, OH), 5.40–5.10 (br, 1H, OH), 4.15–3.90 (m, 2H, H-2', H-3'), 3.80–3.60 (m, 3H, H-4', H-5'), 3.60–3.30 (m, 1H, OH).

Example 5

β-D-3',5'-Di-O-benzoyl-2'-deoxy-5-iodouridine (20)

To a solution of 1 (5.56 g, 20 mmol) in anhydrous pyridine (100 mL) at 0° C. was added benzoyl chloride (6.185 g, 44 mmol) dropwise. After addition, the reaction solution was allowed to warm to room temperature, then heated at 50° C. for 2 h, and evaporated in vacuo to dryness. The residue was treated with $CHCl_3$ (200 mL), and the organic phase was washed with 1 N $H_2SO_4$, water, dried, filtered, and concentrated in vacuo. Column chromatography of the residue ($CH_2Cl_2$/MeOH, 95:5) gave the title compound 20 as a white solid (10.35 g, 92%). $^1$H NMR ($CDCl_3$) δ 8.08–7.43 (m, 11H, arom., H-6), 6.39–6.36 (m, 1H, H-1'), 5.64 (d, J=6.8 Hz, 1H, H-3'), 4.77 (d, J=3.2 Hz, 2H, H-5'), 4.59 (m, 1H, H-4'), 2.83–2.78, 2.38–2.31 (2m, 2H, H-2').

In an analogous manner to the preparation of compound 20, β-L-3',5'-di-O-benzoyl-2'-deoxy-5-iodouridine 23 was prepared from 6. $^1$H NMR ($CDCl_3$) δ 8.08–7.42 (m, 11H, arom., H-6), 6.39–6.37 (m, 1H, H-1'), 5.64 (d, J=6.8 Hz, 1H, H-3'), 4.77 (d, J=3 Hz, 2H, H-5'), 4.59 (m, 1H, H-4'), 2.83–2.78, 2.38–2.30 (2m, 2H, H-2').

In an analogous manner to the preparation of compound 20, 5-iodo-1-(2,3,5-tri-O-benzoyl-β-L-arabinofuranosyl)uracil 26 was prepared from 10. $^1$H NMR (DMSO-$d_6$) δ 11.6 (s, 1H, NH), 8.10–7.40 (m, 16H, arom., H-6), 6.20 (d, 1H, H-1'), 5.65 (d, 1H, H-2'), 5.35 (d, 1H, H-3'), 5.24 (m, 1H, H-4'), 4.40–4.20 (m, 2H, H-5').

In an analogous manner to the preparation of compound 20, 5-iodo-1-(2,3,5-tri-O-benzoyl-β-D-arabinofuranosyl)uracil 29 was prepared from 16. $^1$H NMR (DMSO-$d_6$) δ 11.5 (s, 1H, NH), 8.10–7.40 (m, 16H, arom., H-6), 6.20 (d, 1H, H-1'), 5.66 (d, 1H, H-2'), 5.35 (d, 1H, H-3'), 5.25 (m, 1H, H-4'), 4.40–4.20 (m, 2H, H-5').

In an analogous manner to the preparation of compound 20, β-D-2',3',5'-tri-O-benzoyl-5-iodouridine 33 was prepared from 32. $^1$NMR ($CDCl_3$) δ 8.32 (br, 1H, NH), 8.16–7.36 (m, 16H, arom., H-6), 6.37 (d, 1H, H-1'), 5.90 (m, 1H, H-2'), 5.75 (t, 1H, H-3'), 4.86–4.83 (m, 1H, H-4'), 4.76–4.70 (m, 2H, H-5').

Example 6

β-D-3',5'-Di-O-benzoyl-2'-deoxy-5-vinyluridine (21)

To a solution of 20 (562 mg, 1 mmol) in 1-methyl-pyrrolidinone (NMP, 3 mL) were added tri(2-furyl)phosphine (9 mg), tris(dibenzylidene acetonyl)bispalladium (9 mg), and tributylvinyltin (350 mg, 1.1 mmol) sequentially. After being stirred at room temperature under nitrogen atmosphere for 3 days, the mixture was diluted with EtOAc (50 mL), washed with water, dried and concentrated. The residue was purified by flash chromatography on silica gel eluting with hexane/EtOAc (6:4) to give the title compound 21 as a brownish-yellow foam (450 mg, 97%). $^1$H NMR (DMSO-$d_6$) δ 8.32–7.50 (m, 11H, arom., H-6), 6.32–6.24 (m, 2H, CH=$CH_2$, H-1'), 5.92, 5.13 (2dd, 2H, CH=$CH_2$), 5.69–5.65 (m, 1H, H-3'), 4.69–4.59 (m, 3H, H-4', H-5'), 2.84–2.65 (2m, 2H, H-2').

In an analogous manner to the preparation of compound 21, β-L-3',5'-di-O-benzyol-2'-deoxy-5-vinyluridine 24 was prepared from 23. $^1$NMR (DMSO-$d_6$) δ 8.31–7.50 (m, 11H, arom., H-6), 6.32–6.24 (m, 2H, CH=$CH_2$, H-1'), 5.92, 5.13 (2dd, 2H, CH=$CH_2$), 5.69–5.65 (m, 1H, H-3'), 4.69–4.59 (m, 3H, H-4', H-5'), 2.84–2.66 (2m, 2H, H-2').

In an analogous manner to the preparation of compound 21, 1-(2,3,5-tri-O-benzoyl-β-L-arabinofuranosyl)-5-vinyluracil 27 was prepared from 26. $^1$H NMR (DMSO-$d_6$) δ 11.5 (s, 1H, NH), 8.11–7.40 (m, 16H, arom., H-6), 6.32–6.23 (m, 2H, CH=$CH_2$, H-1'), 5.92, 5.13 (2dd, 2H, CH=$CH_2$), 5.65 (d, 1H, H-2'), 5.35 (d, 1H, H-3'), 5.24 (m, 1H, H-4'), 4.40–4.230 (m, 2H, H-5').

In an analogous manner to the preparation of compound 21, 1-(2,3,5-tri-O-benzoyl-β-D-arabinofuranosyl)-5-vinyluracil 30 was prepared from 29. $^1$NMR (DMSO-$d_6$) δ 11.55 (s, 1H, NH), 8.12–7.40 (m, 16H, arom., H-6), 6.32–6.22 (m, 2H, CH=$CH_2$, H-1'), 5.92, 5.13 (2dd, 2H, CH=$CH_2$), 5.64 (d, 1H, H-2'), 5.35 (d, 1H, H-3'), 5.24 (m, 1H, H-4'), 4.40–4.230 (m, 2H, H-5').

In an analogous manner to the preparation of compound 21, β-D-2',3',5'-tri-O-benzoyl-5-vinyluridine 34 was prepared from 33. $^1$H NMR (CDCl$_3$) δ 8.36 (bs, 1H, NH), 8.15 (d, 1H, H-6), 8.13–7.36 (m, 15H, arom.), 6.45 (d, 1H, H-1'), 6.02–5.72 (m, 4H, CH=$CH_2$, H-4'), 5.00 (m, 1H, H-3'), 4.88 (m, 1H, H-4'), 4.75–4.67 (m, 2H, H-5').

In an analogous manner to the preparation of compound 21, 1-[[1,3-bis(acetoxy)-2-propoxy]methyl]-5-vinyluracil 48 was prepared from 47. $^1$H NMR (CDCl$_3$) δ 8.36 (br, 1H, NH), 7.37 (s, 1H, H-6), 6.40 (dd, 1H, CH=$CH_2$), 6.00, 5.31 (2d, 2H, CH=$CH_2$), 5.28 (s, 2H, $CH_2$N), 4.23, 4.08 (2m, 5H, 2 $CH_2$, CHO), 2.04 (s, 6H, 2 $CH_3$).

In an analogous manner to the preparation of compound 21, β-D-2'-deoxy-3',5'-di-O-p-toluoyl-4'-thio-5-vinyluridine 56 was prepared from 55. $^1$NMR (CDCl$_3$) δ 7.95–7.25 (m, 8H, arom., H-6), 6.69 (dd, 1H, H-1'), 6.31–6.25 (m, 2H, CH=$CH_2$, H-1'), 5.90, 5.11 (2dd, 2H, CH=$CH_2$), 5.76 (m, 1H, H-3'), 4.68 (m, 2H, H-5'), 4.05 (m, 1H, H-4'), 2.75, 2.41 (2m, 2H, H-2'), 2.42 (s, 6H, 2 $CH_3$).

In an analogous manner to the preparation of compound 21, 1-(4-thio-2,3,5-tri-O-benzyl-β-D-arabinofuranosyl)-5-vinyluracil 64 was prepared from 63. $^1$H NMR (CDCl$_3$) δ 8.10 (br, 1H, NH), 7.82 (s, 1H, H-6), 7.40–7.15 (m, 15H, arom.), 6.32–6.25 (m, 2H, CH=$CH_2$, H-1'), 5.90, 5.12 (2dd, 2H, CH=$CH_2$), 4.70–4.40 (m, 6H, 3 $CH_2$), 4.22 (m, 2H, H-2', H-3'), 3.65 (m, 2H, H-5'), 3.40 (m, 1H, H-4').

In an analogous manner to the preparation of compound 21, (±)-(1'β,3'α,4'β)-1-[3-acetoxy-4-(acetoxymethyl)cyclopentyl]-5-vinyluracil 76 was prepared from 75. $^1$H NMR (DMSO-$d_6$) δ 11.5 (bs, 1H, NH), 8.02 (s, 1H, H-6), 6.36 (dd, 1H, CH=$CH_2$), 5.91, 5.12 (2dd, 2H, CH=$CH_2$), 5.00 (m, 1H, CHO), 4.92 (m, 1H, CHN), 4.18, 4.05 (2m, 2H, $CH_2$O), 2.02 (s, 6H, 2 $CH_3$), 2.45–1.85 (2m, 4H, 2 $CH_2$), 1.57 (m, 1H, CH).

In an analogous manner to the preparation of compound 21 but replacing tributyl(vinyl)tin with 2-(tributylstannyl)furan, β-D-2'-deoxy-3',5'-di-O-benzoyl-5-furanyluridine 80 was prepared from 20. $^1$NMR (CDCl$_3$) δ 8.16 (s, 1H, H-6), 8.09–7.41 (m, 10H, arom.), 6.93 (d, J=2.8 Hz, 1H, furanyl), 6.82 (d, J=1.2 Hz, 1H, furanyl), 6.56 (m, 1H, furanyl), 6.31 (m, 1H, H-1'), 5.71 (d, J=6.4 Hz, 1H, H-3'), 4.78 (d, 2H, H-5'), 4.65 (m, 1H, H-4'), 2.85, 2.52 (2m, 2H, H-2').

In an analogous manner to the preparation of compound 21 but replacing tributyl(vinyl)tin with 2-(tributylstannyl)thiophene, β-D-2'-deoxy-3',5'-di-O-benzoyl-5-(thien-2-yl)uridine 81 was prepared from 20. $^1$NMR (CDCl$_3$) δ 8.06–7.19 (m, 13H, arom., H-6), 6.86 (t, 1H, J=4.4 Hz, thienyl), 6.49 (m, 1H, H-1'), 5.69 (d, 1H, J=6.4 Hz, H-3'), 4.86–4.77 (m, 2H, H-5'), 4.65–4.63 (m, 1H, H-4'), 2.86, 2.44 (2m, 2H, H-2').

In an analogous manner to the preparation of compound 21 but replacing tributyl(vinyl)tin with 2-(tributylstannyl)furan, β-L-2'-deoxy-3',5'-di-O-benzoyl-5-(2-furanyl)uridine 87 was prepared from 23. $^1$NMR (CDCl$_3$) δ 8.16 (s, 1H, H-6), 8.10–7.40 (m, 10H, arom.), 6.93 (d, J=2.8 Hz, 1H, furanyl), 6.82 (d, J=1.2 Hz, 1H, furanyl), 6.56 (m, 1H, furanyl), 6.31 (m, 1H, H-1'), 5.71 (d, J=6.4 Hz, 1H, H-3'), 4.78 (d, 2H, H-5'), 4.65 (m, 1H, H-4'), 2.85, 2.52 (2m, 2H, H-2').

In an analogous manner to the preparation of compound 21 but replacing tributyl(vinyl)tin with 2-(tributylstannyl)thiophene, β-L-2'-deoxy-3',5'-di-O-benzoyl-5-(thien-2-yl)uridine 88 was prepared from 23. $^1$NMR (CDCl$_3$) δ 8.06–7.19 (m, 13H, arom., H-6), 6.86 (t, 1H, J=4.4 Hz, thienyl), 6.49 (m, 1H, H-1'), 5.69 (d, 1H, J=6.4 Hz, H-3'), 4.86–4.77 (m, 2H, H-5'), 4.65–4.63 (m, 1H, H-4'), 2.86, 2.44 (2m, 2H, H-2').

In an analogous manner to the preparation of compound 21, (2R,4R)-1-[2-(benzyloxymethyl)-1,3-dioxolan-4-yl]-5-vinyluracil 95 was prepared from 94 (compound 94 was prepared according to J.-S. Lin, T. Kira, E. Gullen, Y. Choi, F. Qu, C. K. Chu, Y.-C. Cheng, J. Med. Chem. 1999, 42, 2212–2217). $^1$NMR (CDCl$_3$) δ 8.15 (br, 1H, NH), 8.20–7.40 (m, 6H, arom., H-6), 6.45–6.25 (m, 2H, CH=$CH_2$, H-2'), 6.03, 5.31 (2dd, 2H, CH=$CH_2$), 5.20 (m, 1H, H-4'), 4.30–4.10 (m, 4H, H-5', H-6').

In an analogous manner to the preparation of compound 21, (2S,4S)-1-[2-(benzyloxymethyl)-1,3-dioxolan-4-yl]-5-vinyluracil 103 was prepared from 102 (compound 102 was prepared according to the published procedure: J.-S. Lin, T. Kira, E. Gullen, Y. Choi, F. Qu, C. K. Chu, Y.-C. Cheng, J. Med. Chem. 1999, 42, 2212–2217). $^1$NMR (CDCl$_3$) δ 8.15 (br, 1H, NH), 8.20–7.40 (m, 6H, arom.), 6.45–6.25 (m, 2H, CH=$CH_2$, H-2'), 6.03, 5.31 (2dd, 2H, CH=$CH_2$), 5.20 (m, 1H, H-4'), 4.30–4.10 (m, 4H, H-5', H-6').

In an analogous manner to the preparation of compound 21 but replacing tributyl(vinyl)tin with 2-(tributylstannyl)furan, (2R,4R)-1-[2-(benzyloxymethyl)-1,3-dioxolan-4-yl]-5-(2-furanyl)uracil 110 was prepared from 94. $^1$NMR (CDCl$_3$) δ 8.16 (bs, 1H, NH), 8.10–7.41 (m, 6H, arom., H-6), 6.92 (d, 1H, furanyl), 6.82 (d, 1H, furanyl), 6.55 (m, 1H, furanyl), 6.32 (m, 1H, H-2'), 5.20 (m, 1H, H-4'), 4.30–4.10 (m, 4H, H-5', H-6').

In an analogous manner to the preparation of compound 21 but replacing tributyl(vinyl)tin with 2-(tributylstannyl)thiophene, (2R,4R)-1-[2-(benzyloxymethyl)-1,3-dioxolan- 4-yl]-5-(2-thienyl)uracil 111 was prepared from 94. $^1$H NMR (CDCl$_3$) δ 8.06–7.20 (m, 7H, arom., H-6), 6.85 (t, 1H, thienyl), 6.29 (m, 1H, H-2'), 5.20 (m, 1H, H-4'), 4.28–4.10 (m, 4H, H-5', H-6').

In an analogous manner to the preparation of compound 21 but replacing tributyl(vinyl)tin with 2-(tributylstannyl) furan, (2S,4S)-1-[2-(benzyloxymethyl)-1,3-dioxolan-4-yl]-5-(2-furanyl)uracil 116 was prepared from 102. $^1$H NMR (CDCl$_3$) δ 8.16 (bs, 1H, NH), 8.10–7.41 (m, 6H, arom., H-6), 6.92 (d, 1H, furanyl), 6.82 (d, 1H, furanyl), 6.55 (m, 1H, furanyl), 6.32 (m, 1H, H-2'), 5.20 (m, 1H, H-4'), 4.30–4.10 (m, 4H, H-5', H-6').

In an analogous manner to the preparation of compound 21 but replacing tributyl(vinyl)tin with 2-(tributylstannyl) thiophene, (2S,4S)-1-[2-(benzyloxymethyl)-1,3-dioxolan-4-yl]-5-(2-thienyl)uracil 117 was prepared from 102. $^1$H NMR (CDCl$_3$) δ 8.06–7.20 (m, 7H, arom., H-6), 6.85 (t, 1H, thienyl), 6.29 (m, 1H, H-2'), 5.20 (m, 1H, H-4'), 4.28–4.10 (m, 4H, H-5', H-6').

In an analogous manner to the preparation of compound 21 but replacing tributyl(vinyl)tin with tributyl(phenyl)tin, β-D-2'-deoxy-3',5'-di-O-benzoyl-5-propynyluridine 127 was prepared from 20. $^1$H NMR (CDCl$_3$) δ 8.10–7.45 (m, 11H, arom., H-6), 6.43 (m, 1H, H-1'), 5.65 (d, 1H, H-3'), 4.83–4.71 (m, 2H, H-5'), 4.61 (m, 1H, H-4'), 2.79, 2.38 (2m, 2H, H-2'), 1.87 (s, 3H, CH$_3$).

In an analogous manner to the preparation of compound 21 but replacing tributyl(vinyl)tin with tributyl(phenyl)tin, β-D-2'-deoxy-3',5'-di-O-benzoyl-5-(phenylethynyl)uridine 128 was prepared from 20. $^1$H NMR (CDCl$_3$) δ 8.09–7.28 (m, 16H, arom., H-6), 6.45 (m, 1H, H-1'), 5.67 (d, 1H, H-3'), 4.88–4.76 (m, 2H, H-5'), 4.63 (m, 1H, H-4'), 2.83, 2.40 (2m, 2H, H-2').

In an analogous manner to the preparation of compound 21 but replacing tributyl(vinyl)tin with tributyl(phenyl)tin, β-D-2'-deoxy-3',5'-di-O-benzoyl-5-phenyluridine 129 was prepared from 20. $^1$NMR (CDCl$_3$) δ 8.09–7.21 (m, 16H, arom., H-6), 6.38 (m, 1H, H-1'), 5.65 (m, 1H, H-3'), 4.77 (m, 2H, H-5'), 4.60 (m, 1H, H-4'), 2.79, 2.32 (2m, 2H, H-2').

In an analogous manner to the preparation of compound 21 but replacing tributyl(vinyl)tin with tributyl(phenyl)tin, β-L-2'-deoxy-3',5'-di-O-benzoyl-5-phenyluridine 133 was prepared from 23. $^1$NMR (CDCl$_3$) δ 8.09–7.21 (m, 16H, arom., H-6), 6.38 (m, 1H, H-1'), 5.65 (m, 1H, H-3'), 4.77 (m, 2H, H-5'), 4.60 (m, 1H, H-4'), 2.79, 2.32 (2m, 2H, H-2').

Example 7

β-D-2'-Deoxy-5-vinyluridine (22)

A solution of 21 (183 mg, 0.4 mmol) in ammonium-MeOH solution (2M, 25 mL) was stirred in a stoppered flask at room temperature for 20 h, and then concentrated in vacuo. Column chromatography of the residue (CH$_2$Cl$_2$/MeOH, 9:1) gave the title compound 22 as a white crystalline solid (88 mg, 87%). $^1$NMR (DMSO-d$_6$) δ 11.37 (s, 1H, NH), 8.10 (s, 1H, H-6), 6.36 (dd, 1H, CH=CH$_2$), 6.15 (t, 1H, J=6.4 Hz, H-1'), 5.91, 5.11 (2dd, 2H, CH=CH$_2$), 5.21, 5.09 (2br, 2H, 2 OH), 4.24 (m, 1H, H-3'), 3.78 (m, 1H, H-4'), 3.59 (m, 1H, H-5'), 2.15–2.11 (m, 2H, H-2').

In an analogous manner to the preparation of compound 22, β-L-2'-deoxy-5-vinyluridine 25 was prepared from 24. $^1$H NMR (DMSO-d$_6$) δ 11.4 (s, 1H, NH), 8.10 (s, 1H, H-6), 6.36 (dd, 1H, CH=CH$_2$), 6.15 (t, 1H, J=6.4 Hz, H-1'), 5.91, 5.11 (2dd, 2H, CH=CH$_2$), 5.21, 5.10 (2br, 2H, 2 OH), 4.24 (m, 1H, H-3'), 3.78 (m, 1H, H-4'), 3.59 (m, 1H, H-5'), 2.15–2.11 (m, 2H, H-2').

In an analogous manner to the preparation of compound 22, 1-(β-L-arabinofuranosyl)-5-vinyluracil 28 was prepared from 27. $^1$NMR (DMSO-d$_6$) δ 11.42 (s, 1H, NH), 7.89 (s, 1H, H-6), 6.37 (dd, 1H, CH=CH$_2$), 6.01 (d, 1H, H-1'), 5.87, 5.08 (2dd, 2H, CH=CH$_2$), 5.62 (d, 1H, OH), 5.48 (d, 1H, OH), 5.18 (t, 1H, OH), 4.05 (m, 1H, H-2'), 3.93 (m, 1H, H-3'), 3.73 (m, 1H, H-4'), 3.65 (m, 2H, H-5').

In an analogous manner to the preparation of compound 22, 1-(β-D-arabinofuranosyl)-5-vinyluracil 31 was prepared from 30. $^1$H NMR (DMSO-d$_6$) δ 11.42 (s, 1H, NH), 7.90 (s, 1H, H-6), 6.37 (dd, 1H, CH=CH$_2$), 6.01 (d, 1H, H-1'), 5.87, 5.08 (2dd, 2H, CH=CH$_2$), 5.62 (d, 1H, OH), 5.48 (d, 1H, OH), 5.18 (t, 1H, OH), 4.05 (m, 1H, H-2'), 3.93 (m, 1H, H-3'), 3.73 (m, 1H, H-4'), 3.65 (m, 2H, H-5').

In an analogous manner to the preparation of compound 22, β-D-5-vinyluridine 35 was prepared from 34. $^1$H NMR (DMSO-d$_6$) δ 11.4 (s, 1H, NH), 8.21 (s, 1H, H-6), 6.37 (dd, 1H, CH=CH$_2$), 5.78 (d, 1H, H-1'), 5.92, 5.11 (2dd, 2H, CH=CH$_2$), 5.44 (d, 1H, OH), 5.25 (d, 1H, OH), 5.10 (t, 1H, OH), 4.06 (m, 1H, H-2'), 4.01 (m, 1H, H-3'), 3.86 (m, 1H, H-4'), 3.69, 3.60 (2m, 2H, H-5').

In an analogous manner to the preparation of compound 22, 1-[(1,3-dihydroxy-2-propoxy)methyl]-5-vinyluracil 49 was prepared from 48. $^1$NMR (DMSO-d$_6$) δ 11.25 (br, 1H, NH), 7.90 (s, 1H, H-6), 7.20, 6.60 (2br, 2H, 2 OH), 6.36 (dd, 1H, CH=CH$_2$), 5.95, 5.12 (2d, 2H, CH=CH$_2$), 5.19 (s, 2H, CH 2N), 4.61 (m, 2H, CH$_2$O), 3.53 (m, 1H, CHO), 3.40 (m, 2H, CH$_2$O).

In an analogous manner to the preparation of compound 22, (±)-(1'β,3'α,4'β)-1-[3-hydroxy-4-(hydroxymethyl)cyclopentyl]-5-vinyluracil 77 was prepared from 76. $^1$H NMR (DMSO-d$_6$) δ 11.5 (bs, 1H, NH), 7.96 (s, 1H, H-6), 6.35 (dd, 1H, CH=CH$_2$), 5.90, 5.10 (2dd, 2H, CH=CH$_2$), 4.95 (m, 1H, CHN), 4.75, 4.63 (2bs, 2H, 2 OH), 4.00 (m, 1H, CHOH), 3.43 (m, 2H, CH$_2$OH), 2.25–1.75 (m, 4H, 2 CH$_2$), 1.40 (m, 1H, CH).

In an analogous manner to the preparation of compound 22, β-D-2'-deoxy-5-(2-furanyl)uridine 82 was prepared from 80. $^1$H NMR (DMSO-d$_6$) δ 11.63 (s, 1H, NH), 8.33 (s, 1H, H-6), 7.60 (s, 1H, furanyl), 6.84 (d, J=2.8 Hz, 1H, furanyl), 6.51 (m, 1H, furanyl), 6.20 (t, 1H, J=6.4 Hz, H-1'), 5.29 (d, 1H, J=4.4 Hz, OH-3'), 5.11 (t, 1H, J=4.8 Hz, OH-5'), 4.27 (m, 1H, H-3'), 3.83 (m, 1H, H-4'), 3.60 (m, 2H, H-5'), 2.16 (m, 2H, H-2').

In an analogous manner to the preparation of compound 22, β-D-2'-deoxy-5-(thien-2-yl)uridine 83 was prepared from 81. $^1$NMR (DMSO-d$_6$) δ 11.7 (s, 1H, NH), 8.57 (s, 1H, H-6), 7.45–7.44 (m, 1H, thienyl), 7.7.39–7.38 (m, 1H, thienyl), 7.05–7.03 (m, 1H, thienyl), 6.21 (t, 1H, J=6.4 Hz, H-1'), 5.31–5.27 (m, 2H, 2 OH), 4.31 (m, 1H, H-3'), 3.83 (m, 1H, H-4'), 3.68–3.63 (m, 2H, H-5'), 2.23–2.17 (m, 2H, H-2').

In an analogous manner to the preparation of compound 22, β-L-2'-deoxy-5-(2-furanyl)uridine 89 was prepared from 87. $^1$H NMR (DMSO-d$_6$) δ 11.63 (s, 1H, NH), 8.33 (s, 1H, H-6), 7.60 (s, 1H, furanyl), 6.84 (d, J=2.8 Hz, 1H, furanyl), 6.51 (m, 1H, furanyl), 6.20 (t, 1H, J=6.4 Hz, H-1'), 5.29 (d, 1H, J=4.4 Hz, OH-3'), 5.11 (t, 1H, J=4.8 Hz, OH-5'), 4.27 (m, 1H, H-3'), 3.83 (m, 1H, H-4'), 3.60 (m, 2H, H-5'), 2.16 (m, 2H, H-2').

In an analogous manner to the preparation of compound 22, β-L-2'-deoxy-5-(thien-2-yl)uridine 90 was prepared from 88. $^1$H NMR (DMSO-d$_6$) δ 11.7 (s, 1H, NH), 8.57 (s, 1H, H-6), 7.45–7.44 (m, 1H, thienyl), 7.7.39–7.38 (m, 1H, thienyl), 7.05–7.03 (m, 1H, thienyl), 6.21 (t, 1H, J=6.4 Hz, H-1'), 5.31–5.27 (m, 2H, 2 OH), 4.31 (m, 1H, H-3'), 3.83 (m, 1H, H-4'), 3.68–3.63 (m, 2H, H-5'), 2.23–2.17 (m, 2H, H-2').

In an analogous manner to the preparation of compound 22, (2R,4R)-1-[2-(hydroxymethyl)-1,3-dioxolan-4-yl]-5-vinyluracil 96 was prepared from 95. $^1$H NMR (DMSO-d$_6$) δ 11.46 (br, 1H, NH), 8.19 (s, 1H, H-6), 6.36 (dd, 1H, CH=CH$_2$), 6.23 (m, 1H, H-2'), 5.90, 5.11 (2dd, 2H, CH=CH$_2$), 5.35 (t, 1H, H-4'), 4.93 (t, 1H, OH), 4.15–4.00 (m, 2H, H-5'), 3.68 (m, 1H, H-6').

In an analogous manner to the preparation of compound 22, (2R,4R)-1-[2-(hydroxymethyl)-1,3-dioxolan-4-yl]-5-iodouracil 99 was prepared from 94. $^1$H NMR (DMSO-d$_6$) δ 11.4 (br, 1H, NH), 8.17 (s, 1H, H-6), 6.22 (m, 1H, H-2'), 5.35 (t, 1H, H-4'), 4.92 (t, 1H, OH), 4.15–4.00 (m, 2H, H-5'), 3.68 (m, 1H, H-6').

In an analogous manner to the preparation of compound 22, (2S,4S)-1-[2-(hydroxymethyl)-1,3-dioxolan-4-yl]-5-vinyluracil 104 was prepared from 103. $^1$H NMR (DMSO-d$_6$) δ 11.46 (br, 1H, NH), 8.19 (s, 1H, H-6), 6.36 (dd, 1H, CH=CH$_2$), 6.23 (m, 1H, H-2'), 5.90, 5.11 (2dd, 2H, CH=CH$_2$), 5.35 (t, 1H, H-4'), 4.93 (t, 1H, OH), 4.15–4.00 (m, 2H, H-5'), 3.68 (m, 1H, H-6').

In an analogous manner to the preparation of compound 22, (2S,4S)-1-[2-(hydroxymethyl)-1,3-dioxolan-4-yl]-5-iodouracil 107 was prepared from 102. $^1$NMR (DMSO-d$_6$) δ 11.4 (br, 1H, NH), 8.17 (s, 1H, H-6), 6.22 (m, 1H, H-2'), 5.35 (t, 1H, H-4'), 4.92 (t, 1H, OH), 4.15–4.00 (m, 2H, H-5'), 3.68 (m, 1H, H-6').

In an analogous manner to the preparation of compound 22, (2R,4R)-5-(2-furanyl)-1-[2-(hydroxymethyl)-1,3-dioxolan-4-yl]uracil 112 was prepared from 110. $^1$H NMR (DMSO-d$_6$) δ 11.6 (br, 1H, NH), 8.33 (s, 1H, H-6), 7.60 (d, 1H, furanyl), 6.84 (d, 1H, furanyl), 6.50 (d, 1H, furanyl), 6.22 (m, 1H, H-2'), 5.35 (t, 1H, H-4'), 4.92 (t, 1H, OH), 4.15–4.00 (m, 2H, H-5'), 3.68 (m, 1H, H-6').

In an analogous manner to the preparation of compound 22, (2R,4R)-1-[2-(hydroxymethyl)-1,3-dioxolan-4-yl]-5-(thien-2-yl)uracil 114 was prepared from 111. $^1$H NMR (DMSO-d$_6$) δ 11.67 (br, 1H, NH), 8.57 (s, 1H, H-6), 7.44 (dd, 1H, thienyl), 7.38 (dd, 1H, thienyl), 7.04 (dd, 1H, thienyl), 6.22 (m, 1H, H-2'), 5.35 (t, 1H, H-4'), 4.92 (t, 1H, OH), 4.15–4.00 (m, 2H, H-5'), 3.68 (m, 1H, H-6').

In an analogous manner to the preparation of compound 22, (2S,4S)-5-(2-furanyl)-1-[2-(hydroxymethyl)-1,3-dioxolan-4-yl]uracil 118 was prepared from 116. $^1$NMR (DMSO-d$_6$) δ 11.6 (br, 1H, NH), 8.33 (s, 1H, H-6), 7.60 (d, 1H, furanyl), 6.84 (d, 1H, furanyl), 6.50 (d, 1H, furanyl), 6.22 (m, 1H, H-2'), 5.35 (t, 1H, H-4'), 4.92 (t, 1H, OH), 4.15–4.00 (m, 2H, H-5'), 3.68 (m, 1H, H-6').

In an analogous manner to the preparation of compound 22, (2S,4S)-1-[2-(hydroxymethyl)-1,3-dioxolan-4-yl]-5-(thien-2-yl)uracil 120 was prepared from 117. $^1$H NMR (DMSO-d$_6$) δ 11.67 (br, 1H, NH), 8.57 (s, 1H, H-6), 7.44 (dd, 1H, thienyl), 7.38 (dd, 1H, thienyl), 7.04 (dd, 1H, thienyl), 6.22 (m, 1H, H-2'), 5.35 (t, 1H, H-4'), 4.92 (t, 1H, OH), 4.15–4.00 (m, 2H, H-5'), 3.68 (m, 1H, H-6').

In an analogous manner to the preparation of compound 22, β-D-2'-deoxy-5-propynyluridine 130 was prepared from 127. $^1$NMR (DMSO-d$_6$) δ 11.56 (s, 1H, H-6), 8.10 (s, 1H, H-6), 6.10 (t, 1H, J=6.4 Hz, H-1'), 5.23 (d, 1H, J=4.0 Hz, OH-3'), 5.09 (t, 2H, J=6.4 Hz, OH-5'), 4.21 (m, 1H, H-3'), 3.77 (m, 1H, H-4'), 3.58 (m, 1H, H-5'), 2.10 (m, 2H, H-2'), 1.97 (s, 3H, CH$_3$).

In an analogous manner to the preparation of compound 22, β-D-2'-deoxy-5-(phenylethynyl)uridine 131 was prepared from 128. $^1$H NMR (DMSO-d$_6$) δ 11.70 (s, 1H, NH), 8.37 (d, 1H, H-6), 7.47–7.39 (m, 5H, arom.), 6.12 (t, 1H, J=6.4 Hz, H-1'), 5.26 (d, 1H, J=4.0 Hz, OH-3'), 5.17 (t, 2H, J=6.4 Hz, OH-5'), 4.24 (m, 1H, H-3'), 3.80 (m, 1H, H-4'), 3.63–3.57 (m, 1H, H-5'), 2.15 (m, 2H, H-2').

In an analogous manner to the preparation of compound 22, β-D-2'-deoxy-5-phenyluridine 132 was prepared from 129. $^1$NMR (DMSO-d$_6$) δ 11.52 (s, 1H, NH), 8.20 (s, 1H, H-6), 7.55–7.29 (m, 5H, arom.), 6.24 (t, 1H, J=6.4 Hz, H-1'), 5.27 (d, 1H, J=4.4 Hz, OH-3'), 5.13 (t, 2H, J=6.4 Hz, OH-5'), 4.28 (m, 1H, H-3'), 3.81 (m, 1H, H-4'), 3.60 (m, 1H, H-5'), 2.24–2.15 (m, 2H, H-2').

In an analogous manner to the preparation of compound 22, β-L-2'-deoxy-5-phenyluridine 134 was prepared from 133. $^1$H NMR (DMSO-d$_6$) δ 11.52 (s, 1H, NH), 8.20 (s, 1H, H-6), 7.55–7.29 (m, 5H, arom.), 6.24 (t, 1H, J=6.4 Hz, H-1'), 5.27 (d, 1H, J=4.4 Hz, OH-3'), 5.13 (t, 2H, J=6.4 Hz, OH-5'), 4.28 (m, 1H, H-3'), 3.81 (m, 1H, H-4'), 3.60 (m, 1H, H-5'), 2.24–2.15 (m, 2H, H-2').

Example 8

β-2'-Deoxy-3',5'-di-O-benzoyl-5-[(2-trimethylsilyl) ethynyl]uridine (36)

To a solution of 20 (2.81 g, 5 mmol), PdCl$_2$ (89 mg, 0.5 mmol) Ph$_3$P (261 mg, 1 mmol) and CuI (95 mg, 0.5 mmol) in THF (50 mL) was added Et$_3$N (1.01 g, 10 mmol, 1.39 mL), followed by trimethylsilylacetylene (737 mg, 7.5 mmol). The mixture was heated at 40° C. for 4 h under argon, and then evaporated to dryness. The residue was purified by flash chromatography on silica gel eluting with hexane/EtOAc (9:1) to give the title compound 36 as a white solid (2.08 g, 78%). 1H NMR (CDCl$_3$) δ 8.31 (s, 1H, H-6), 8.10–7.43 (m, 10H, arom.), 6.39–6.36 (dd, 1H, H-1'), 5.60 (m, 1H, H-3'), 4.83 (dd, 1H, H-4'), 4.67–4.57 (m, 2H, H-5'), 2.81–2.76, 2.30–2.27 (2m, 2H, H-2'), 0.14 (s, 9H, 3 CH$_3$).

In an analogous manner to the preparation of compound 36, β-L-2'-deoxy-3',5'-di-O-benzoyl-5-[(2-trimethylsilyl) ethynyl]uridine 38 was prepared from 23. $^1$H NMR (CDCl$_3$) δ 8.31 (s, 1H, H-6), 8.10–7.42 (m, 10H, arom.), 6.40–6.35 (dd, 1H, H-1'), 5.60 (m, 1H, H-3'), 4.83 (dd, 1H, H-4'), 4.67–4.57 (m, 2H, H-5'), 2.81–2.76, 2.30–2.27 (2m, 2H, H-2'), 0.14 (s, 9H, 3 CH$_3$).

In an analogous manner to the preparation of compound 36, 1-(2',3',5'-tri-O-benzoyl-β-L-arabinofuranosyl)-5-[(2-trimethylsilyl)ethynyl]uracil 40 was prepared from 26. $^1$H NMR (DMSO-d$_6$) δ 11.5 (s, 1H, NH), 8.10–7.40 (m, 16H, arom., H-6), 6.23 (d, 1H, H-11'), 5.41 (m, 1H, H-2'), 5.28 (m, 1H, H-3'), 4.50–4.20 (m, 3H, H-4', H-5'), 0.15 (s, 9H, Si(CH$_3$)$_3$).

In an analogous manner to the preparation of compound 36, 1-(2',3',5'-tri-O-benzoyl-β-D-arabinofuranosyl)-5-[(2-trimethylsilyl)ethynyl]uracil 42 was prepared from 29. $^1$NMR (DMSO-d$_6$) δ 11.3 (s, 1H, NH), 8.10–7.40 (m, 16H, arom., H-6), 6.23 (d, 1H, H-1'), 5.40 (m, 1H, H-2'), 5.28 (m, 1H, H-3'), 4.50–4.20 (m, 3H, H-4', H-5'), 0.16 (s, 9H, Si(CH$_3$)$_3$).

In an analogous manner to the preparation of compound 36, 1-[[1,3-bis(acetoxy)-2-propoxy]methyl]-5-[(2-trimethylsilyl)ethynyl]uracil 50 was prepared from 47. $^1$H NMR (CDCl$_3$) δ 8.44 (br, 1H, NH), 7.64 (s, 1H, H-6), 5.27 (s, 2H, CH$_2$N), 4.21, 4.06 (2m, 5H, 2 CH$_2$, CH), 2.09 (s, 6H, 2 CH$_3$), 0.23 (s, 9H, Si(CH$_3$)$_3$).

In an analogous manner to the preparation of compound 36, (±)-(1'β,3'α,4'β)-1-[3-acetoxy-4-(acetoxymethyl)cyclopentyl]-5-[(2-trimethylsilyl)ethynyl]uracil 78 was prepared from 75. $^1$H NMR (DMSO-d$_6$) δ 11.4 (bs, 1H, NH), 8.40 (s, 1H, H-6), 5.1–4.5 (m, 2H, CHO, CHN), 4.30 (m, 2H, CH$_2$O), 2.02 (s, 6H, 2 CH$_3$), 2.25–1.05 (m, 5H, 2 CH$_2$, CH), 0.16 (s, 9H, Si(CH$_3$)$_3$).

In an analogous manner to the preparation of compound 36, (2R,4R)-1-[2-(benzyloxymethyl)-1,3-dioxolan-4-yl]-5-(2-trimethylsilylethynyl)uracil 97 was prepared from 94. $^1$NMR (CDCl$_3$) δ 8.30 (s, 1H, H-6), 8.20–7.40 (m, 5H, arom.), 6.25 (m, 1H, H-2'), 5.20 (m, 1H, H-4'), 4.30–4.10 (m, 4H, H-5', H-6'), 0.15 (s, 9H, 3 CH$_3$).

In an analogous manner to the preparation of compound 36, (2S,4S)-1-[2-(benzyloxymethyl)-1,3-dioxolan-4-yl]-5-(2-trimethylsilylethynyl)uracil 105 was prepared from 102. $^1$H NMR (CDCl$_3$) δ 8.30 (s, 1H, H-6), 8.20–7.40 ( m, 5H, arom.), 6.25 (m, 1H, H-2'), 5.20 (m, 1H, H-4'), 4.30–4.10 (m, 4H, H-5', H-6'), 0.15 (s, 9H, 3 CH$_3$).

Example 9

β-D-2'-Deoxy-5-ethynyluridine (37)

To a mixture of 36 (1.333 g, 2.5 mmol) in THF (10 mL) was added TBAF (1 M solution in THF, 2.5 mL, 2.5 mmol) and the mixture was stirred at room temperature for 30 minutes. After removal of the solvent, the residue was dissolved in CH$_2$Cl$_2$, washed with brine and concentrated. The residue was dissolved in NH$_3$—MeOH (2.0 M, 50 mL) and kept at room temperature for 20 h. After removal of the solvent by evaporation, the residue was purified by flash chromatography on silica gel eluting with CH$_2$Cl$_2$/MeOH (9:1) to give the title compound 37 as a pale yellow solid (453 mg, 72%). $^1$H NMR (DMSO-d$_6$) δ 11.65 (s, 1H, NH), 8.30 (s, 1H, H-6), 6.10 (t, 1H, H-1'), 5.26 (d, 1H, OH-3'), 5.15 (t, 1H, OH-5'), 4.23 (m, 1H, H-3'), 4.12 (s, 1H, ethynyl), 3.79 (m, 1H, H-4'), 3.61 (m, 2H, H-5'), 2.13 (m, 2H, H-2').

In an analogous manner to the preparation of compound 37, β-L-2'-deoxy-5-ethynyluridine 39 was prepared from 38. $^1$NMR (DMSO-d$_6$) δ 11.65 (s, 1H, NH), 8.30 (s, 1H, H-6), 6.10 (t, 1H, H-1'), 5.26 (d, 1H, )H-3'), 5.15 (t, 1H, OH-5'), 4.23 (m, 1H, H-3'), 4.12 (s, 1H, ethynyl), 3.79 (m, 1H, H-4'), 3.61 (m, 2H, H-5'), 2.13 (m, 2H, H-2').

In an analogous manner to the preparation of compound 37, 1-(β-L-arabinofuranosyl)-5-ethynyluracil 41 was prepared from 40. $^1$NMR (DMSO-d$_6$) δ 11.69 (s, 1H, NH), 8.37 (s, 1H, H-6), 6.02 (d, J=3.6 Hz, 1H, H-1'), 5.65, 5.54 (2d, 2H, 2 OH), 5.08 (t, 1H, OH-5'), 4.02–3.99 (m, 2H, H-2', ethynyl), 3.95–3.93 (m, 1H, H-3'), 3.82–3.78 (m, 1H, H-4'), 3.66–3.55 (m, 2H, H-5').

In an analogous manner to the preparation of compound 37, 1-(β-D-arabinofuranosyl)-5-ethynyluracil 43 was prepared from 42. $^1$H NMR (DMSO-d$_6$) δ 11.7 (s, 1H, NH), 8.37 (s, 1H, H-6), 6.02 (d, 1H, H-1'), 5.65, 5.54 (2d, 2H, 2 OH), 5.08 (t, 1H, OH-5'), 4.02–3.99 (m, 2H, H-2', ethynyl), 3.95–3.93 (m, 1H, H-3'), 3.82–3.78 (m, 1H, H-4'), 3.66–3.55 (m, 2H, H-5').

In an analogous manner to the preparation of compound 37, 1-[(1,3-dihydroxy-2-propoxy)methyl]-5-ethynyluracil 51 was prepared from 50. $^1$NMR (DMSO-d$_6$) δ 11.63 (br, 1H, NH), 8.45 (s, 1H, H-6), 7.20, 6.60 (2br, 2H, 2 OH), 5.18 (s, 2H, CH$_2$N), 4.66 (t, 2H, CH$_2$O), 4.12 (s, 1H, ethynyl), 3.54 (m, 1H, CHO), 3.40 (m, 2H, 2 CH$_2$O).

In an analogous manner to the preparation of compound 37, (±)-(1'β,3'α,4'β)-1-[3-hydroxy-4-(hydroxymethyl)cyclopentyl]-5-ethynyluracil 79 was prepared from 78. $^1$NMR (DMSO-d$_6$) δ 11.3 (bs, 1H, NH), 8.42 (s, 1H, H-6), 5.00–4.55 (m, 3H, CHN, 2 OH), 4.10 (s, 1H, ethynyl), 4.00 (m, 1H, CHOH), 3.42 (m, 2H, CH$_2$OH), 2.25–1.40 (m, 5H).

In an analogous manner to the preparation of compound 37, (2R,3R)-1-[2-(hydroxymethyl)-1,3-dioxolan-4-yl]-5-ethynyluracil 98 was prepared from 97. $^1$H NMR (DMSO-d$_6$) δ 11.38 (br, 1H, NH), 7.80 (s, 1H, H-6), 6.19 (m, 1H, H-2'), 5.61 (m, 1H, H-4'), 4.89 (br, 1H, OH), 4.22–4.05 (m, 3H, H-5', ethynyl), 3.13 (m, 1H, H-6').

In an analogous manner to the preparation of compound 37, (2S,4S)-1-[2-(hydroxymethyl)-1,3-dioxolan-4-yl]-5-ethynyluracil 106 was prepared from 105. $^1$H NMR (DMSO-d$_6$) δ 11.38 (br, 1H, NH), 7.80 (s, 1H, H-6), 6.19 (m, 1H, H-2'), 5.61 (m, 1H, H-4'), 4.89 (br, 1H, OH), 4.22–4.05 (m, 3H, H-5', ethynyl), 3.13 (m, 1H, H-6').

Example 10

1-[[1,3-Bis(benzyloxy)-2-propoxy]methyl]-5-iodouracil (45)

To a suspension of 2-O-(acetoxymethyl)-1,3-di-O-benzylglycerol (44; prepared according to Martin J. C., Dvorak C. A., Smee D. F., Matthews T. R., Verheyden J. P. H. (1983) 9-[(1,3-Dihydroxy-2-propoxy)methyl]quanine: a new potent and selective antiherpes agent, *J. Med. Chem.* 26, 759–761) (2.038 g, 5.9 mmol) and 5-iodouracil (2.106 g, 8.85 mmol) in anhydrous CH$_2$Cl$_2$ (25 mL) at room temperature was added N,O-bis-(trimethylsilyl)acetamide (BSA, 5.46 mL, 22.13 mmol), and the mixture was stirred at room temperature under nitrogen for 2 h. The resulting clear solution was cooled to 0° C., and SnCl$_4$ (1 M solution in CH$_2$Cl$_2$, 5.9 mL, 5.9 mmol) was added. The mixture was stirred at room temperature overnight, and then poured into a mixture of saturated aqueous NaHCO$_3$ and CHCl$_3$. The aqueous layer was extracted with CHCl$_3$, and the combined organic phase was evaporated. The residue was purified by flash chromatography on silica gel eluting with CH$_2$Cl$_2$/MeOH (97:3) to give the title compound 45 as a yellow oil (2.935 g, 95%). $^1$H NMR (CDCl$_3$) δ 8.59 (s, 1H, NH), 7.82 (s, 1H, H-6), 7.36–7.26 (m, 10H, arom.), 5.28 (s, 2H, CH$_2$N), 4.50 (s, 4H, 2 CH$_2$), 3.99 (m, 1H, CHO), 3.52 (m, 4H, 2 CH$_2$O).

Example 11

1-[[1,3-Dihydroxy-2-propoxy]methyl]-5-iodouracil (46)

To a solution of 45 (1.90 g, 3.64 mmol) in anhydrous CH$_2$Cl$_2$ (60 mL) at −78° C. was added BCl$_3$ (1 M solution in CH$_2$Cl$_2$, 30 mL, 30 mmol) dropwise. The mixture was stirred at −78° C. under nitrogen for 2 h, then at −60° C. for another 4 h. MeOH (10 mL) was added to quench the reaction, followed by 14% NH$_4$OH solution to adjust the mixture to pH 7. After being stirred at room temperature for 1 h, the mixture was concentrated in vacuo. The residue was purified by flash chromatography on silica gel eluting with CH$_2$Cl$_2$/MeOH (9:1 to 4:1) to give the title compound 46 as a pale yellow solid (810 mg, 65%). $^1$NMR (DMSO-d$_6$) δ 11.6 (s, 1H, NH), 8.19 (s, 1H, H-6), 7.20, 6.60 (2br, 2H, 2 OH), 5.15 (s, 2H, CH$_2$N), 4.60 (m, 2H, CH$_2$O), 3.53 (m, 1H, CHO), 3.41 (m, 2H, 2 CH$_2$O).

Example 12

1-[[1,3-Bis(acetoxy)-2-propoxy]methyl]-5-iodouracil (47)

To a solution of 46 (400 mg, 1.17 mmol), DMAP (10 mg), Et$_3$N (1.0 ML) in anhydrous CH$_2$Cl$_2$ (7 mL) at 0° C. was added Ac$_2$O (0.5 mL) dropwise, and the solution was stirred at room temperature under nitrogen overnight. After removal of the solvent by evaporation, the residue was purified by flash chromatography on silica gel eluting with CH$_2$Cl$_2$/MeOH (97:3) to give the title compound 47 as a yellow oil (499 mg, quantitative). $^1$H NMR (CDCl$_3$) δ 8.66 (br, 1H, NH), 7.78 (s, 1H, H-6), 5.26 (s, 2H, CH$_2$N), 4.23, 4.05 (2m, 5H, 2 CH$_2$, CHO), 2.07 (s, 6H, 2 CH$_3$).

In an analogous manner to the preparation of compound 47, (±)-(1'β,3'α,4'β)-1-[3-acetoxy-4-(acetoxymethyl)cyclopentyl]-5-iodouracil 75 was prepared from 72. $^1$H NMR (DMSO-d$_6$) δ 11.2 (bs, 1H, NH), 8.13 (s, 1H, H-6), 5.00 (m, 1H, CHO), 4.90 (m, 1H, CHN), 4.18, 4.05 (2m, 2H, CH$_2$O), 2.02 (s, 6H, 2 CH$_3$), 2.45–1.85 (m, 4H, 2 CH$_2$), 1.59 (m, 1H, CH).

Example 13

β-D-2'-Deoxy-3',5'-di-O-p-toluoyl-5-iodo-4'-thiouridine (55)

A suspension of 5-iodorouracil (1.071 g, 4.5 mmol) and ammonium sulfate (5 mg) in HMDS (30 mL) was heated at reflux under nitrogen atmosphere for 2 h. The excess of HMDS was evaporated in vacuo. To the residue was added a solution of 1-O-acetyl-2-deoxy-3,5-di-O-p-toluoyl-4-thio-α/β-D-ribofuranoside (54; prepared according to Secrist III J. A., Tiwari K. N., Riodan J. M., Montgomery J. A. (1991) Synthesis and biological activity of 21'-deoxy-4'-thio pyrimidine nucleosides, *J. Med. Chem.* 34, 2361–2366) (1.284 g, 3 mmol) in anhydrous CH$_3$CN (20 mL). The resulting mixture was cooled to 0° C., and TMSOTf (907 mg, 4 mmol) was added. The reaction mixture was stirred at 0° C. for 20 min, then at room temperature for 2 h. The mixture was diluted with CH$_2$Cl$_2$, washed with saturated NaHCO$_3$, dried over Na$_2$SO$_4$, filtered and concentrated to dryness. The residue was purified by flash chromatography on silica gel eluting with CH$_2$Cl$_2$/MeOH (99:1), and recrystallized from CH$_2$Cl$_2$/hexane to give the title compound 55 as a solid (563 mg, 31%). $^1$H NMR (CDCl$_3$) δ 7.96–7.25 (m, 9H, arom., H-6), 6.68 (dd, 1H, H-1'), 5.75 (m, 1H, H-3'), 4.68 (m, 2H, H-5'), 4.05 (m, 1H, H-4'), 2.75, 2.41 (2m, 2H, H-2'), 2.42 (s, 6H, 2 CH3).

In an analogous manner to the preparation of compound 55, β-D-2'-deoxy-3',5'-di-O-p-toluoyl-4'-thio-5-E-[(2-trimethylsilyl)ethynyl]uridine 58 was prepared from 54 and 5-[(2-trimethylsilyl)ethynyl]uracil (prepared according to Imamura K. & Yamamoto Y. (1997) Synthesis and in vitro evaluation of 5-closo- and 5-nido-orthocarboranyluridines as boron carriers, *Bull. Chem. Soc. Jpn.* 70, 3103–3110). $^1$NMR (CDCl$_3$) δ 8.36 (s, 1H, H-6), 7.94–7.26 (m, 9H, arom.), 6.70 (m, 1H, H-1'), 5.73 (m, 1H, H-3'), 4.70 (m, 2H, H-5'), 4.05 (m, 1H, H-4'), 2.76, 2.40 (2m, 2H, H-2'), 2.42 (s, 6H, 2 CH$_3$), 0.14 (s, 9H, Si(CH$_3$)$_3$).

In an analogous manner to the preparation of compound 55, β-D-5-E-(2-chlorovinyl)-2'-deoxy-3',5'-di-O-p-toluoyl-4'-thiouridine 60 was prepared from 54 and 5-E-(2-chlorovinyl)uracil (prepared according to Jones A. S., Verhelst G., Walker R. T. (1979) The synthesis of the potent anti-herpes virus agent, E-5-(2-bromovinyl)-2'-deoxyuridine and related compounds, *Tetrahedron Lett.* 45, 4415–4418). $^1$H NMR (DMSO-d$_6$) δ 11.6 (s, 1H, NH), 8.10 (s, 1H, H-6), 7.95–7.85 (m, 4H, arom.), 7.40–7.20 (m, 4H, arom.), 7.14 (d, J=13 Hz, 1H, vinyl), 6.64 (d, J=13 Hz, 1H, vinyl), 6.40 (t, 1H, H-1'), 5.82 (m, 1H, H-3'), 4.70–4.50 (m, 2H, H-5'), 3.95 (m, 1H, H-4'), 2.80–2.50 (m, 2H, H-2'), 2.40 (s, 6H, 2 CH$_3$).

In an analogous manner to the preparation of compound 55, 5-iodo-1-(4-thio-2,3,5-tri-O-benzyl-β-D-arabinofuranosyl)uracil 63 was prepared from 1-O-acetyl-4-thio-2,3,5-tri-O-benzyl-α/β-D-arabinofuranoside (62; prepared according to Secrist III J. A., Tiwari K. N., Shortnacy-Fowler A. T., Messini L., Riodan J. M., Montgomery J. A., (1998) Synthesis and biological activity of certain 4'-thio-D-arabinofuranosylpurine nucleosides, *J. Med. Chem.* 41, 3865–3871). $^1$NMR (CDCl$_3$) δ 8.10 (br, 1H, NH), 7.80 (s, 1H, H-6), 7.40–7.15 (m, 15H, arom.), 6.30 (d, 1H, H-1'), 4.70–4.40 (m, 6H, 3 CH$_2$), 4.20 (m, 2H, H-2', H-3'), 3.65 (m, 2H, H-5'), 3.40 (m, 1H, H-4').

In an analogous manner to the preparation of compound 55, 1-(4-thio-2,3,5-tri-O-benzyl-β-D-arabinofuranosyl)-5-[(2-trimethylsilyl)ethynyl]uracil 66 was prepared from 62. $^1$H NMR (CDCl$_3$) δ 8.30 (s, 1H, H-6), 7.42–7.15 (m, 15H, arom.), 6.29 (d, 1H, H-1'), 4.70–4.40 (m, 6H, 3 CH$_2$), 4.18 (m, 2H, 2', H-3'), 3.65 (m, 2H, H-5'), 3.40 (m, 1H, H-4'), 0.14 (s, 9H, Si(CH$_3$)$_3$).

In an analogous manner to the preparation of compound 55, 5-E-(2-chlorovinyl)-1-(4-thio-2,3,5-tri-O-benzyl-β-D-arabinofuranosyl)uracil 68 was prepared from 62. $^1$H NMR (CDCl$_3$) δ 8.2 (br, 1H, NH), 7.75 (s, 1H, H-6), 7.40–7.15 (m, 16H, arom., vinyl), 6.28 (d, 1H, H-1'), 6.00 (d, 1H, J=13 Hz, vinyl), 4.70–4.40 (m, 6H, 3 CH$_2$), 4.20 (m, 2H, H-2', H-3'), 3.65 (m, 2H, H-5'), 3.40 (m, 1H, H-4').

Example 14

β-D-2'-Deoxy-4'-thio-5-vinyluridine (57)

To a mixture of 56 (220 mg, 0.43 mmol) in MeOH (5 mL) was added NaOMe (1.0 M solution, 0.87 mL, 0.87 mmol), and the mixture was stirred at room temperature for 1 h. The solvent was evaporated, and the residue was purified by flash chromatography on silica gel eluting with CH$_2$Cl$_2$/MeOH (9:1) to give the title compound 57 as a white solid (78 mg, 67%). 1H NMR (DMSO-d$_6$) δ 11.3 (s, 1H, NH), 8.21 (s, 1H, H-6), 6.4 (dd, 1H, CH=CH$_2$), 6.28 (t, 1H, H-1'), 6.00, 5.15 (2d, 2H, CH=CH$_2$), 5.23 (m, 2H, 2 OH), 4.35 (m, 1H, H-3'), 3.64 (m, 2H, H-5'), 3.30 (m, 1H, H-4'), 2.35–2.15 (m, 2H, H-2').

In an analogous manner to the preparation of compound 57, β-D-5-E-(2-chlorovinyl)-2'-deoxy-4'-thiouridine 61 was prepared from 60. $^1$H NMR (DMSO-d$_6$) δ 11.6 (s, 1H, NH), 8.18 (s, 1H, H-6), 7.23 (d, J=13 Hz, 1H, vinyl), 6.70 (d, J=13 Hz, 1H, vinyl), 6.25 (t, 1H, H-1'), 5.27 (d, 1H, OH-3'), 5.21 (t, 1H, 1H, OH-5'), 4.35 (m, 1H, H-3'), 3.70–3.15 (m, 3H, H-5', H-4'), 2.30–2.10 (m,2H, H-2').

In an analogous manner to the preparation of compound 57, β-D-2'-deoxy-5-ethyluridine 124 was prepared from 123. $^1$NMR (DMSO-d$_6$) δ 11.3 (s, 1H, NH), 7.69 (s, 1H, H-6), 6.18 (t, 1H, J=6.8 Hz, H-1'), 5.24 (d, 1H, J=4.0 Hz, OH-3'), 5.06 (t, 1H, J=4.8 Hz, OH-5'), 4.25 (m, 1H, H-3'), 3.77 (m, H-4'), 3.57 (m, 2H, H-5'), 2.21 (q, 2H, CH$_2$), 2.09 (m, 2H, H-2'), 1.03 (t, 3H, CH$_3$).

In an analogous manner to the preparation of compound 57, β-D-5-butyl-2'-deoxyuridine 126 was prepared from 125. $^1$H NMR (DMSO-d$_6$) δ 11.24 (bs, 1H, NH), 7.68 (s, 1H, H-6), 6.16 (t, 1H, J=6.8 Hz, H-1'), 5.23, 5.04 (2bs, 2H, 2 OH), 4.23 (m, 1H, H-3'), 3.75 (m, H-4'), 3.55 (m, 2H, H-5'), 2.17 (q, 2H, CH$_2$), 2.07 (m, 2H, H-2'), 1.38, 1.26 (2m, 4H, 2 CH$_2$), 0.86 (t, 3H, CH$_3$).

Example 15

β-D-2'-Deoxy-5-ethynyl-4'-thiouridine (59)

To a mixture of 58 (440 mg, 0.76 mmol) in THF (5 mL) was added TBAF (1 M solution in THF, 0.76 mL, 0.76 mmol) and the mixture was stirred at room temperature for 30 min. After removal of the solvent, the residue was dissolved in $CH_2Cl_2$, washed with brine dried ($Na_2SO_4$), and concentrated. The residue was dissolved in MeOH (5 mL) and NaOMe (1.0 M solution in MeOH, 1.53 mL) was added. The solution was stirred at room temperature for 1 h, and then the solvent was evaporated. The residue was purified by flash chromatography on silica gel eluting with $CH_2Cl_2$/MeOH (9:1) to give the title compound 59 as a pale yellow solid (98 mg, 48%). $^1H$ NMR (DMSO-$d_6$) δ 11.4 (br, 1H, NH), 8.5 (s, 1H, H-6), 6.25 (t, 1H, H-1'), 5.20 (m, 2H, 2 OH), 4.32 (m, 1H, H-3'), 4.20 (s, 1H, ethynyl), 3.62 (m, 2H, H-5'), 3.32 (m, 1H, H-4'), 2.30–2.10 (m, 2H, H-2').

Example 16

1-(4-Thio-β-D-arabinofuranosyl)-5-vinyluracil (65)

To a solution of 64 (664 mg, 1.5 mmol) in anhydrous $CH_2Cl_2$ (10 mL) at −78° C. was added slowly $BBr_3$ (1 M solution in $CH_2Cl_2$, 7.5 mL), and the reaction mixture was stirred at −78° C. under nitrogen atmosphere for 4 h. The reaction was quenched by addition of MeOH (5 mL), and neutralized by pyridine. After removal of the solvent by evaporation, the residue was purified by flash chromatography on silica gel eluting with $CH_2Cl_2$/MeOH (4:1) to give the title compound 65 (303 mg, 77%). $^1$NMR (DMSO-$d_6$) δ 11.2 (s, 1H, NH), 8.20 (s, 1H, H-6), 6.4 (dd, 1H, CH=$CH_2$), 6.27 (d, 1H, H-1'), 6.00, 5.15 (2d, 2H, CH=$CH_2$), 5.70 (d, 1H, OH-2'), 5.40 (d, 1H, OH-3'), 5.27 (t, 1H, OH-5'), 4.00–3.95 (m, 2H, H-2', H-3'), 3.75–3.65 (m, 2H, H-5'), 3.20 (m, 1H, H-4').

In an analogous manner to the preparation of compound 65, 5-E-(2-chlorovinyl)-1-(4-thio-β-D-arabinofuranosyl) uracil 69 was prepared from 68. $^1$NMR (DMSO-$d_6$) δ 11.5 (s, 11H, NH), 8.20 (s, 11H, H-6), 7.23 (d, J=13 Hz, 1H, vinyl), 6.70 (d, J=13 Hz, 1H, vinyl), 6.26 (d, 1H, H-1'), 5.68 (d, 1H, OH-2'), 5.40 (d, 1H, OH-3'), 5.25 (t, 1H, OH-5'), 4.02–3.95 (m, 2H, H-2', H-3'), 3.75–3.60 (m, 2H, H-5'), 3.21 (m, 1H, H-4').

Example 17

5-Ethynyl-1-(4-thio-β-D-arabinofuranosyl)uracil (67)

To a mixture of 66 (940 mg, 1.5 mmol) in THF (10 mL) was added TBAF (1 M solution in THF, 1.5 mL, 1.5 mmol), and the mixture was stirred at room temperature for 30 min. After removal of the solvent, the residue was dissolved in $CH_2Cl_2$ (50 mL), washed with water, dried over $Na_2SO_4$, and evaporated to dryness in vacuo. Then the residue was dissolved in anhydrous $CH_2Cl_2$ (10 mL), and cooled to −78° C. $BBr_3$ (1 M solution in $CH_2Cl_2$, 7.5 mL) was added slowly, and the reaction mixture was stirred at −78° C. under nitrogen atmosphere for 4 h. The reaction was quenched by addition of MeOH (5 mL), and neutralized by pyridine. After removal of the solvent by evaporation, the residue was purified by flash chromatography on silica gel eluting with $CH_2Cl_2$/MeOH (4:1) to give the title compound 67 (311 mg, 73%). $^1$NMR (DMSO-$d_6$) δ 11.3 (br, 1H, NH), 8.42 (s, 1H, H-6), 6.25 (t, 1H, H-1'), 5.68 (br, 1H, OH-2'), 5.42 (d, 1H, OH-3'), 5.25 (t, 1H, OH-5'), 4.10 (s, 1H, ethynyl), 4.01–3.94 (m, 2H, H-2', H-3'), 3.72–3.60 (m, 2H, H-5'), 3.24 (m, 1H, H-4').

Example 18

β-D-5-(5-Chlorothien-2-yl)-2'-deoxyuridine (84)

A solution of 81 (618 mg, 1.1 mmol) and NCS (142 mg, 1.05 mmol) in anhydrous pyridine (10 mL) was heated at 70° C. for 4 h. After removal of the solvent, the residue was co-evaporated with toluene, and then a solution of $NH_3$—MeOH (2 M solution, 40 mL) was added. The solution was stirred in a stoppered flask at room temperature overnight. After removal of the solvent, the residue was purified by flash chromatography on silica gel eluting with $CH_2Cl_2$/MeOH (9:1) to give, after recrystallization from acetone/$CHCl_3$, the title compound 84 as a brownish-yellow crystal (208 mg, 55%). $^1H$ NMR (DMSO-$d_6$) δ 11.8 (s, 1H, NH), 8.67 (s, 1H, H-6), 7.24 (d, 1H, J=4.4 Hz, thienyl), 7.06 (d, 1H, J=4.4 Hz, thienyl), 6.19 (t, 1H, J=6.0 Hz, H-1'), 5.37 (t, 1H, J=4.8 Hz, OH-5'), 5.29 (d, 1H, J=4.4 Hz, OH-3'), 4.31 (m, 1H, H-3'), 3.84 (m, 1H, H-4'), 3.71–3.65 (m, 2H, H-5'), 2.25–2.18 (m, 2H, H-2').

In an analogous manner to the preparation of compound 84, β-L-5-(5-chlorothien-2-yl)-2'-deoxyuridine 91 was prepared from 88. $^1H$ NMR (DMSO-$d_6$) δ 11.8 (s, 1H, NH), 8.67 (s, 1H, H-6), 7.24 (d, 1H, J=4.4 Hz, thienyl), 7.06 (d, 1H, J=4.4 Hz, thienyl), 6.19 (t, 1H, J=6.0 Hz, H-1'), 5.37 (t, 1H, J=4.8 Hz, OH-5'), 5.29 (d, 1H, J=4.4 Hz, OH-3'), 4.31 (m, 1H, H-3'), 3.84 (m, 1H, H-4'), 3.71–3.65 (m, 2H, H-5'), 2.25–2.17 (m, 2H, H-2').

Example 19

β-D-5-(5-Bromothien-2-yl)-2'-deoxyuridine (85)

To a mixture of 81 (113 mg, 0.2 mmol) and $CHCl_3$ (10 mL) at room temperature was added $Br_2$—$CCl_4$ (32 mg $Br_2$ in 2 mL $CCl_4$) dropwise over a period of 15 min, and then the solution was washed twice with water. The organic phase was evaporated and co-evaporated with toluene, and then a solution of $NH_3$—MeOH (2 M solution, 30 mL) was added. The solution was stirred in a stoppered flask at room temperature overnight. After removal of the solvent, the residue was purified by flash chromatography on silica gel, eluting with $CH_2Cl_2$/MeOH (9:1) to give, after recrystallization from acetone/$CHCl_3$, the title compound 85 as a light yellow solid (49 mg, 63%). $^1$NMR (DMSO-$d_6$) δ 11.8 (s, 1H, NH), 8.67 (s, 1H, H-6), 7.21 (d, 1H, J=4.0 Hz, thienyl), 7.16 (d, 1H, J=4.0 Hz, thienyl), 6.19 (t, 1H, J=6.0 Hz, H-1'), 5.37 (t, 1H, J=4.8 Hz, OH-5'), 5.29 (d, 1H, J=4.4 Hz, OH-3'), 4.30 (m, 1H, H-3'), 3.84 (m, 1H, H-4'), 3.71–3.65 (m, 2H, H-5'), 2.25–2.18 (m, 2H, H-2').

In an analogous manner to the preparation of compound 85, β-L-5-(5-bromothien-2-yl)-2'-deoxyuridine 92 was prepared from 88. $^1H$ NMR (DMSO-$d_6$) δ 11.8 (s, 1H, NH), 8.67 (s, 1H, H-6), 7.21 (d, 1H, J=4.0 Hz, thienyl), 7.16 (d, 1H, J=4.0 Hz, thienyl), 6.19 (t, 1H, J=6.4 Hz, H-1'), 5.36 (t, 1H, J=4.4 Hz, OH-5'), 5.28 (d, 1H, J=4.4 Hz, OH-3'), 4.30 (m, 1H, H-3'), 3.83 (m, 1H, H-4'), 3.70–3.65 (m, 2H, H-5'), 2.25–2.17 (m, 2H, H-2').

In an analogous manner to the preparation of compound 85, (2R,4R)-5-(5-bromo-2-furanyl)-1-[2-(hydroxymethyl)-1,3-dioxolan-4-yl]uracil 113 was prepared from 110. $^1H$ NMR (DMSO-$d_6$) δ 11.5 (s, 1H, NH), 8.26 (s, 1H, H-6), 6.82, 6.60 (2d, 2H, furanyl), 6.19 (m, 1H, H-2'), 5.62 (m, 1H, H-4'), 4.90 (br, 1H, OH), 4.20–4.05 (m, 2H, H-5'), 3.12 (m, 1H, H-6').

In an analogous manner to the preparation of compound 85, (2R,4R)-5-(5-bromothien-2-yl)-1-[2-(hydroxymethyl)-1,3-dioxolan-4-yl]uracil 115 was prepared from 111. $^1$H NMR (DMSO-$d_6$) δ 11.8 (br, 1H, NH), 8.65 (s, 1H, H-6), 7.20 (d, 1H, thienyl), 7.16 (d, 1H, thienyl), 6.19 (m, 1H, H-2'), 5.61 (m, 1H, H-4'), 4.89 (br, 1H, OH), 4.22–4.05 (m, 2H, H-5'), 3.13 (m, 1H, H-6').

In an analogous manner to the preparation of compound 85, (2S,4S)-5-(5-bromo-2-furanyl)-1-[2-(hydroxymethyl)-1,3-dioxolan-4-yl]uracil 119 was prepared from 116. $^1$H NMR (DMSO-$d_6$) δ 11.5 (s, 1H, NH), 8.26 (s, 1H, H-6), 6.82, 6.60 (2d, 2H, furanyl), 6.19 (m, 1H, H-2'), 5.62 (m, 1H, H-4'), 4.90 (br, 1H, OH), 4.20–4.05 (m, 2H, H-5'), 3.12 (m, 1H, H-6').

In an analogous manner to the preparation of compound 85, (2S,4S)-5-(5-bromothien-2-yl)-1-[2-(hydroxymethyl)-1,3-dioxolan-4-yl]uracil 121 was prepared from 117. $^1$H NMR (DMSO-$d_6$) δ 11.8 (br, 1H, NH), 8.65 (s, 1H, H-6), 7.20 (d, 1H, thienyl), 7.16 (d, 1H, thienyl), 6.19 (m, 1H, H-2'), 5.61 (m, 1H, H-4'), 4.89 (br, 1H, OH), 4.22–4.05 (m, 2H, H-5'), 3.13 (m, 1H, H-6').

Example 20

β-D-2'-Deoxy-5-(5-iodothien-2-yl)uridine (86)

To a mixture of 81 (225 mg, 0.4 mmol) in anhydrous MeCN (10 mL) was added 12, followed by ceric ammonium nitrate (61 mg, 0.113 mmol). The mixture was stirred at room temperature for 3 h, and then the solvent was evaporated. The residue was taken into EtOAc (30 mL), 5% sodium hydrosulfite (5 mL), and brine (10 mL). The aqueous layer was extracted with EtOAc, and the combined organic phase was concentrated to dryness. Due was co-evaporated with toluene and EtOH, and then dissolved in 2 M $NH_3$—MeOH solution (30 mL). The solution was stirred in a stoppered flask at room temperature overnight. After removal of the solvent, the residue was purified by flash chromatography on silica gel eluting with $CH_2Cl_2$/MeOH (9:1) to give, after recrystallization from MeOH/acetone/$CHCl_3$, the title compound 86 as a brown solid (96 mg, 55%). $^1$NMR (DMSO-$d_6$) δ 11.8 (s, 1H, NH), 8.64 (s, 1H, H-6), 7.25 (d, 1H, J=4.0 Hz, thienyl), 7.11 (d, 1H, J=4.0 Hz, thienyl), 6.19 (t, 1H, J=6.4 Hz, H-1'), 5.36 (t, 1H, J=4.8 Hz, OH-5'), 5.29 (d, 1H, J=4.4 Hz, OH-3'), 4.30 (m, 1H, H-3'), 3.84 (m, 1H, H-4'), 3.70–3.64 (m, 2H, H-5'), 2.26–2.18 (m, 2H, H-2').

In an analogous manner to the preparation of compound 86, β-L-2'-deoxy-5-(5-iodothien-2-yl)uridine 93 was prepared from 88. $^1$H NMR (DMSO-$d_6$) δ 11.8 (s, 1H, NH), 8.64 (s, 1H, H-6), 7.25 (d, 1H, J=4.0 Hz, thienyl), 7.11 (d, 1H, J=4.0 Hz, thienyl), 6.19 (t, 1H, J=6.4 Hz, H-1'), 5.36 (t, 1H, J=4.8 Hz, OH-5'), 5.29 (d, 1H, J=4.4 Hz, OH-3'), 4.30 (m, 1H, H-3'), 3.84 (m, 1H, H-4'), 3.70–3.64 (m, 2H, H-5'), 2.25–2.17 (m, 2H, H-2').

Example 21

(2R,4R)-1-[2-(hydroxymethyl)-1,3-dioxolan-4-yl]-5-(3-hydroxypropenyl)uracil (101)

To a solution of 100 (447 mg, 1.5 mmol) in toluene (10 mL) at −78° C. was added DIBALH (1.0 M solution in hexane, 1.8 mL) in a period of 10 min. After stirring at −78° C. for 30 min, the reaction was quenched by addition of MeOH (2 mL), and the solution was allowed to warm to room temperature. Saturated sodium potassium tartrate solution was added and the mixture was filtered through a short pad of celite. The filtrate was concentrated in vacuo and the residue was purified by flash chromatography on silica gel, eluting with $CH_2Cl_2$/MeOH (9:1) to give the title compound 101 as a white solid (226 mg, 56%). $^1$H NMR (DMSO-$d_6$) δ 11.5 (s, 1H, NH), 7.62 (s, 1H, H-6), 6.25 (d, 1H, H-2'), 6.09 (d, 1H, vinyl), 5.73 (m, 1H, vinyl), 5.20 (t, 1H, H-4'), 4.90 (m, 2H, 2 OH), 4.29, 4.08 (m, 4H, H-5', $CH_2$), 3.64(dd, 2H, H-6').

In an analogous manner to the preparation of compound 100, (2S,4S)-1-[2-(hydroxymethyl)-1,3-dioxolan-4-yl]-5-(3-hydroxypropenyl)uracil 109 was prepared from 108. $^1$H NMR (DMSO-$d_6$) δ 11.5 (s, 1H, NH), 7.62 (s, 1H, H-6), 6.25 (d, 1H, H-2'), 6.09 (d, 1H, vinyl), 5.73 (m, 1H, vinyl), 5.20 (t, 1H, H-4'), 4.90 (m, 2H, 2 OH), 4.29, 4.08 (m, 4H, H-5', $CH_2$), 3.64(dd, 2H, H-6').

Example 22

β-D-2'-Deoxy-3',5'-di-O-p-toluoyl-5-ethyluridine (123)

A suspension of 5-ethyluracil (420 mg, 3 mmol) and ammonium sulfate (15 mg) in HMDS (20 mL) was heated at reflux under nitrogen atmosphere for 2 h. The excess of HMDS was evaporated in vacuo. To the residue was added $CHCl_3$ (10 mL), followed by 2-deoxy-3,5-di-O-p-toluoyl-α-D-erythro-pentofuranosyl chloride (122; 778 mg, 2 mmol; prepared according to Hoffer M, *Chem. Ber.* 1960, 93, 2771) portionwise, with stirring at room temperature. The resulting solution was stirred at room temperature overnight. The solvent was concentrated to half the original volume, and EtOH was added. The rest of $CHCl_3$ was evaporated, the precipitate was filtered, washed with EtOH, and dried in vacuo to give the title compound 123 as a white powder (890 mg, 90%). $^1$H NMR ($CDCl_3$) δ 8.08 (s, 1H, NH), 7.97–7.92 (m, 4H, arom.), 7.30–7.27 (m, 4H, arom.), 7.22 (s, 1H, H-6), 6.46 (dd, 1H, H-1'), 5.65 (d, 1H, H-3'), 4.82–4.62 (m, 2H, H-5'), 4.54 m, 1H, H-4'), 2.70, 2.34 (2m, 2H, H-2'), 2.45 (d, 6H, 2 $CH_3$), 2.07 (q, 2H, $CH_2$), 0.89 (t, 3H, $CH_3$).

In an analogous manner to the preparation of compound 100, β-D-5-butyl-2'-deoxy-3',5'-di-O-p-toluoyl-uridine 125 was prepared from 122. $^1$NMR ($CDCl_3$) δ 8.15 (s, 1H, NH), 7.97–7.92 (m, 4H, arom.), 7.30–7.27 (m, 4H, arom.), 7.23 (s, 1H, H-6), 6.46 (dd, 1H, H-1'), 5.65 (d, 1H, H-3'), 4.81–4.61 (m, 2H, H-5'), 4.53 (m, 1H, H-4'), 2.70, 2.34 (2m, 2H, H-2'), 2.44 (d, 6H, 2 $CH_3$), 2.02 (q, 2H, $CH_2$), 1.27–1.09 (m, 4H, 2 $CH_2$), 0.79 (t, 3H, $CH_3$).

Example 23

β-D-2'-Deoxy-5-(hydroxymethyl)uridine (136)

To a solution of 2'-deoxyuridine (135; 10 g, 43.8 mmol) in 0.5 N KOH (100 mL) was added paraformaldehyde (12.5 g), and the mixture was heated at 60° C. for 1 day. Additional 0.5 N KOH (150 mL) was added, and the mixture was stirred at 60° C. for 6 days. The mixture was neutralized with Dowex-50WX-8-100, and filtered. The resin was rinsed with water, and the combined filtrate was concentrated in vacuo. The oily residue was purified by flash chromatography on silica gel eluting with $CHCl_3$/MeOH (4:1) to give the title compound 136 as a yellow sticky foam (4.30 g, 38%). $^1$NMR (DMSO-$d_6$) δ 11.4 (br, 1H, NH), 7.78 (s, 1H, H-6), 6.16 (m, 1H, H-1'), 4.24 (m, 1H, H-3'), 4.12 (s, 2H, CH$_2$), 3.76 (m, H-4'), 3.57 (m, 2H, H-5'), 2.06 (m, 2H, H-2').

Example 24

Competition Assay of Thymidine Phosphorylation

This assay is an indirect measure of the relative affinity the enzyme has for each nucleoside and is used here to investigate the recognition of a nucleoside analogue by the EBV-TK (Gustafson E. A., Chillemi A. C., Sage D. R., Fingeroth J. (1998) The EBV-TK does not phosphorylate GCV or ACV and demonstrates a narrow substrate specificity compared to the HSV-1 TK. Antimicrob. Agents Chemother. 42, 2923–2931; Gustafson E. A., Schinazi R. F., Fingeroth J. (2000) HHV-8 open reading frame 21 is a thymidine and thymidylate kinase of narrow substrate specificity that efficiently phosphorylates zidovudine but not ganciclovir. J. Virol. 74, 684–692). EBV-TK was incubated in an optimized buffer with 15 μM 3H-dT as substrate in a final volume of 100 μL. The enzyme source was either lysate from 143B EBV-TK-expressing cells or purified GST EBV-TK from E. coli. The amount of enzyme was adjusted so that the reaction proceeded linearly for over 60 min. A 10-fold excess (150 μM) of the nucleoside analog being tested was included in the experiment. The reaction was halted at 30 min. by spotting 50 μL of the reaction onto positively charged DE-81 discs (Whatman). After washing four times with 5 mM ammonium formate and once with 95% ethanol, the discs were dried and counted in a scintillation counter. The CPM of the positive control reaction containing no nucleoside analog was taken as 100% activity. Effective competition with the labeled substrate $^3$H-dT resulted in a lower CPM value.

Example 25

Cytotoxicity Assay

This assay measures the ability of a candidate nucleoside to specifically eliminate EBV-infected cells in the continuous presence of drug. 143B TK- cells lack TK-1. 293 cells contain human TK-1. Therefore, these assays comparatively assess the effects of human TK expression on toxicity. Stock solutions (20–40 mM) of the compounds were prepared in sterile DMSO and then diluted to the desired concentration in growth medium. The cells (143B TK–, 293 EBV-TK or 293 Neo control cells) were cultured in the presence of drug for 5 days, and the media was replaced with fresh media containing drug on day three. Cells were then washed one time with PBS, fixed with 4% formaldehyde/1% methanol and stained with 1% crystal violet in 20% ethanol for visualization of the cell monolayer. To score the toxicity, "+" means that the cells did not survive, "–" indicates that the cells grew at the highest concentration of drug tested, and "+/–" means that the cells were still alive, but not replicating or replicating very slowly. Cultures with this designation often have media that is still "pink," indicating a slowdown of cellular metabolism. Identical samples are assessed in triplicate.

Example 26

Colony Formation Assay

This assay is designed to identify nucleosides whose toxicity is due to incorporation into cellular DNA forming a lethal lesion following a single exposure to the drug, as described for GCV (Rubsam L. Z., Davidson B. L., Shewach D. S. (1998) Superior cytotoxicity with GCV compared with ACV and 1-beta-D-arabinofuranosylthymine in HSV-TK-expressing cells: a paradigm for cell killing, Cancer Res. 58, 3873–3882). Stock solutions (20–40 mM) of the compounds were prepared in sterile DMSO and then diluted to the desired concentration in growth medium. Exponentially growing cells were incubated with the nucleoside in question for 24 h, plated in 24-well plates at 50 viable cells per well and incubated for 7–9 days in the absence of drug. Cells were fixed and stained as above and colonies were counted. A nucleoside can cause a decrease in the number of colonies, which is an indirect indication of the number of cells able to survive and to replicate after the initial exposure to drug.

Example 27

Anti-HIV and Cytotoxicity Assay

Anti-HIV-1 activity of the compounds was determined in human peripheral blood mononuclear (PBM) cells as described previously (Schinazi R. F., McMillan A., Cannon D., Mathis R., Lloyd R. M. Jr., Peck A., Sommadossi J.-P., St. Clair M., Wilson J., Furman P. A., Painter G., Choi W.-B., Liotta D. C. Antimicrob. Agents Chemother. 1992, 36, 2423; Schinazi, R. F., Sommadossi J.-P., Saalmann V., Cannon D., Xie M.-Y., Hart G., Smith G., Hahn E. Antimicrob. Agents Chemother. 1990, 34, 1061). Stock solutions (20–40 mM) of the compounds were prepared in sterile DMSO and then diluted to the desired concentration in growth medium. Cells were infected with the prototype HIV-1LAI at a multiplicity of infection of 0.01. Virus obtained from the cell supernatant was quantified on day 6 after infection by a reverse transcriptase assay using (rA)n·(dT)12–18 as template-primer. The DMSO present in the diluted solution (<0.1%) had no effect on the virus yield. AZT was included as positive control. The toxicity of some compounds was assessed in Vero, human PBM, and CEM cells, as described previously (Schinazi R. F., Sommadossi J.-P., Saalmann V., Cannon D. L., Xie M.-Y., Hart G. C., Smith G. A., Hahn E. F. Antimicrob Agents Chemother. 1990, 34, 1061–1067). Cycloheximide was included as positive cytotoxic control, and untreated cells exposed to solvent were included as negative controls. The antiviral EC$_{50}$, EC$_{90}$, and cytotoxicity IC$_{50}$ were obtained from the concentration-response curve using the median effective method described previously (Chou T.-C.; Talalay P. Adv. Enzyme Regul. 1984, 22, 27–55; Belen'kii M. S., Schinazi R. F. Antiviral Res. 1994, 25, 1–11).

Example 28

Production of Cells Expressing EBV-TK (or KHSV-TK)

The Epstein-Barr virus (EBV) thymidine kinase (TK) gene from the viral strain B-958 was cloned into the vector pCMV as described (Gustafson E A, Chillemi A C, Sage D R, Fingeroth J D. The Epstein-Barr virus thymidine kinase does not phosphorylate ganciclovir or acyclovir and demonstrates a narrow substrate specificity compared to the herpes simplex virus type 1 thymidine kinase. Antimicrob Agents Chemother 1998; 42(11), 2923–31). The vector was then transfected using Lipofectamine reagent into 2 human cell lines. The cells were selected and expression of the TK gene (RNA and protein) was determined. The cells were used to create two assay systems to assess the ability of EBV-TK to sensitize cells to candidate nucleoside analogs. Cells that expressed KHSV-TK were similarly prepared for assay.

Example 29

Production of 143B TK-human Osteosarcoma Cells that Express EBV-TK (or KHSV-TK)

143B TK− osteosarcoma cells were obtained from ATCC. These cells contain a mutated human TK1 gene and do not synthesize human TK1 RNA/protein. They do synthesize human TK 2 and thymidylate synthase. They are maintained in media containing 5-bromodeoxyuridine when not in use, to prevent reversion to a TK$^+$ phenotype. The cells cannot utilize the thymidine salvage pathway unless a protein with effective thymidine kinase activity is introduced. Cells transfected with EBV-TK were selected with HAT (hypoxanthine, aminopterin, thymidine). The aminopterin component, an antifolate blocks reactions involving tetrahydrofolate in the normal de novo synthesis of purine nucleoside monophosphates and thymidine monophosphate. This produces reliance on the salvage pathways for survival.

EBV-TK transfectants grew as clones. Both multiple individual clones and bulk populations (a mixture of clones) were utilized in different experiments. Cells that were transfected with an empty control vector that did not express TK did not grow at all in HAT.

All cells that survived selection expressed EBV-TK. This was documented by 2 methods (1) detection of EBV-TK RNA (Northern blot hybridization or RNA dot blot hybridization using the EBV-TK containing genomic fragment BXLF1 as probe ) and/or (2) detection of EBV-TK protein (immunoblot using human heteroantisera from patients with nasopharyngeal carcinoma known to have high titer antibody to EBV-TK or more recently with a monospecific rabbit heteroantisera to purified EBV-TK). EBV-TK-bearing cells were utilized shortly after selection and frozen. Transfectants were repeatedly documented to be human TK1 negative by RNA blot hybridization. Additional control cell lines were also established. 143B TK-cells were similarly transfected with HSV-1 TK, KHSV (KSHV) TK and human TK-1. Preparation of the respective plasmids used for transfection was as described in Gustafson E A, Chillemi A C, Sage D R, and Fingeroth J D. The Epstein-Barr virus thymidine kinase does not phosphorylate ganciclovir or acyclovir and demonstrates a narrow substrate specificity compared to the herpes simplex virus type 1 thymidine kinase. *Antimicrob Agents Chemother* 1998; 42(11), 2923–31 and Gustafson E A, Schinazi R F, and Fingeroth J D. Human herpesvirus 8 open reading frame 21 is a thymidine and thymidylate kinase of narrow substrate specificity that efficiently phosphorylates zidovudine but not ganciclovir. *J Virol* 2000;74(2), 684–92). Expression was documented by RNA blot hybridization.

To eliminate the need for HAT selection in some experiments EBV-TK-bearing 143B TK− cells (and controls i.e. 143B TK-cells alone or 143B TK-cells expressing respectively HSV1-TK, KHSV-TK, human TK1 were removed from HAT selection and retransfected with the plasmid pSV2 neo which confers resistance to Geneticin (G418). The cells were then selected with G418. Clonal expression of EBV-TK was documented by Northern blot hybridization and/or by immunoblot. Cells were reanalyzed as indicated prior to relevant experiments. These cells were used to screen candidate nucleoside analogs. They provide an effective screen as they clearly discriminate the activities provided by the respective TKs in an in vitro assay. Compounds that are toxic to EBV-TK-expressing cells but not toxic to 143B TK cells or to 143B human TK1-expressing cells (in the presence or absence of HAT selection) are demonstrated to have EBV-TK specific cytotoxic activity. The activity of candidate compounds is further compared with HSV1-TK and KHSV-TK-expressing 143B TK-cells, providing information that may have additional therapeutic applications.

Example 30

Production of 293 Human Embryonic Kidney Cells that Express EBV-TK (or KHSV-TK)

293 cells were obtained from ATCC. These cells are human embryonic kidney cells immortalized with sheared adenovirus DNA and express the adenovirus proteins E1A and E1B. 293 cells express human TK1 and TK2. For production of 293 EBV-TK cells, 293 cells were co-transfected with pCMV EBV-TK and pSV2 neo or with pCMV control and pSV2 neo at a 20:1 ratio (typically 2–10 μg of pCMV EBV-TK and 0.1–0.5 μg pSV2neo). The transferred cells were selected with G418 (1 mg/ml). Clones were documented to express EBV-TK as described above.

293 KHSV-TK cells were prepared similarly using the vector pCMV KHSV-TK together with pSV2 neo (co-transfection) or the single vector pcDNA3-KHSV-TK (which contains an endogenous selectable neo marker). Clones were documented to express KHSV-TK by RNA blot hybridization. Positive clones were also pooled to produce bulk populations.

293 EBV-TK neo (clones and bulk) were used to screen candidate nucleoside analogs in the 2 independent assays described in Examples 25 and 26.

Example 31

Cytotoxicity Assays (143B TK- and 293 Transfectants)

Two cell systems are employed to determine the toxicity of each nucleoside. The information obtained depends upon the system used. In 143B TK-cells, cytotoxic drugs that are dependent upon phosphorylation by a TK are easily identified. 143B TK-cells expressing either EBV-TK or hTK1 permit assessment of whether either enzyme independently may cause a drug to become cytotoxic. Thus, drugs that can be activated by hTK1, which would cause non-specific cytotoxicity, are readily identified. One drawback is that these cells are grown in HAT media that "forces" nucleosides through the TK salvage pathway (EBV-TK or hTK1). A false positive may arise if a nucleoside out-competes dT for phosphorylation such that sufficient amounts of dT are not available for cellular replication. This toxicity may not be present or may be reduced in a cell that has the synthetic as well as salvage pathways available for dTTP production. For this reason, the 293 system was developed. These cells have endogenous hTK1 and EBV-TK is maintained by selection in G418. Thus, the normal hTK1 salvage pathway is operational, and nucleosides can be expected to flux through the cells normally. Drugs are incubated with 293 cells transformed with a neomycin (Neo) expressing plasmid (Neo control) and with cells transfected with the same plasmid also expressing EBV-TK. A nucleoside selectively activated by EBV-TK should cause toxicity on 293 EBV-TK and not on 293 Neo control cells. In both the 143B and 293 cell systems, toxicity is evaluated by cell survival. The cells are cultured in the presence of drug for 5 days, and the media replaced with fresh media containing drug on day 3. Cells are then washed once with PBS, fixed with 4% formaldehyde/1% methanol and stained with 1% crystal violet in 20% ethanol for visualization of the cell monolayer. To score the toxicity, "+" means that the cells did not survive, "−" indicates that the cells grew fine at the highest concentration of drug tested, and "+/−" means that the cells were still alive, but not replicating or replicating very slowly (media remains "pink," indicating a slowdown of cellular metabolism). Direct quantitation was performed by counting of cells in the presence of trypan blue stain to exclude dead cells (blinded technician). All assays were performed in triplicate. Although other methods are available, trypan blue exclusion has provided a superior measurement of cell death when compared with assays such as MTT that effectively document growth inhibition, but not death.

Example 32

Colony Formation Assay (293 Transfectants)

This assay is designed to identify nucleosides whose toxicity is due to incorporation into cellular DNA forming a lethal lesion as described for GCV (Rubsam L Z, Davidson B L, and Shewach D S. "Superior cytotoxicity with ganciclovir compared with acyclovir and 1-β-D-arabinofuranosylthymine in herpes simplex virus-thymidine kinase-expressing cells: a novel paradigm for cell killing" *Cancer Res* 1998; 58(17):3873–82). Such toxicity is not dependent upon constant exposure to drug, but only exposure to drug during log phase growth. Nucleosides that act via a different mechanism, such as chain termination or inhibition of an enzyme in a metabolic pathway, are often only cytostatic, and the cells may return to normal growth after drug removal. Unlike the general cytotoxicity screen, such nucleosides do not demonstrate increased cytotoxicity in this assay. Exponentially growing cells are incubated with the candidate nucleoside for 24 hours, plated in 24-well plates at 50 viable cells/well and incubated for 7–9 days in the absence of drug. Cells are fixed and stained as above and colonies are counted. A nucleoside that works effectively causes a decrease in the number of colonies, which is a direct indication of the number of cells able to survive and replicate after the initial exposure to drug.

This invention has been described with reference to its preferred embodiments. Variations and modifications of the invention, will be obvious to those skilled in the art from the foregoing detailed description of the invention. It is intended that all of these variations and modifications be included within the scope of this invention.

We claim:

1. A method for treating an animal infected with Epstein-Barr virus or KHSV comprising administering to said animal an effective amount of a compound or pharmaceutically acceptable salt thereof, said compound is selected from the group consisting of (2S,4S)-5-(2-furanyl)-1-[2-(hydroxymethyl)-1,3-dioxolan-4-yl]uracil, (2S,4S)-5-(5-bromo-2-furanyl)-1-[2-(hydroxymethyl)-1,3-dioxolan-4-yl]uracil, (2S,4S)-5-(2-thienyl)-1-[2-2-(hydroxymethyl)-1,3-dioxolan-4-yl]uracil and (2S,4S)-5-(5-bromthien-2-yl))-1-[2-(hydroxymethyl)-1,3-dioxolan-4-yl]uracil.

2. The method of claim 1, wherein the compound is (2S,4S)-5-(2-furanyl)-1-[2-(hydroxymethyl)-1,3-dioxolan-4-yl]uracil.

3. The method of claim 1 wherein the compound is (2S,4S)-5-(5-bromo-2-furanyl)-1-[2-(hydroxymethyl)-1,3-dioxolan-4-yl]uracil.

4. The method of claim 1 wherein the compound is (2S,4S)-5-(2-thienyl)-1-[2-(hydroxymethyl)-1,3-dioxolan-4-yl]uracil.

5. The method of claim 1 wherein the compound is (2S,4S)-5-(5-bromthien-2-yl)- 1-[2-(hydroxyxmethyl)-1,3-diaxolan-4-yl]uracil.

6. The method of claim 1, wherein the animal is a human.

7. The method of claim 2, wherein the animal is a human.

8. The method of claim 3, wherein the animal is a human.

9. The method of claim 4, wherein the animal is a human.

10. The method of claim 5, wherein the animal is a human.

* * * * *

UNITED STATES PATENT AND TRADEMARK OFFICE
CERTIFICATE OF CORRECTION

| | | |
|---|---|---|
| PATENT NO. | : 7,211,570 B2 | Page 1 of 1 |
| APPLICATION NO. | : 10/326444 | |
| DATED | : May 1, 2007 | |
| INVENTOR(S) | : Raymond F. Schinazi et al. | |

It is certified that error appears in the above-identified patent and that said Letters Patent is hereby corrected as shown below:

Please insert the following statement at Column 1, line 6:

--STATEMENT REGARDING FEDERALLY SPONSORED RESEARCH
Research for the development of the subject matter contained herein was partially funded by National Institute of Health Grant Nos. CA085157, CA085083, CA093200, and DE012186.--

Signed and Sealed this

Seventh Day of August, 2007

JON W. DUDAS
*Director of the United States Patent and Trademark Office*